(12) United States Patent
Nolan

(10) Patent No.: US 12,318,539 B2
(45) Date of Patent: Jun. 3, 2025

(54) APPARATUS AND METHOD FOR IMPROVED ASSISTED VENTILATION

(71) Applicant: CoLabs Medical, Inc., Morgan Hill, CA (US)

(72) Inventor: Clay Nolan, Carmel, CA (US)

(73) Assignee: CoLabs Medical, Inc., Stony Brook, NY (US)

( * ) Notice: Subject to any disclaimer, the term of this patent is extended or adjusted under 35 U.S.C. 154(b) by 749 days.

(21) Appl. No.: 17/014,904

(22) Filed: Sep. 8, 2020

(65) Prior Publication Data

US 2021/0093814 A1  Apr. 1, 2021

Related U.S. Application Data

(60) Provisional application No. 62/896,355, filed on Sep. 5, 2019.

(51) Int. Cl.
| | | |
|---|---|---|
| A61M 16/00 | (2006.01) | |
| A61M 16/04 | (2006.01) | |
| A61M 16/06 | (2006.01) | |
| A61M 16/20 | (2006.01) | |

(52) U.S. Cl.
CPC ...... *A61M 16/022* (2017.08); *A61M 16/0434* (2013.01); *A61M 16/0463* (2013.01); *A61M 16/0475* (2014.02); *A61M 16/06* (2013.01); *A61M 16/209* (2014.02); *A61M 2016/0027* (2013.01); *A61M 2205/581* (2013.01); *A61M 2205/583* (2013.01); *A61M 2210/1032* (2013.01)

(58) Field of Classification Search
CPC ............... A61M 16/022; A61M 16/04; A61M 16/0463; A61M 16/0475; A61M 16/0434; A61M 2016/0027; A61M 2210/1032
See application file for complete search history.

(56) References Cited

U.S. PATENT DOCUMENTS

| | | |
|---|---|---|
| 3,861,395 A | 1/1975 | Taniguchi |
| 4,148,318 A | 4/1979 | Meyer |
| 9,586,015 B1* | 3/2017 | Lindner ............ A61M 16/0078 |
| 2006/0149128 A1 | 7/2006 | Baror |
| 2006/0287604 A1 | 12/2006 | Hickey |
| 2007/0137651 A1 | 6/2007 | Glassenberg et al. |
| 2009/0277447 A1* | 11/2009 | Voss ................. A61M 16/0051 |
| | | 601/41 |
| 2010/0326443 A1 | 12/2010 | Steen et al. |

(Continued)

FOREIGN PATENT DOCUMENTS

| | | |
|---|---|---|
| WO | WO 2015/143452 | 9/2015 |
| WO | WO 2021/046537 | 3/2021 |

*Primary Examiner* — Margaret M Luarca
*Assistant Examiner* — Sarah B Lederer
(74) *Attorney, Agent, or Firm* — Levine Bagade Han LLP

(57) ABSTRACT

Devices and methods for allowing for improved assisted ventilation of a patient. The methods and devices provide a number of benefits over conventional approaches for assisted ventilation. For example, the methods and devices described herein permit blind insertion of a device that can allow ventilation regardless of whether the device is positioned within a trachea or an esophagus. In addition, the methods and device allow for timed delivery of ventilations based on a condition of a thoracic cavity to increase the amount and efficiency of blood flow during a resuscitation procedure.

7 Claims, 43 Drawing Sheets

(56) References Cited

U.S. PATENT DOCUMENTS

| | | | |
|---|---|---|---|
| 2015/0231028 A1* | 8/2015 | Belalcazar | A61M 16/0858 601/43 |
| 2015/0265790 A1* | 9/2015 | Nolan | A61M 16/0486 128/202.16 |
| 2015/0297847 A1* | 10/2015 | Nolan | A61M 16/0411 128/202.16 |

* cited by examiner

| | Component | Description | Part | | |
|---|---|---|---|---|---|
| 1 | M1 | Operation Valve | Clippard TV-4DP or Equiv | | |
| 2 | M2 | Mode Valve | TV-4DMP | | |
| 3 | P1 | Medial Supply Valve | MJV-4, Pilot MVA-10 | | |
| 4 | P2 | Distal Supply Valve | MJV-4, Pilot MPA-3 | | |
| 5 | P3 | Pulse Valve | FV-3P, Pilot MPA-10 | | |
| 6 | P4 | Ventilation Selector Valve | FV-3P, Pilot MPA-3 | | |
| 7 | F1 | Reset Timing Flow Control Valve | JFC-3AR | | |
| 8 | F2 | Pulse Timing Flow Control Valve | JFC-3AR | | |
| 9 | F3 | On-Demand Flow Control Valve | (10-32 threads) | | |
| 10 | E1 | Accumulator Quick Exhaust | MEV-2 | | |
| 11 | S1 | Ventilation Supply Shuttle Valve | MSV-1444 | | |
| 12 | S2 | Vacuum Supply Shuttle Valve | MSV-1444 | | |
| 13 | R1 | Pulse Pressure Relief Valve | Smart Products, 2x15psi | | |
| 14 | R2 | Pulse Pilot Relief Valve | Smart Products, 0.5psi | | |
| 15 | I1 | Medial Ventilation Indicator | IND-3G | | |
| 16 | I2 | Distal Ventilation Indicator | IND-3G | | |
| 17 | I3 | Vacuum Indicator | IND-3G | | |
| 18 | G1 | Vacuum Generator | SMC | | |
| 19 | V1 | Pulse Accumulator | MAT-4.0 | | |

*FIG. 8B*

| Operational Mode | Manual Valve | | Pilot Valve | | | | Indicator | | | Output | | |
|---|---|---|---|---|---|---|---|---|---|---|---|---|
| | 1 | 2 | 1 | 2 | 3 | 4 | 1 | 2 | 3 | V | M | D |
| 0 | 2 | (any) | N/A | N/A | N/A | N/A | OFF | OFF | OFF | | | |
| 1 | 3 | (any) | N/A | N/A | N/A | N/A | OFF | OFF | ON | √ | | |
| 2 | 1 | 1 | 1 | 1 | N/A | N/A | OFF | OFF | ON | √ | | |
| 3A | 1 | 1 | 1 | 2 | 1 | 2 | OFF | ON | OFF | | | |
| 3B | 1 | 1 | 1 | 2 | 2 | 2 | OFF | ON | OFF | | √ | Fixed Vol |
| 4A | 1 | 1 | 2 | 1 | 1 | 1 | ON | OFF | ON | √ | | |
| 4B | 1 | 1 | 2 | 1 | 2 | 1 | ON | OFF | ON | √ | √ | Fixed Vol |
| 5 | 1 | 2 | 1 | 2 | N/A | 2 | OFF | ON | OFF | | | |
| 6 | 1 | 3 | 1 | 2 | N/A | 2 | OFF | ON | OFF | | √ | Continuous |
| 7 | 1 | 2 | 2 | 1 | N/A | 1 | ON | OFF | ON | √ | | |
| 8 | 1 | 3 | 2 | 1 | N/A | 1 | ON | OFF | ON | √ | √ | Continuous |

*FIG. 8C*

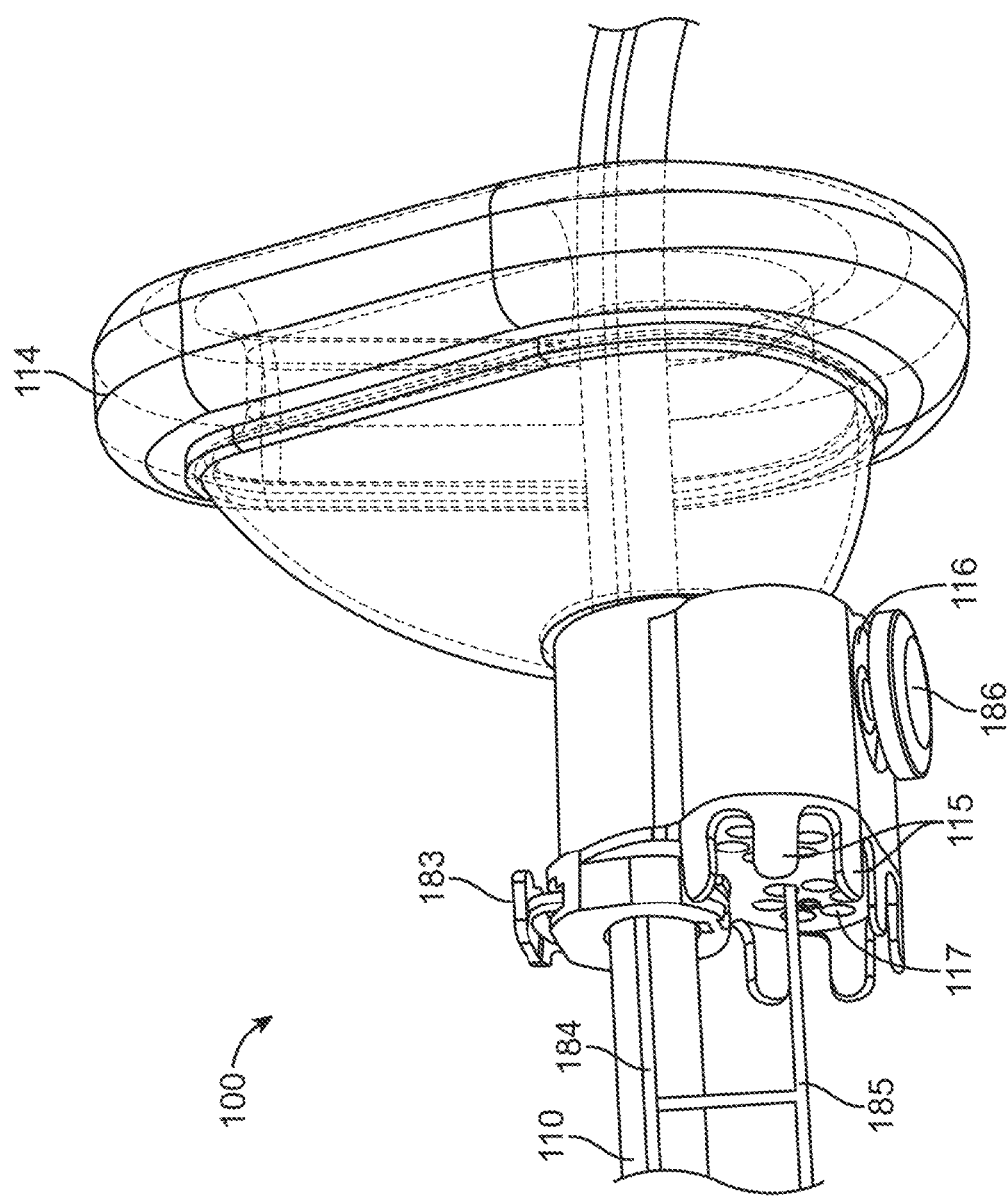

Edge delay (B)

- Shifts an entire pulse by a user-adjustable amount ($t_1$)

IN

OUT

OR gate (E)

- Outputs a HIGH signal if either input is HIGH
- In this implementation, a LOW output closes the valve
  - The watchdog input is inverted before going into the gate

| | | | | Timeout |
|---|---|---|---|---|
| LOW | HIGH | LOW | HIGH | OPEN | 
| LOW | HIGH | HIGH | HIGH | OPEN | Timeout (during a chest compression- not actually possible to reach this state) |
| HIGH | LOW | LOW | LOW | CLOSED | Between chest compressions, not timed out |
| HIGH | LOW | HIGH | HIGH | OPEN | 500 ms after a chest compression, opening valve to admit air, not timed out |

FIG. 21

APPARATUS AND METHOD FOR IMPROVED ASSISTED VENTILATION

CROSS-REFERENCE TO RELATED APPLICATIONS

The present application is a non-provisional of U.S. provisional application No. 62/896,355 filed Sep. 5, 2019, the entirety of which is incorporated by reference. This application is also related to PCT/US2020/049744, the entirety of which is incorporated by reference.

BACKGROUND OF THE INVENTION

Intubation is the placement of a tube of an intubation device into an airway lumen of the body of a patient to provide assisted ventilation of the lungs to maintain a supply of oxygen to the blood in those cases where the patient is unable to breathe on his or her own. Intubation in cases of respiratory distress involves the placement of a tube into the trachea of the patient. Tracheal intubation also involves the positioning of an endotracheal tube into a patient's trachea through the vocal cords, so the caregiver must also be careful to avoid injuring the vocal cords. In many cases, care must be taken when intubating a patient since improper placement of the tube can result in additional harm to the patient. For example, many conventional intubation devices rely on an inflatable cuff that forms a seal against the lumen wall to maintain a position of the tube within the lumen. Over-inflation of the cuff can cause internal bleeding in the patient. Another significant problem is that extreme care must be taken to avoid positioning the intubation tube within the esophagus rather than the trachea. In such cases, with conventional devices, the first responder or medical practitioner cannot properly ventilate the patient and the patient can suffer further injury.

Even properly trained medical caregivers and first responders must proceed with caution during intubation to avoid misplacement of the intubation device or to avoid unwanted insertion errors and risk of injury. Delay and/or misplacement of the endotracheal tube, such as misplacement of the endotracheal tube into the esophagus, can potentially result in neurological damage or death. Improper positioning of the endotracheal tube also can compromise airway protection or result in inadequate ventilation. It is therefore imperative to intubate a patient quickly and position the endotracheal tube correctly when a medical condition arises.

To reduce the risk of complications during intubation, the caregiver, whether a first responder, such as an emergency medical technician, paramedic, or a nurse or physician must proceed as quickly as possible yet with caution to avoid the potential complications. In addition, a first responder must often attempt to intubate the patient in a less than desirable location such as a bathroom, restaurant, or other area not conducive to providing proper medical treatment and care.

Assisted ventilation in cases of cardiac arrest also requires prompt and accurate placement of an intubation device within the trachea so that chest compressions can occur. In such cases, intubation allows for ventilation of the lungs and a supply of oxygen to the blood while chest compressions provide circulation of the blood.

The American Heart Association's protocols for cardiopulmonary resuscitation (CPR) previously required pausing after every fifteen chest compressions to allow for two ventilations. The American Heart Association's 2010 protocols decreased the frequency of ventilations such that chest compressions are to be paused after every thirty compressions to allow for two ventilations. It is believed that the main reasons supporting the change in protocol are: 1) reduce the amount of intra-thoracic pressure associated with positive pressure ventilations since positive pressure ventilations decrease the efficiency of the heart; and 2) to minimize the interruptions of chest compressions to maintain constant arterial pressure. Accordingly, now most caregivers only simultaneously ventilate the patient and provide compressions if the patient is properly intubated.

FIG. 1 provides a partial view of a patient's oral cavity 10, tongue 12 and pharynx 14 where the pharynx 14 is the membrane-lined cavity at the rear of the oral cavity 10. The pharynx 14 includes openings of the esophagus 16 and trachea 18. As shown, the openings to the esophagus 16 and trachea 18 are adjacent to one another. When a medical caregiver attempts to intubate a patient, the caregiver shall attempt to position the intubation device within the trachea 18 to provide oxygen to the lungs 2. As noted above, the caregiver shall attempt to avoid positioning the intubation device within the esophagus 16 and in doing so often must proceed slowly and with caution to avoid causing undesired trauma to vocal cords or other structures within the body.

The wall of the esophagus 16 is composed of striated and smooth muscle. Since the esophagus 16 relies on peristalsis to move food downward towards the stomach, the walls of the esophagus 16 are naturally compliant and do not have any structural reinforcement. The trachea 18, on the other hand, is relatively stronger and is naturally designed not to collapse given its function of transporting air to the bronchi and lungs 2. The wall of the trachea 18 includes a number of cartilaginous semicircular rings 20 that prevent the trachea 18 from collapsing. The trachea 20 lies anteriorly to the esophagus 16 where the openings of the esophagus 16 and trachea are separated by a tiny flap, the epiglottis 22. The epiglottis 22 protects the trachea when the individual swallows food or other substances.

FIG. 2 illustrates a conventional device 50 used for intubating a patient. As shown, the device 50 is inserted through the mouth and oral cavity into the trachea 18. The caregiver must navigate the device 50 into the trachea 18 rather than the esophagus while traversing the epiglottis 22 and vocal cords 24. The caregiver must take particular care to avoid causing damage to the vocal cords 24. Once properly positioned, the caregiver can optionally inflate 52 a balloon on the device 50 to anchor the device within the trachea 18. After the caregiver confirms placement of the device 50, ventilation of the patient can take place.

Presently, the Combitube, supplied by Nellcor, is commonly used for airway management. The Combitube, also known as a double-lumen airway, is a blind insertion airway device (BIAD) used by first responders as well as in an emergency room setting. The Combitube is intended to allow for tracheal intubation of a patient in respiratory distress by use of a cuffed, double-lumen tube. The double lumen tube is inserted into the patient's airway to allow for ventilation of the patient's lungs. Inflation of the cuff allows the device to function similarly to an endotracheal tube and usually closes off the esophagus, allowing ventilation and preventing pulmonary aspiration of gastric contents.

However, placement of traditional intubation devices is very difficult due to the risk of improperly positioning the device. The risk of a device being improperly positioned can be fatal if not recognized. The conventional devices described above require positioning by an individual that is well trained in positioning such devices. Furthermore, even well-trained individuals must proceed with caution when placing conventional devices.

In addition, there remains a need to improve timing of air delivery during artificial ventilations of a patient. This need especially remains where the patient is experiencing distress and requires both ventilation for oxygen and chest compression to re-establish blood circulation. Presently, if the act of artificially ventilating the individual (e.g., through assisted ventilation or mouth-to-mouth) and providing chest compressions is not timed, such as during normal CPR, normal artificial ventilation of the individual can work against the effectiveness of the compression. For instance, assisted ventilation by repeatedly delivering a large bolus of air can raise the pressure within the thoracic cavity and increase resistance by raising pressure on the heart. This back pressure can prevent the heart and lungs from filling with blood. As a result, impeding the ability of the heart and lungs to fill with blood, makes the chest compression less effective as a lower volume of blood is circulated after the compression.

There remains a need for a ventilation device and/or system that can effectively ventilate individuals and can be effectively positioned with minimal training required by the caregiver. In addition, there remains a need for such ventilation devices and methods to optimize the effect of providing assisted ventilation with chest compressions to circulate oxygenated blood within an individual.

SUMMARY OF THE INVENTION

The present disclosure includes methods and systems for treating an individual using a natural respiratory opening. In one example, the present disclosure includes systems for ventilating in an individual and increasing an efficiency of a chest compression. A variation of the system includes a ventilation device configured for insertion within a respiratory opening of the individual and having a working portion for positioning within a body passageway of the individual; the ventilation device having a pressure lumen exposed at the working portion, the pressure lumen in fluid communication with a sensor configured to detect a pressure change within the body passageway using the pressure lumen; the ventilation device having a control system configured for delivering a bolus of air through the working portion to ventilate the individual; where the control system is configured to alter a timing of delivery of the bolus of air upon detecting the pressure change in the body passageway resulting from the chest compression and to deliver the bolus of air after the chest compression at a sufficient volume to assist in re-expanding a thoracic cavity of the individual.

The present disclosure also includes a system for artificially ventilating an individual, the system comprising: a ventilation device configured for insertion within a respiratory opening of the individual and having a working end for positioning within a body passageway of the individual, the ventilation device having a pressure sensor configured to detect pressure changes within the body passage; and the ventilation device having a control system configured to deliver a bolus of air into an airway the individual at a pre-determined rate until detection of the pressure change within the body passageway, whereafter the control system is configured to alter the pre-determined rate by delaying delivery of the bolus of air until the sensor detects the pressure change in the air within the body passage, where the pressure change within the body passage results from a chest compression. The system can also deliver a bolus of air having an increased volume to assist in expanding the chest cavity after the compression. The timing of delivery of the air bolus increases the effectivity of the chest compression by both increasing both pulmonary resistance and assisting in recoil of the chest by the delivery of the air bolus. As result the chest will recoil to a greater volume, which increases the effectivity of the following chest compression and also increases circulation of blood.

The systems described herein can also include a control system that is further configured to provide a feedback the pressure change in the body passageway.

The systems described herein can also include control systems configured to provide the feedback based on a quality of the chest compression by determining a change in a volume of air in the thoracic cavity. In one example the feedback comprises an indicator signal indicating to identify desired times of chest compression. Another variation include a system where the working portion comprises a distal opening fluidly coupled to a first lumen and a medial opening fluidly coupled to a second lumen; wherein the control system is configured to draw suction through the distal opening within the body passageway and maintaining the suction for a period of time; the control system is further configured to determine whether the body passageway is drawn against the distal opening by the suction and to ventilate the individual through the first lumen after failing to determine that the body passageway is drawn against the distal opening; and ventilate the individual through the second lumen after determining that the body passageway is drawn against the distal opening and maintaining suction while ventilating through the second lumen.

In another variation, the system can include an inflatable anchor on the working portion. The inflatable anchor can comprise a balloon coupled to the working portion of the ventilation device. Moreover, a proximal portion of the ventilation device further comprises a face mask. In one example, a proximal portion of the ventilation device further comprises a reinforced section to prevent collapse of the ventilation device in a mouth of the individual. A proximal portion of the ventilation device can also further comprise a pressure relief valve to adjust ventilation parameters of the individual.

The present disclosures also include methods for ventilating in an individual and increasing an efficiency of a chest compression. For example, such a method can include inserting a device within a respiratory opening of the individual, the device having a working portion for positioning within a body passageway of the individual, the device having a pressure lumen exposed at the working portion; detecting a pressure change within the body passageway using the pressure lumen; delivering a bolus of air through the working portion to ventilate the individual; altering a timing of delivery of the bolus of air upon detecting the pressure change in the body passageway resulting from the chest compression to deliver a delayed bolus of air after the chest compression; and delivering the delayed bolus of air at a sufficient volume to assist in re-expanding a thoracic cavity of the individual which increases an effectiveness of a subsequent chest compression and increases circulation of blood.

In another variation of the method the working portion includes a distal opening fluidly coupled to a first lumen and a medial opening fluidly coupled to a second lumen, the method further comprising: pulling a suction force through a distal opening of the device and maintaining the suction force for a period of time; ventilating the individual through the first lumen if tissue from the body passageway does not seal the distal opening; and ventilating the individual through the second lumen and maintaining the suction force through the distal opening if the tissue from the body passageway seals the distal opening.

The method can also include initially ventilating through the second lumen during application of suction through the first lumen.

Another variation of a method disclosed herein includes a method for automatically lubricating a device prior to insertion into a respiratory opening of an individual, the method comprising: providing a device that includes a working portion at a distal portion of a shaft, where the working portion and the shaft are configured for positioning within a body passageway of the individual, where a proximal portion of the shaft comprises a lubrication housing; advancing a lubrication housing distally along the shaft, wherein movement of the lubrication housing automatically lubricates the shaft; removing the lubrication housing from the shaft and the working portion such that the shaft and the working portion are lubricated; and inserting the working portion and shaft within a natural respiratory opening of the individual by advancing a working portion of the device within a body passageway of the individual.

In one variation the of the method advancing the lubrication housing causes at least one piercing member within the lubrication housing to puncture a lubrication supply. In an additional variation, the working portion of the device further comprises a distal opening fluidly coupled to a first lumen and a medial opening fluidly coupled to a second lumen; drawing suction through the distal opening while moving the working portion within the body passageway and maintaining suction for a period of time; determining whether the body passageway is drawn against the distal opening by the suction; ventilating the individual through the first lumen after failing to determine that the body passageway is drawn against the distal opening; and ventilating the individual through the second lumen after determining that the body passageway is drawn against the distal opening and maintaining suction while ventilating through the second lumen.

The present disclosure also includes devices for ventilating an individual through a body passageway. For instance, the device can include a tubular member having a proximal portion and a distal portion configured for insertion into the body passageway; a lubrication housing slidably positioned on the proximal portion of the tubular member, wherein movement of the lubrication housing along the tubular member causes application of a lubrication from the lubrication housing to the tubular member; and wherein the lubrication housing is removable from the tubular member.

In another variation, the device can be configured such that movement of the lubrication housing causes at least one piercing member within the lubrication housing to puncture a lubrication supply containing the lubrication. Variations of the device include a lubrication housing having a lever arm pivotally coupled to an interior of the lubrication housing, where the at least one piercing member is located on the lever arm.

The present disclosure also includes methods of determining a contraction of a heart in an individual. For example, such methods can include determining contraction of the heart by use of a trachea or an esophagus of the individual. For instance, such methods can include inserting a working portion of a ventilation device within a natural respiratory opening of the individual, where the ventilation device comprises a pressure detecting lumen in fluid communication with a pressure sensor, where the pressure detecting lumen is positioned along the working portion; positioning the pressure detecting lumen within a body passageway; monitoring a change in a pressure of the body passageway using the pressure detecting lumen and pressure sensor; tracking an electrical activity of the heart to determine an electrical cardiac signal of the heart using a heart monitoring device; and determining the contraction of the heart upon finding an association in the change in the pressure of the body passageway with the electrical cardiac signal of the heart.

The method can further include providing a signal upon determining a change in the pressure of the body passageway. The signal can comprise an electronic signal is electronically transmitted to the heart monitoring device. Alternatively, or in addition, the signal can comprise an audio signal or a visual signal for permitting a caregiver to correlate the signal with the electrical activity to determine the contraction of the heart.

The present disclosure also includes devices for ventilating an individual through one or more body passageways using a suction source and a gas supply. For example, the devices can include a tubular member having at least a first lumen and a second lumen, where the first lumen is fluidly coupled to a first opening located towards a distal portion of the tubular member, the second lumen fluidly coupled to a medial opening being located proximally to the first opening along a wall of the tubular member, where the first opening and medial opening are fluidly isolated within the tubular member; a mask slidably coupled on the tubular member; an extension portion located proximal to the mask, the extension portion having a loop shape such that a length of the distal portion extending distally from the mask can be adjusted by adjusting a size of the loop shape; a control system having a valve configured to fluidly direct the gas supply through either the first lumen or the second lumen; the control system being configured to direct a suction from a suction source through the first opening and first lumen and to identify a formation of a seal at the first opening resulting from the suction; where the control system ventilates the individual through the first lumen if the seal at the first opening is not identified and ventilate the individual through the second lumen while maintaining suction through the first opening if the seal at the first opening is identified.

The system and methods described herein can be compatible with devices that monitor the concentration or partial pressure of carbon dioxide ($CO_2$) in the respiratory gases (capnography). Primarily such devices are monitoring tool for use during anesthesia and intensive care that monitor expiratory $CO_2$ are of interest when rebreathing systems are being used. The ability to integrate the ventilation systems described herein with such capnography systems allows for improved patient care. Furthermore, the systems and methods described herein can be compatible with equipment found in emergency vehicles such as oxygen supplies and/or power supplies. In some variations, the system of the present disclosure can also provide audio or even video (through use of a display screen) instructions to ensure proper operation in those situations where the system may be used by first responders that are not trained emergency personnel.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Also, for purposes of clarity, certain features of the invention may not be depicted in some of the drawings. Included in the drawings are the following figures:

FIG. 8B provides a component listing for the schematic of FIG. 8A.

FIG. 8C shows a listing of various modes for the system.

FIGS. 9B to 9C show a partial isometric view and partial cross-sectional views of the mask and trigger used to close the system and initiate manual ventilation.

FIGS. 13-22 illustrate an example of the circuitry for sensing the phase, rate, depth and effectiveness of a chest compression with a resistor placed on the tube of an airway placed in the patient's mouth, trachea or esophagus.

DETAILED DESCRIPTION OF THE INVENTION

Before the devices, systems and methods of the present invention are described, it is to be understood that this invention is not limited to particular therapeutic applications and implant sites described, as such may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The terms "proximal", "distal", "near" and "far" when used indicate positions or locations relative to the user where proximal refers to a position or location closer to the user and distal refers to a position or location farther away from the user.

Figure 1:
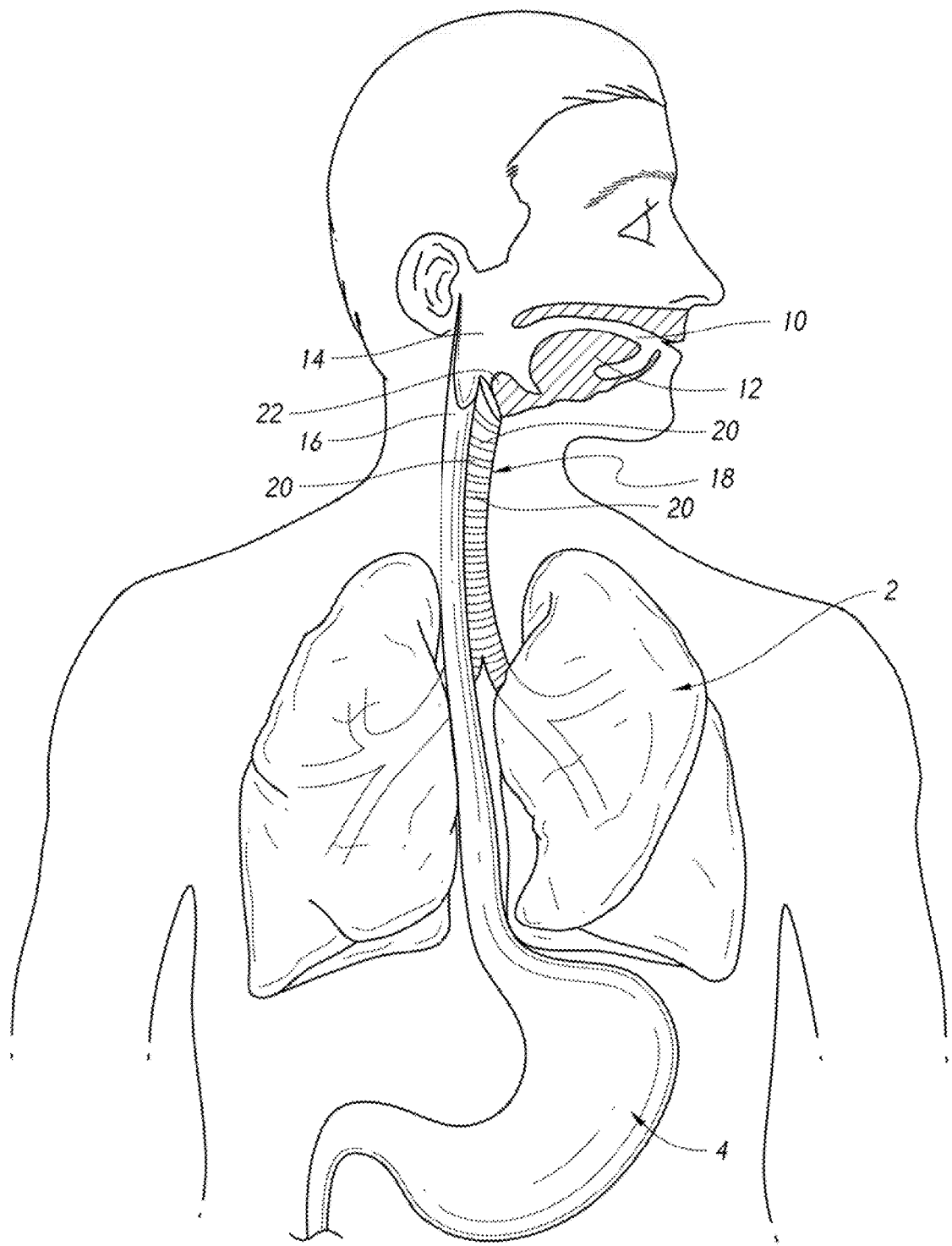
FIG. 1 provides a partial view of a patient's oral cavity, tongue, pharynx as well as esophagus and trachea.
Figure 2:
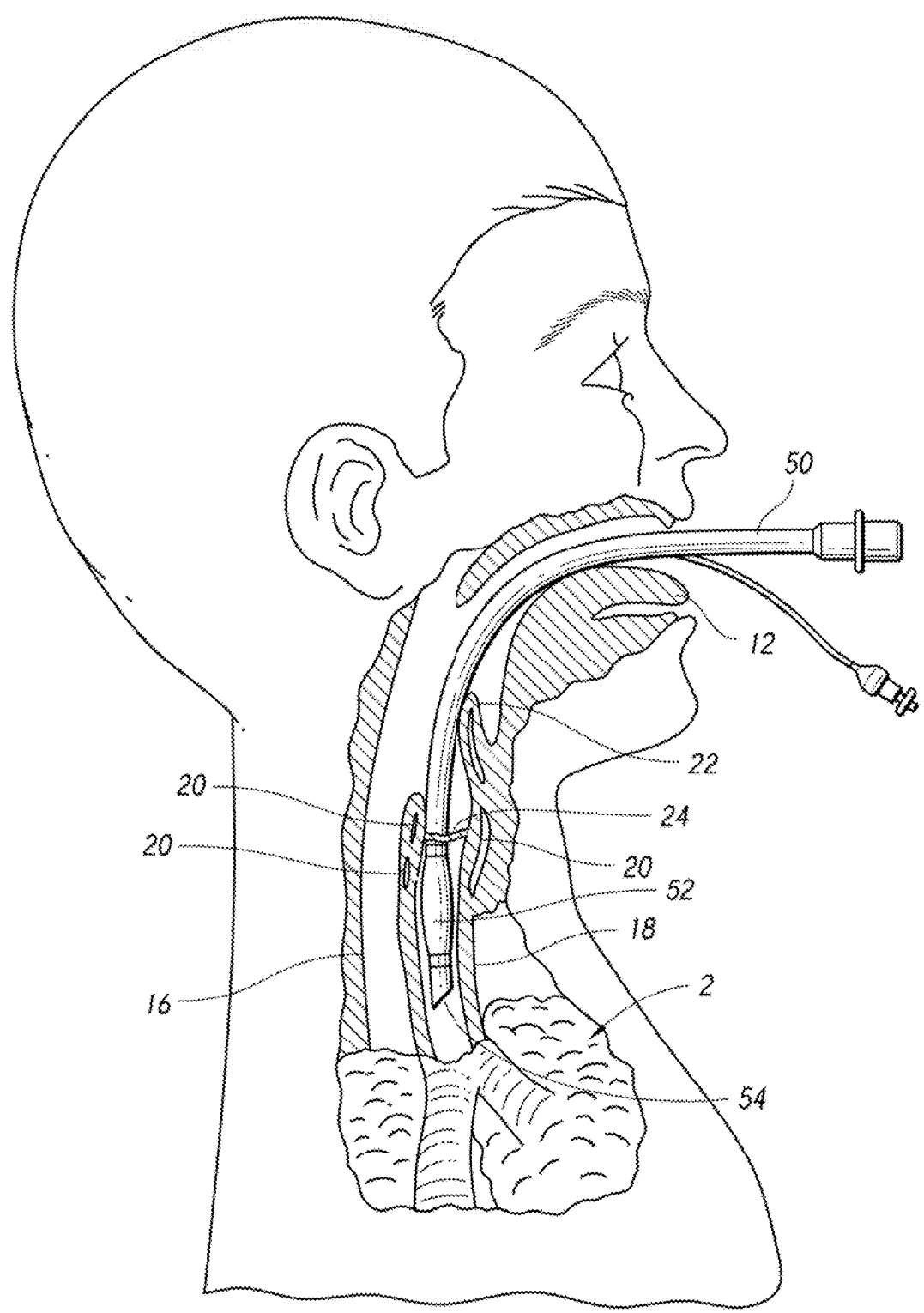
FIG. 2 illustrates one example of a conventional device as used to intubate a patient.
Figure 3A:
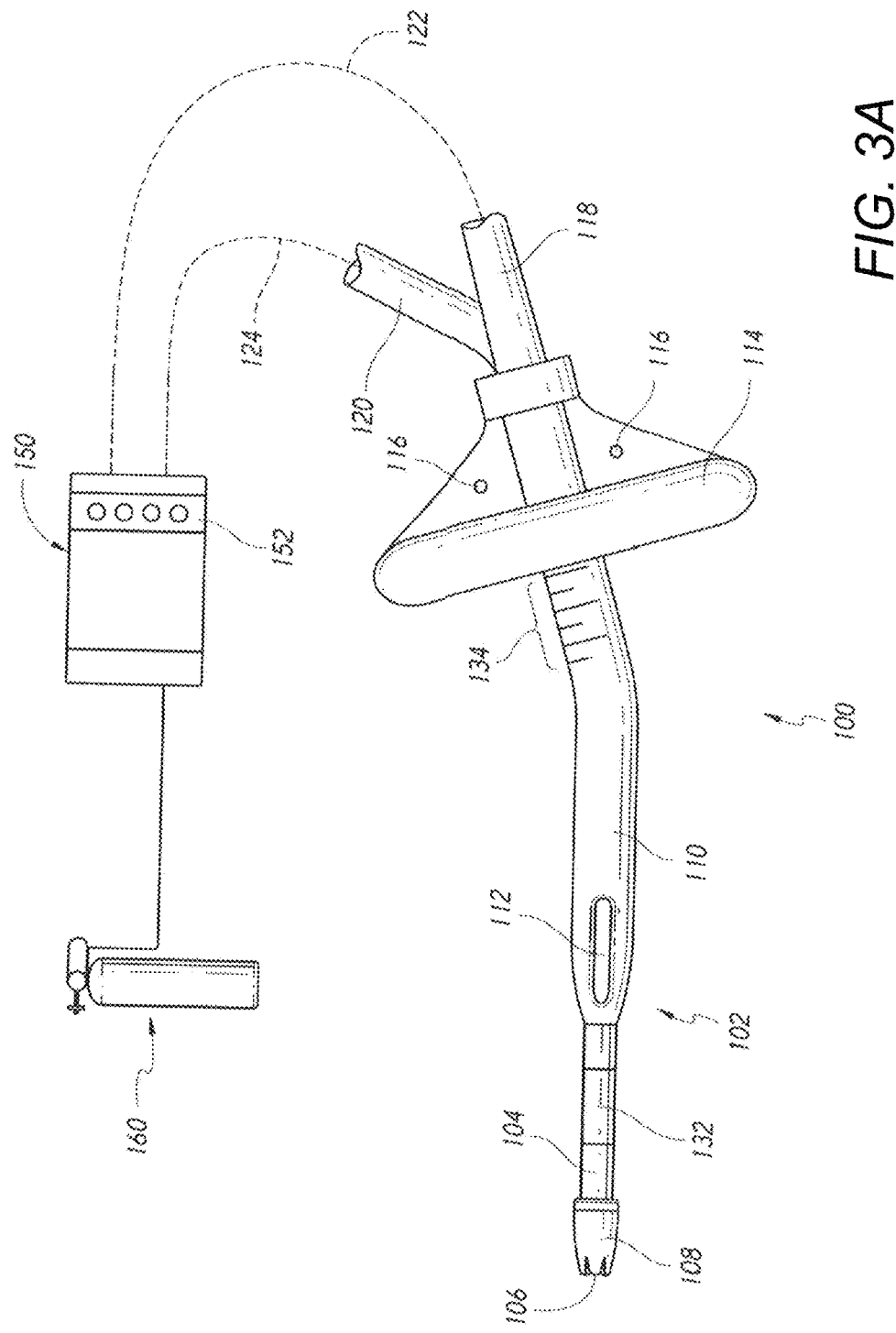
FIG. 3A illustrates various components of an example of an improved ventilation system.

FIG. 3A illustrates various components of an example of an improved system according to the present disclosure. As shown, the ventilation device 100 includes a working end 102 that is inserted into a patient. The working end can include a distal tubing 104 that contains a first lumen (not shown), which extends through a distal opening 106 of the ventilation device 100 and is in fluid communication with a control unit (also called a ventilator) 150 and/or supply source 160 via one or more proximal tubes 118. The control unit 150 can also include an apparatus designed to provide suction as well as a collection canister. In operation, the control unit 150 directs suction or applies a vacuum through a first fluid path 122, which in turn causes a suction or negative pressure at the distal opening 106. The source 160 can comprise oxygen, air, or any other gas that is desired for ventilation of delivery into the lungs. The source 160 can be nested within physical construct of the controller 150. However, the source 160 can be optional so that the controller ventilates the patient only using ambient air.

The control unit 150 maintains the device 100 in this state for a set period of time and monitors the parameters of the pressure or flow parameters within the first lumen to determine whether to ventilate through the first or second. The example illustrated in FIG. 3A also includes a hub 108 with one or more features that aid in proper functioning of the device. Such features are described in detail below. Furthermore, the distal opening 106 can include any number of ports at the distal end of the device so long as the ports are in a fluid path with the first lumen. Likewise, the medial opening 112 can comprise any number of openings as long as those openings are in fluid communication with the second lumen. In addition, variations of the device can also be inserted through a nasal opening rather than a mouth.

The ventilation device 100 further includes a proximal tubing 110 that houses a second lumen (not shown) that exits the device 100 at a medial opening 112. As discussed below, distal opening and first lumen are fluidly isolated from the medial opening and second lumen through the working end of the device 102 to the control unit 150. This fluid isolation allows the control unit 150 to determine which lumen to use to ventilate the patient. The control unit directs flow through a second fluid path 124 that is fluidly coupled to the second lumen and medial opening 112 when the device is positioned in the esophagus 16 rather than the trachea 18.

The ventilation system 100 illustrated in FIG. 3A also shows an optional mask 114 with optional venting ports 116. Variations of the system can include alternate configurations without a mask or with other such devices such as a mouth guard or any other commonly used mounting apparatus. As discussed below, the mask 114 or other mounting apparatus can be used to assist the caregiver in properly orienting the device 100 as it is inserted into the patient. Variations of the device can include a balloon, sponge or any other structure that secures the proximal region of the device to the patient to ensure that gas is directed to the lungs during inhalation. The mask (or other structure as described herein) can include a securing band, tape strip, or temporary adhesive to secure the mask in place on the patient. The mask or similar feature can be used to determine how far to advance the working end 102 into the patient. Alternatively, or in combination, the device 100 can include graduated markings 134 to assist the caregiver in properly advancing the device into the patient. The mask can be slidable to adjust the length from the mask to the distal or proximal opening.

FIG. 3A also shows a representative figure of a control system 150 with a number of controls 152 that allow for various device operative sequences, manual controls, or device overrides. For example, the system 150 can include manual ventilation controls so that the caregiver can manually adjust inspiration and expiration of the patient. The controls 152 can include a reset or rapid ventilation mode for performing cardiopulmonary resuscitation. The controls 150 include a continuous airflow or continuous vacuum mode that can assist in clearing debris or bodily fluids from the body passages. The controls also allow caregivers to connect the device 100 directly to an endotracheal tube if the caregiver decides to intubate. In an additional variation, the system can allow for active ventilation consisting of blowing for a period and then sucking for a period through the active lumen in order to increase ventilation efficiency. In some variations, the system is configured so that the ventilation openings, as well as other openings on the tube do not rotate relative to the mask so that caregiver can align the openings with the trachea.

The device shown in FIG. 3A can also include one or more electrodes positioned on the working end. For example, the hub 108 can serve as an electrode and apply electricity to the heart in order to defibrillate a patient out of an irregular rhythm or increase the heart rate or contractility. Additionally, one or more electrodes can be inserted on or embedded in a tube designed to be placed in the patient's mouth, esophagus or trachea. Such placement will be beneficial because it would allow the operator a more direct route of electrical stimulation of the heart compared that the current use of pads placed on the patient's chest. A tube placed in the esophagus would more easily be able to detect a pulse because of the major arteries running parallel to the esophagus. This would allow rescuers to determine a pulse without having to touch the patient. It would also allow an untrained bystander to administer CPR, when that bystander might not be trained on checking for a pulse in the patients. In addition, the pressure sensors, as described below, can be placed on the tube that had been advanced into the patients mouth that may be pressing against major arteries would be able to detect if there was a change in pressure.

In additional variations, the control system 150 can be integrated into one or more parts of the device body 102 rather than being a separate stand-alone box type configuration. In addition, the ventilation system 100 can be optionally configured to work with a defibrillator. Alternate variations of the system 100 can be configured to provide an audible, visual, or tactile sensation to indicate when a caregiver should administer chest compressions. In an alternate variation, the control system 150 can be include a ventilation bag, such as those used in bag-valve masks (BVM). This configuration enables a completely disposable system that uses the compression and recoil of the bag to drive both the ventilations and the vacuums. This bag could be placed on the chest of the patient during CPR to time the ventilations with chest compressions. The distal tubing of the device would still operate both in the trachea and the esophagus using a control system to automatically determine its locations and effectively isolate the lungs from the stomach in either position.

FIG. 3A also shows the depicted variation of the device 100 as having an optional balloon 132 or other expandable member located on a working end. When used, the balloon can be positioned anywhere along the device adjacent to the distal opening 106. Alternatively, or in combination, a balloon can be located adjacent to the medial opening.

The various tubing forming the device 100 should be sufficiently flexible so that the device can be navigated through the upper respiratory system. Alternatively, or in addition, portions of the tubing can be constructed to withstand being collapsed by the patient's mouth or teeth. In additional variations the system 100 can be designed such that the distance between the distal opening 106 is adjustable relative to the medial opening 112 and/or the mask 114 (or even moveable relative to the gradations 134). A similar variation includes a medial opening 112 that can be adjustably positioned relative to the distal opening 106, mask 114 and or gradations 134.

Figure 3B:
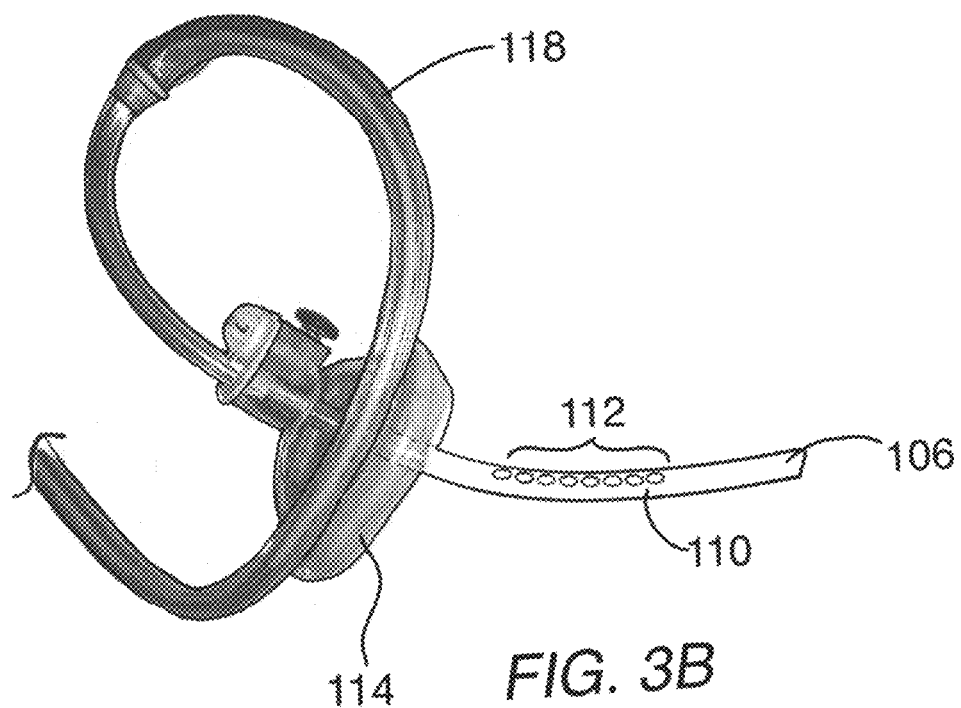
FIGS. 3B and 3C illustrate an additional variation of a device where a mask is adjustable along a length of the tubing.
Figure 3C:
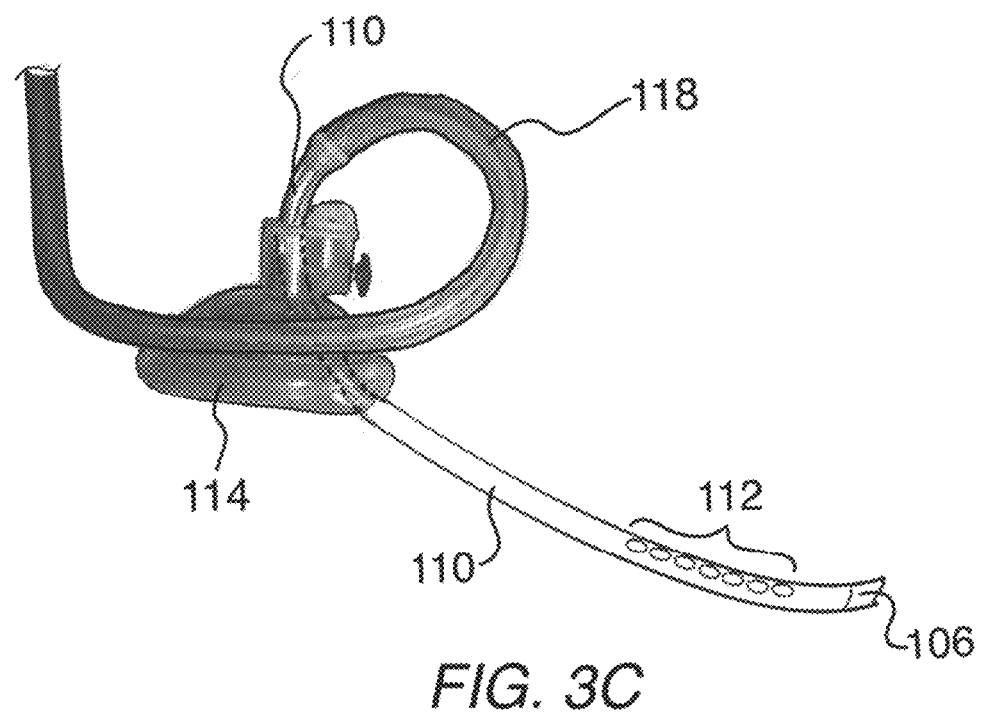

FIGS. 3B and 3C illustrate an additional variation of a device 100 where a mask 114 is adjustable along a length of the tubing 110. This permits an adjustable length of distal tubing 110 to accommodate a variety of patient sizes. The illustrated variation also shows airway tubing 110 and extension tubing 118 proximal to the mask forming an adjustable loop. In some cases, having an adjustable tube length with a slidable mask 114 creates a leverage arm when the airway tube extends proximally from the mask for smaller patients. The material of the airway tubing 110 is often is not as flexible as the material of the extension tubing 118. In such a case, if a lateral pressure is applied to airway tube that is extended out of the mask, the airway could to move or twist dramatically. The adjustable loop which includes both the airway tubing and the extension tubing. This loop wraps the tubing back towards the mask to reduce any mechanical leverage that would otherwise be applied to the mask/distal tubing. FIG. 3B illustrates a configuration used for smaller individual where a shortened length of the airway tubing 110 extends from the mask 114 (e.g., the mask 114 is advanced towards the distal end of the tubing). This increases the size of the loop proximal to the mask 114, which reduces the mechanical leverage that would otherwise be applied by the tubing proximal to the mask. FIG. 3C illustrates the airway tubing 110 extended from the mask 114 which reduces the size of the loop proximal to the mask 114.

FIGS. 3B and 3C also illustrate a variation of the device having a plurality of medial openings 112 with a distal opening 106 extending out through the end of the tubing. Additionally, the extension tubing/proximal tubing 118 comprises a single multi-lumen tube that, as discussed below, includes a multi-lumen configuration to accommodate the first and second lumens that are coupled to the distal and medial openings.

Figure 3D:
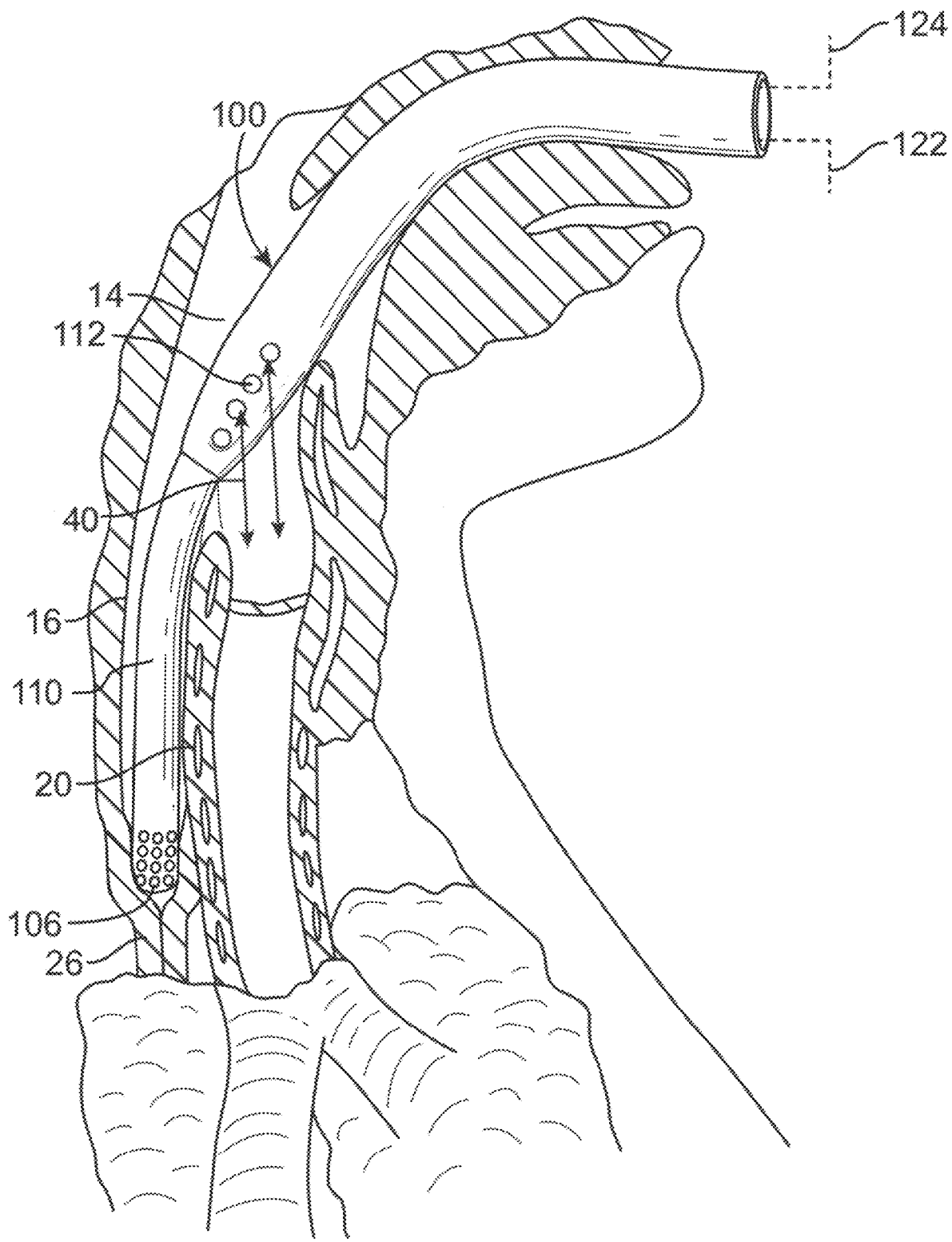
FIG. 3D shows a variation of a device that draws suction while being inserted to automatically size the device for patients.

Use of the ventilation device requires properly sizing a length of the tubing 110 that extends from the mask so that the anterior openings/medial openings 112 to align the opening of the trachea into the larynx. Typically, this is performed by adjusting the length of the tube by sliding the mask along the length of the tube to determine insertion depth. As shown in FIG. 3D, variations of the device can include multiple distal openings 106 that extend over a circumference of the distal end of the device 100. During insertion, the tubing 110 is advanced through the oralpharnyx while suction is drawn through the openings 106.

As the distal end enters the esophagus, the esophagus collapses to seal the distal openings 106. This ensures that the tube 110 is placed in the same anatomical position in all patients. Additional medial openings 112 (as shown in FIGS. 3B and 3C) can be added to the tubing 110 to ensure the distal end travels to the proper depth is the esophagus before a complete seal can occur. Once the distal end is properly positioned within the collapsed esophagus, the mask can be slid to sit on the patient's face or balloons can be inflated to seal the upper airway.

Figure 3E:
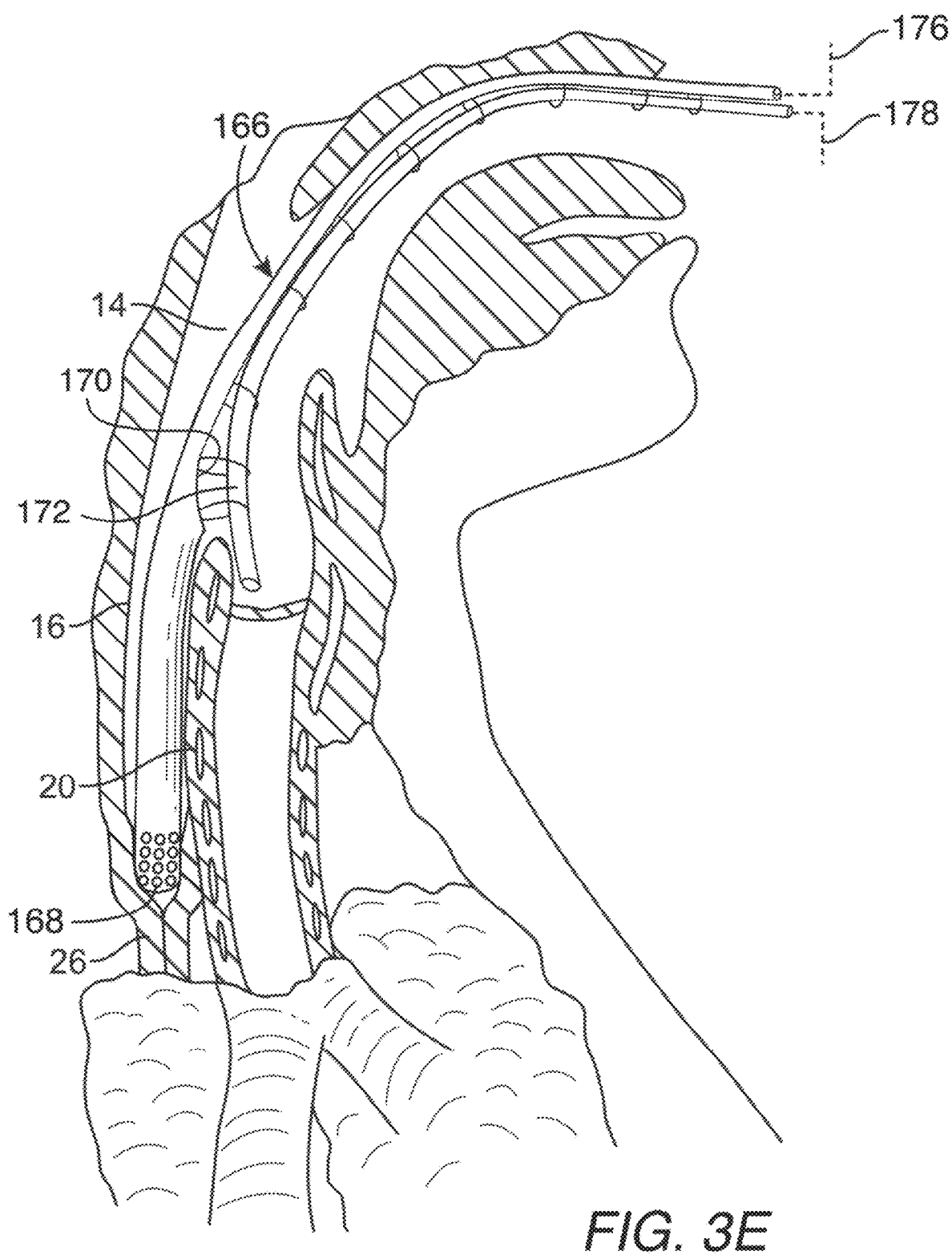
FIG. 3E illustrates use of the features described above to aid in placement of a conventional ventilation tube 172.

FIG. 3E illustrates use of the features described above to aid in placement of a conventional ventilation tube 172. In this variation, a guide device 166 includes a plurality of suction openings 168 at a distal end. As noted above, the guide device 166 can be advanced into the esophagus while applying suction such that the esophagus collapses about the openings 168. This allows for positive determination of the location of the guide device 166. The guide device 166 can include the ventilation tube 172 or the ventilation tube 172 can be advanced along a track 170 of the guide device 166 when properly positioned. In some variations, the creation of a seal at the distal openings 168 can also cause the endotracheal tube to be released. If the device 166 is inserted into a trachea, location of the device can be determined by lack of seal formation as well as insertion depth (via markings or other measurements).

FIGS. 4A to 4D illustrate partial views of an airway unit or working end 102 of a ventilation device 100 as described herein.

Figure 4A:
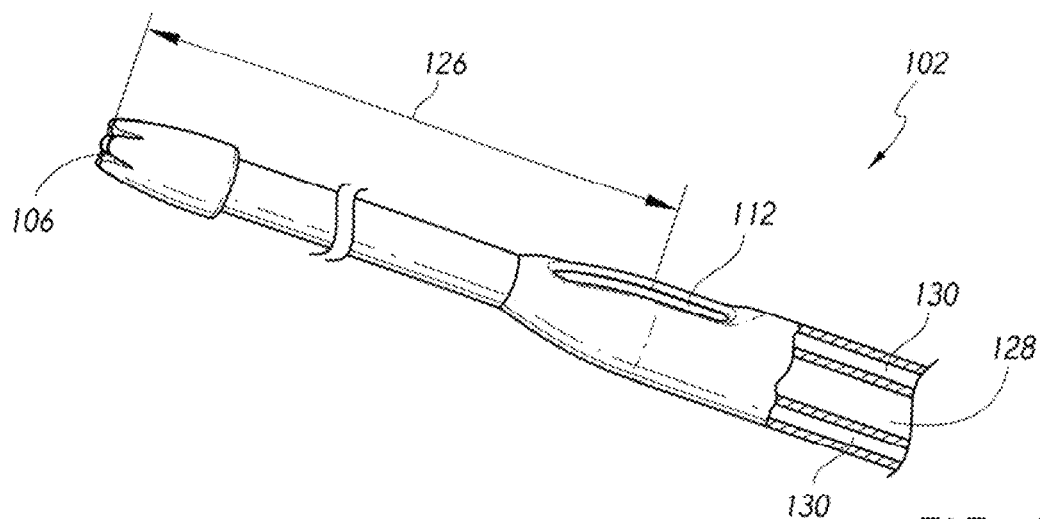
FIGS. 4A to 4D illustrate a partial sectional view of a working end of an improved ventilation device.

FIG. 4A illustrates a first lumen 128 that is fluidly coupled to a distal opening 106 and a second lumen 130 that is fluidly coupled to the medial opening 112 where the first and second lumens 128 and 130 are fluidly isolated from each other as described above. FIG. 4A also illustrates that the spacing 126 between the distal opening 106 and the medial opening 112 can be selected based on the intended patient. For example, since the medial opening 112 is intended to be positioned in or around the pharynx when the distal opening 106 is positioned in the esophagus or trachea, the spacing 126 can be selected for an individual of average build. In most cases, the working end 102 of the ventilation device 100 will comprise a single use disposable component. Accordingly, the ventilation device 100 can include a number of disposable components having different spacing 126 between the medial 112 and distal 106 openings. For instance, the varying spacing can accommodate infants, toddlers, young children, as well as various body sizes.

Figure 4B:
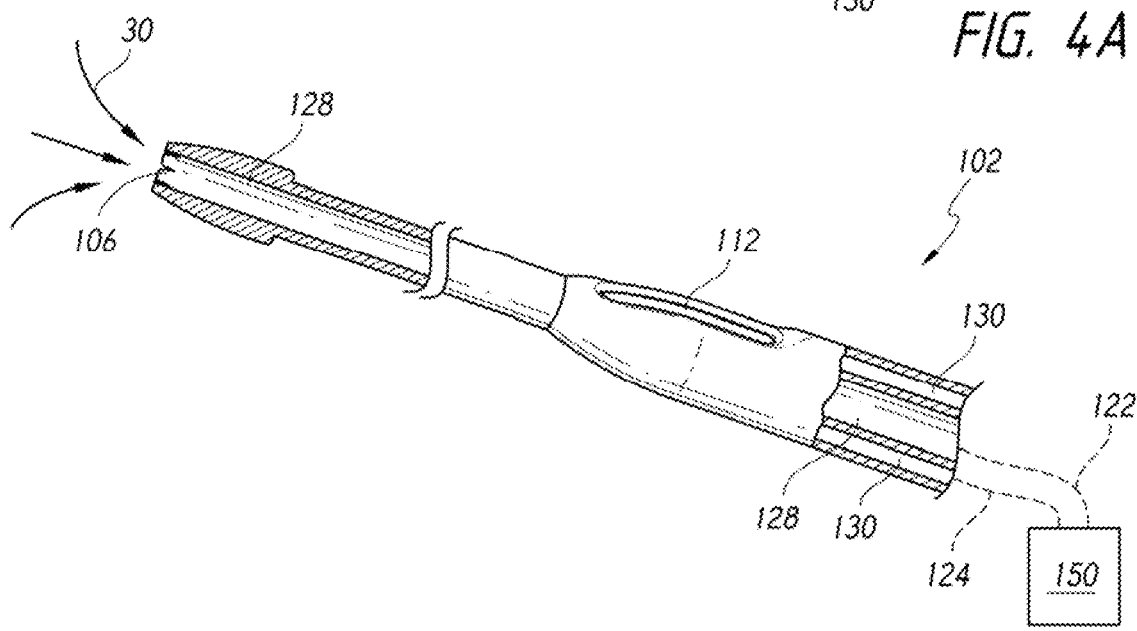

FIG. 4B illustrates a partial cross-sectional view of the working end 102 of the ventilation device of FIG. 4A. Once the device is properly positioned within the patient, the control unit 150 applies a suction or vacuum through a first fluid path 122, then through the first lumen 128 and ultimately causing a vacuum at the distal opening 106 as denoted by arrows 30. In additional variations, the operator or caregiver may choose to clear food or other debris from the patient by delivering air through the first lumen 128 or by attempting to use the suction at the distal opening to remove particles or other bodily fluids. The system 150 shall continue to pull a vacuum through the first lumen 130 for a period of time. If the device 100 is properly positioned within the trachea (as discussed below), the system 150 will begin to ventilate through the first lumen 128. In other words, the system 100 will begin to cyclically deliver oxygen or other gas from the source 160 and remove carbon dioxide from the patient to properly ventilate the patient's lungs. In this situation, flow is not required through the second lumen 130 and medial opening 112. Although FIG. 4B shows the first lumen 128 to be located within the second lumen 130 any number of variations can be used. For example, the lumens can be concentric or parallel. Additional variations even allow for the lumens to be in fluid communication where one or more valves determine whether ventilation occurs through the distal opening or through the medial opening. The device can include any number of safety checks to confirm placement of the device doesn't change. For example, once the device confirms placement in the trachea, it can re-perform a check to ensure that it is placed in the trachea over a pre-determined interval. Alternatively, it can perform this check on a sliding scale (e.g., $1^{st}$ check at 30 second, $2^{nd}$ check at 2 minutes, $3^{rd}$ check at 10 minutes, etc.). In an additional variation, the system is designed to provide a safety check to ensure that the suction filter is not clogged causing a misread of position. In such a case the device gives ventilation out the distal port once a vacuum is detected. This ventilation bolus can be small or large. By monitoring vacuum and determining if it is lost during the distal air bolus, the device knows that the seal was at the esophagus and resumes suctioning distally and ventilation through the proximal ports. If the vacuum is not lost during the distal air bolus the device can assume that the filter is clogged, and an error signal will indicate for the operator to replace the working end of the device or to check for obstructions.

The system 150 can comprise the mechanism that ventilates and produces suction or a vacuum. Generally, the system 150 is reusable (as opposed to the working end that is generally disposable). The system 150 can be portable, affixed to an ambulance or other emergency vehicle or build within a cart or room. Variations include battery powered devices, pneumatic powered devices, or devices that require a power source (such as an AC outlet).

Figure 4C:
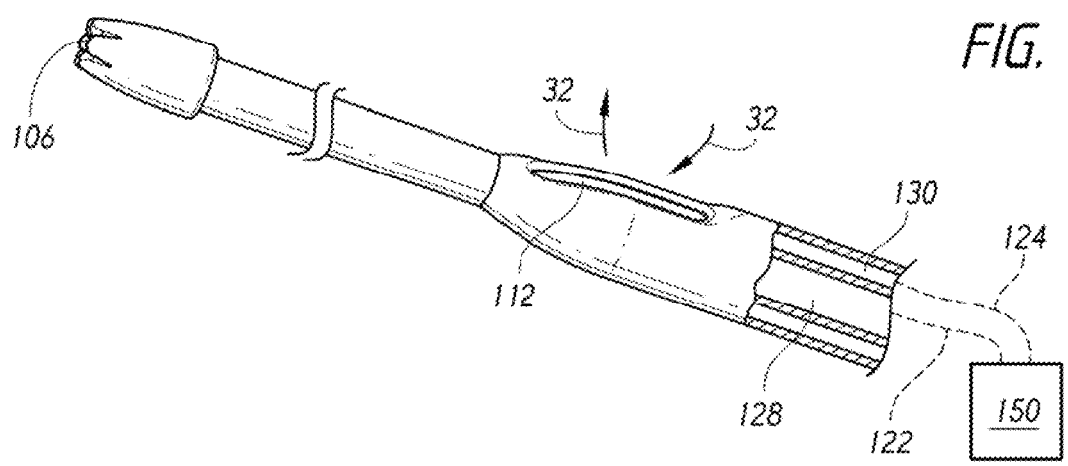

FIG. 4C illustrates the condition where the distal opening 106 is positioned within the esophagus. In this situation the control unit 150 directs ventilation through the second lumen 130. As shown by arrows 32, because the medial lumen 112 is fluidly coupled to the second lumen 130 ventilation 32 takes place at the medial opening 112.

Figure 4D:
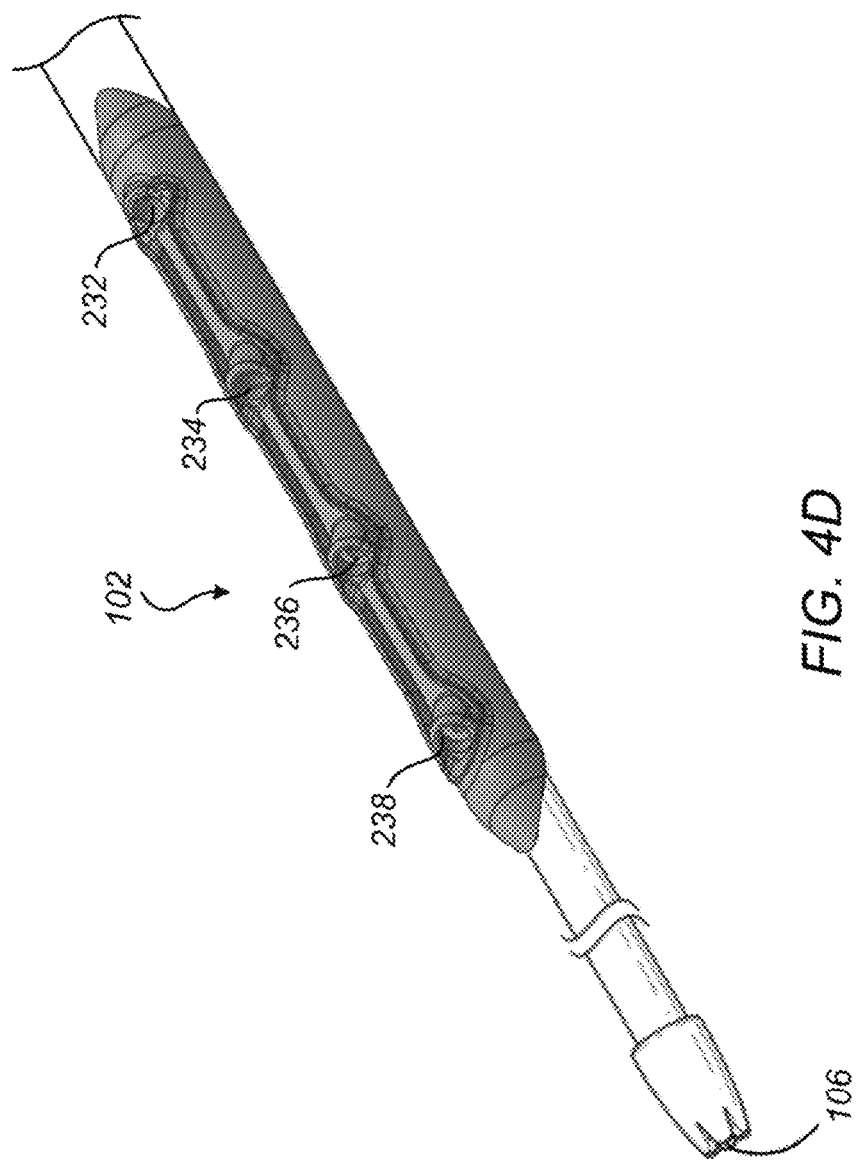

FIG. 4D illustrates another variation of a working end 102 where the device includes a plurality of medial openings 232, 234, 236, and 238. The proper depth sizing of supraglottic ensures that the lumens delivering the ventilation (e.g., lumen 128 shown above) are aligned with the opening of the larynx. The illustrated variation shows a supraglottic ventilation lumen that is increases the margin for error related to depth sizing to properly ventilate within a large sizing tolerance.

The ability to direct ventilated air into the larynx and therefore lungs while the opening of the ventilation lumens are covered by tissue is important. In FIG. 4D, the majority of ventilation is directed to the rear-most port 232. If this port 2332 is covered or blocked, ventilation is then directed to the next opening 234. This continues down all 4 openings ensuring the hole closest to the larynx receives the ventilation. In use, the system applies a negative pressure to the distal opening 106, which is fluidly separate from the proximal ventilation ports 232-238 described above. If all of the ports 232-238 are inadvertently placed distally of the larynx the system detects a negative pressure in the proximal ventilation lumen (e.g., 128) and triggers a warning to the care provider that the airway device has been inserted too deep (distal). The system can then instruct the caregiver to resize the airway device.

FIGS. 5A to 5E show a representation of the process of ventilating a patient using a ventilation device 100 as described herein.

Figure 5A:
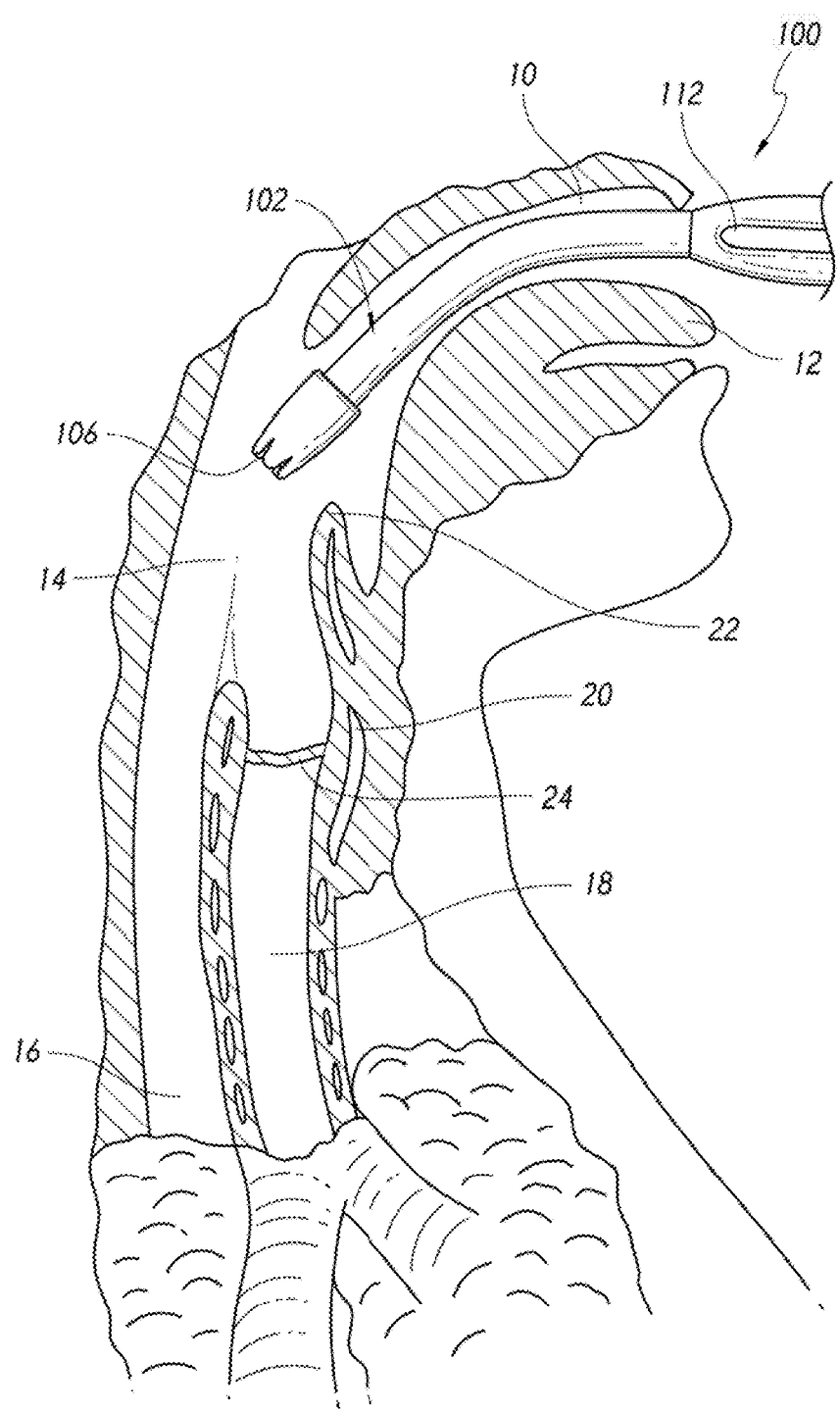
FIGS. 5A to 5E show a representation of the process of ventilating a patient using an improved ventilation device.

FIG. 5A illustrates the ventilation device 100 as a caregiver advances the device 100 into the oral cavity 10 over the tongue 12 and into the pharynx 14. At any time during the procedure, the caregiver can manually operate the device to suction fluids, food particles, or other items from the body. As described herein, the caregiver can "blindly" advance the working end 102 into the patient. As a result, the working end 102 will either end up in the esophagus 16 or trachea 18 of the patient.

Figure 5B:
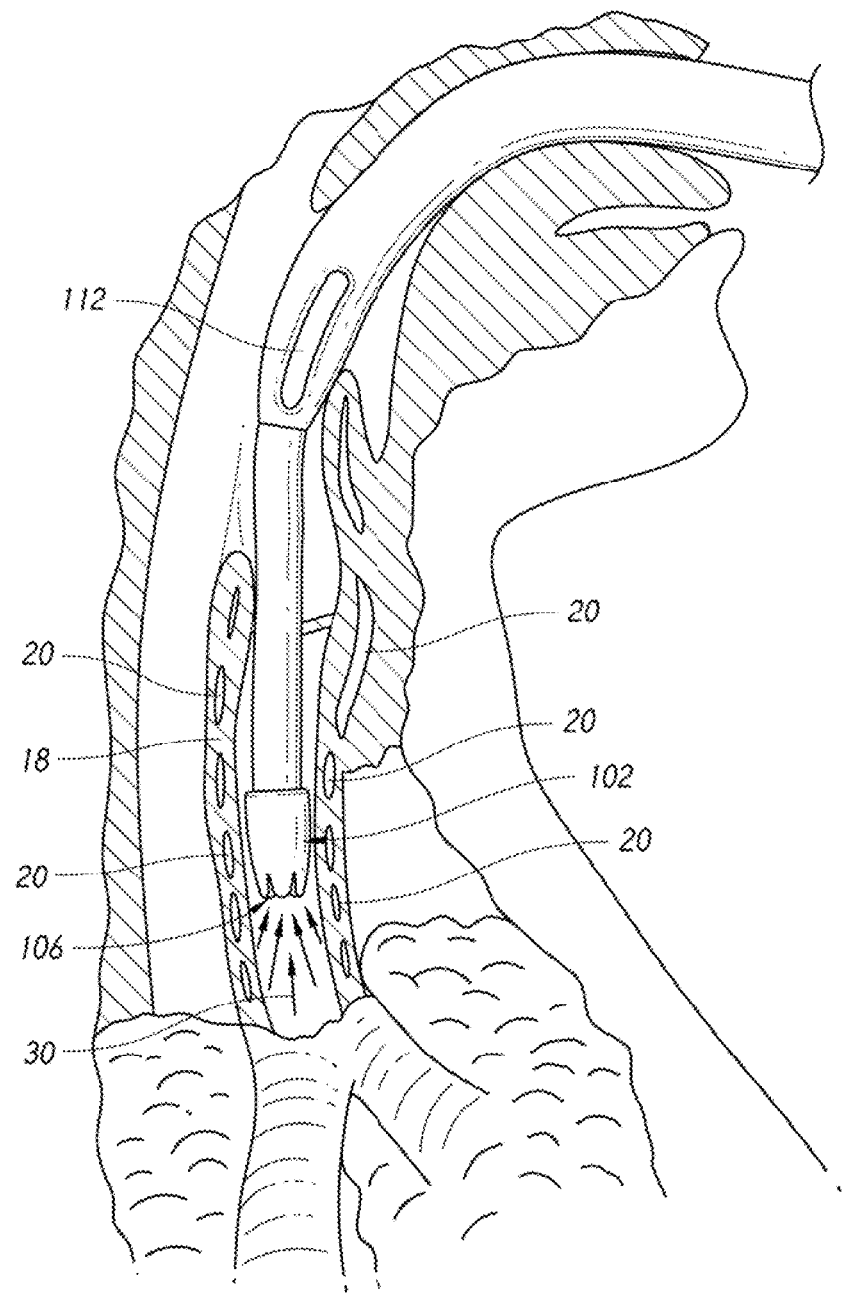
Figure 5C:
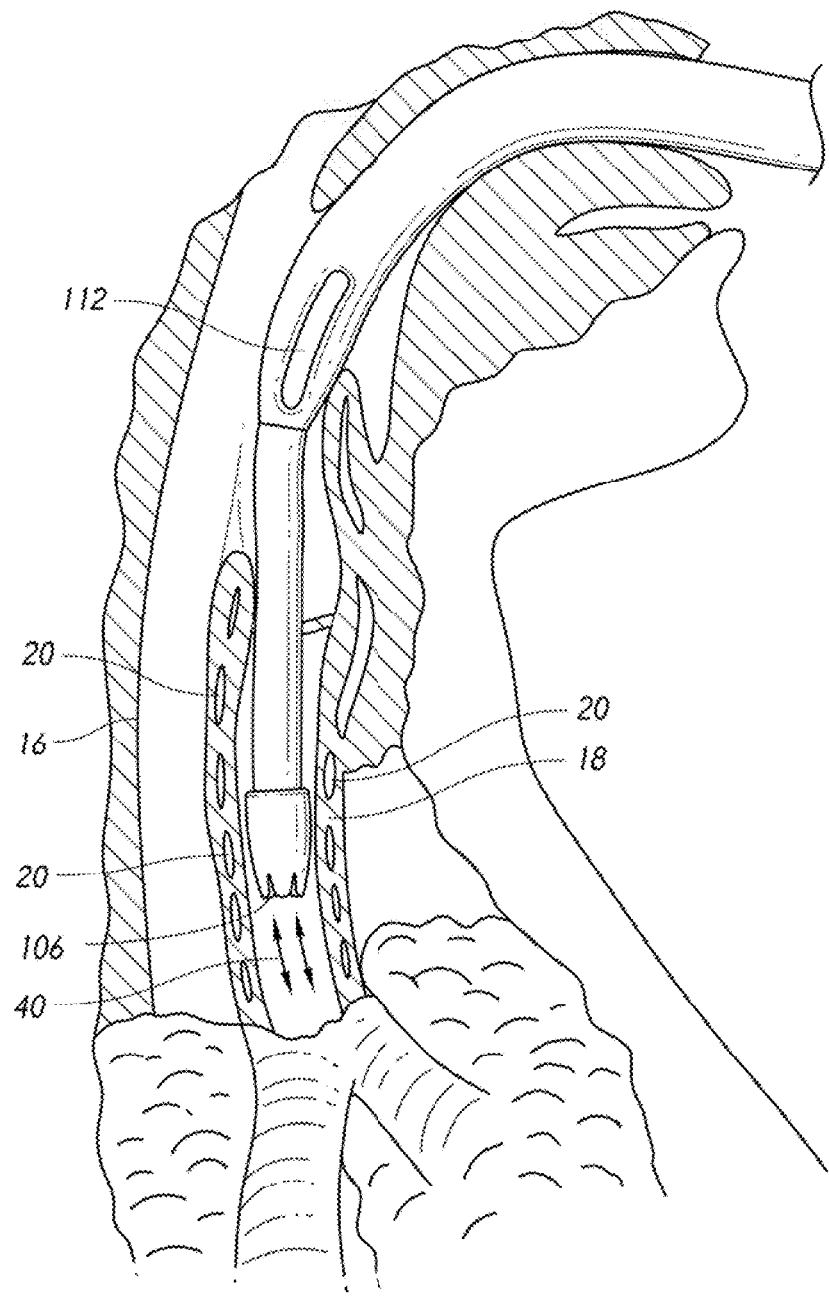

FIG. 5B illustrates the condition where the caregiver advances the working end 102 into a trachea 18 of an individual. Once the caregiver places the device 100, the caregiver can initiate the control unit 150 to start the process to determine placement of the device 100. Alternatively, one or more sensors on the device can automatically trigger actuation of the control unit. In either case, the control unit draws a vacuum through the distal opening 106 for a predetermined period of time. The vacuum reduces pressure and draws air within the distal opening 106. The control unit 150 then assess a state of the device by monitoring the vacuum, airflow, or any other fluid parameter that would indicate whether the walls of the body passage, in this case the trachea 18, collapsed causing the formation of a vacuum seal. In those cases, like FIG. 5B where the device is situated within the trachea, the suction 30 will have little effect on the walls of the trachea 18. As noted above, the walls of the trachea 18 are reinforced with rings of cartilage 20 that provide structural rigidity of the airway. Because the controller 150 will not detect the formation of a vacuum seal at the distal opening 106 (or within the first lumen) the system registers the distal opening 106 as being properly positioned in the trachea 18 (rather than the esophagus 16) and, after a pre-determined period of time (e.g., 10-15 seconds), the controller 150 ceases to draw a vacuum and begins to ventilate the patient's lungs by alternating between delivery of the gas from the gas supply 160 and removing carbon dioxide. As a result, the first lumen is used as a ventilation lumen. It will be important for the controller 150 to differentiate changes in vacuum or flow that result from suctioning of fluids or debris. In some variations of the device, the controller 150 is configured to identify formation of a seal when the vacuum builds or flow drops to a sufficient degree such that the device has formed a vacuum seal rather than suctioned fluids or a substance.

The control unit 150 can determine whether or not a seal is formed by measuring strain on a suction motor (or similar apparatus such as a venturi device that produces a vacuum) that causes the negative pressure within the main lumen for suction. If the control unit 150 observes zero or minimal strain on the suction motor after a pre-determined time, then the control unit 150 will use the first lumen as the ventilation lumen.

Figure 5D:
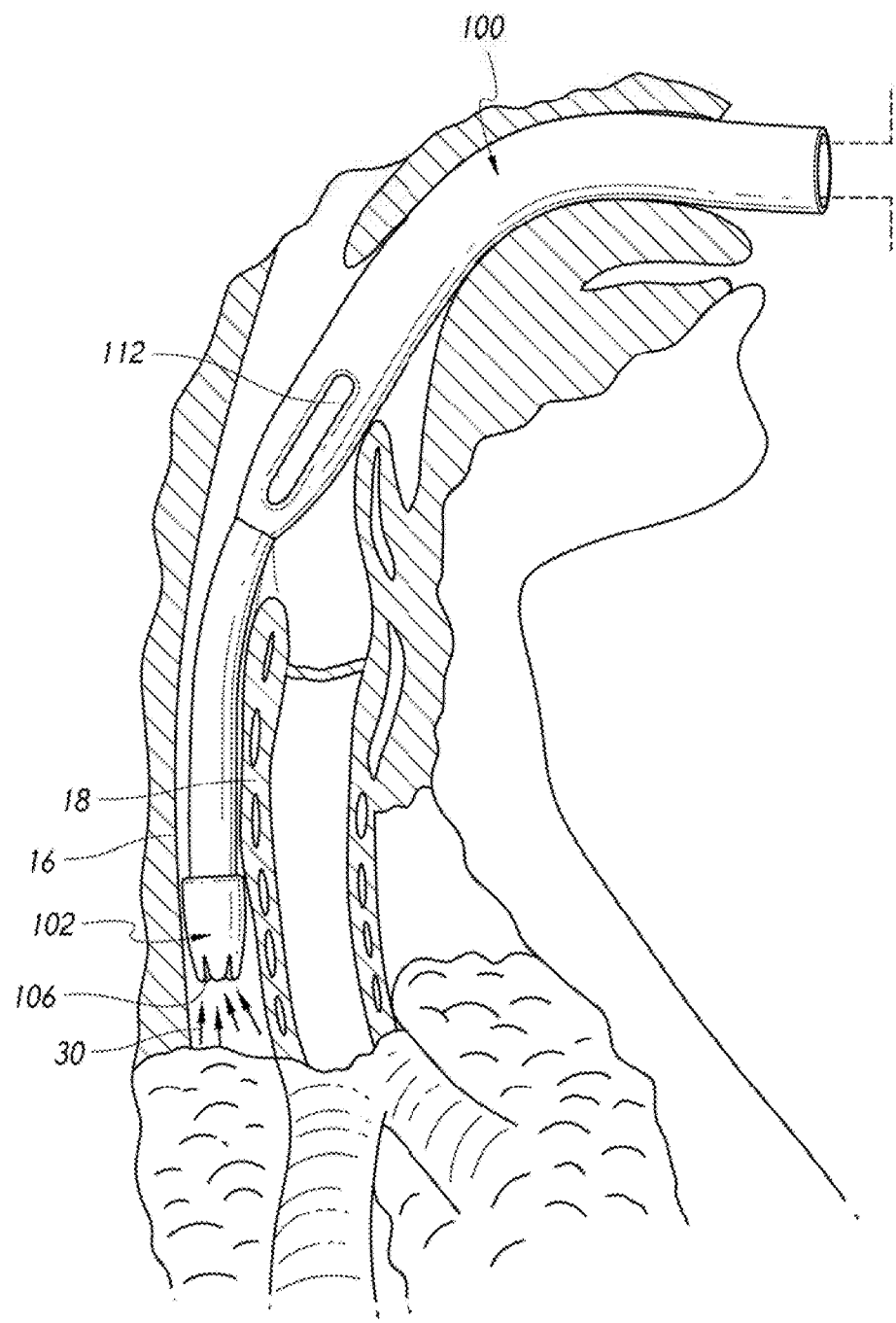

FIG. 5D illustrates a state where the caregiver advances a working end 102 of the ventilation device 100 into an esophagus 16 rather than the trachea 18. Similarly to the state depicted by FIG. 5B above, once the caregiver positions the device 100, the caregiver can initiate the control unit 150 to start the process to determine placement of the device 100. As noted above, additional variations of the device and system can include one or more sensors that can automatically trigger actuation of the control unit.

Figure 5E:
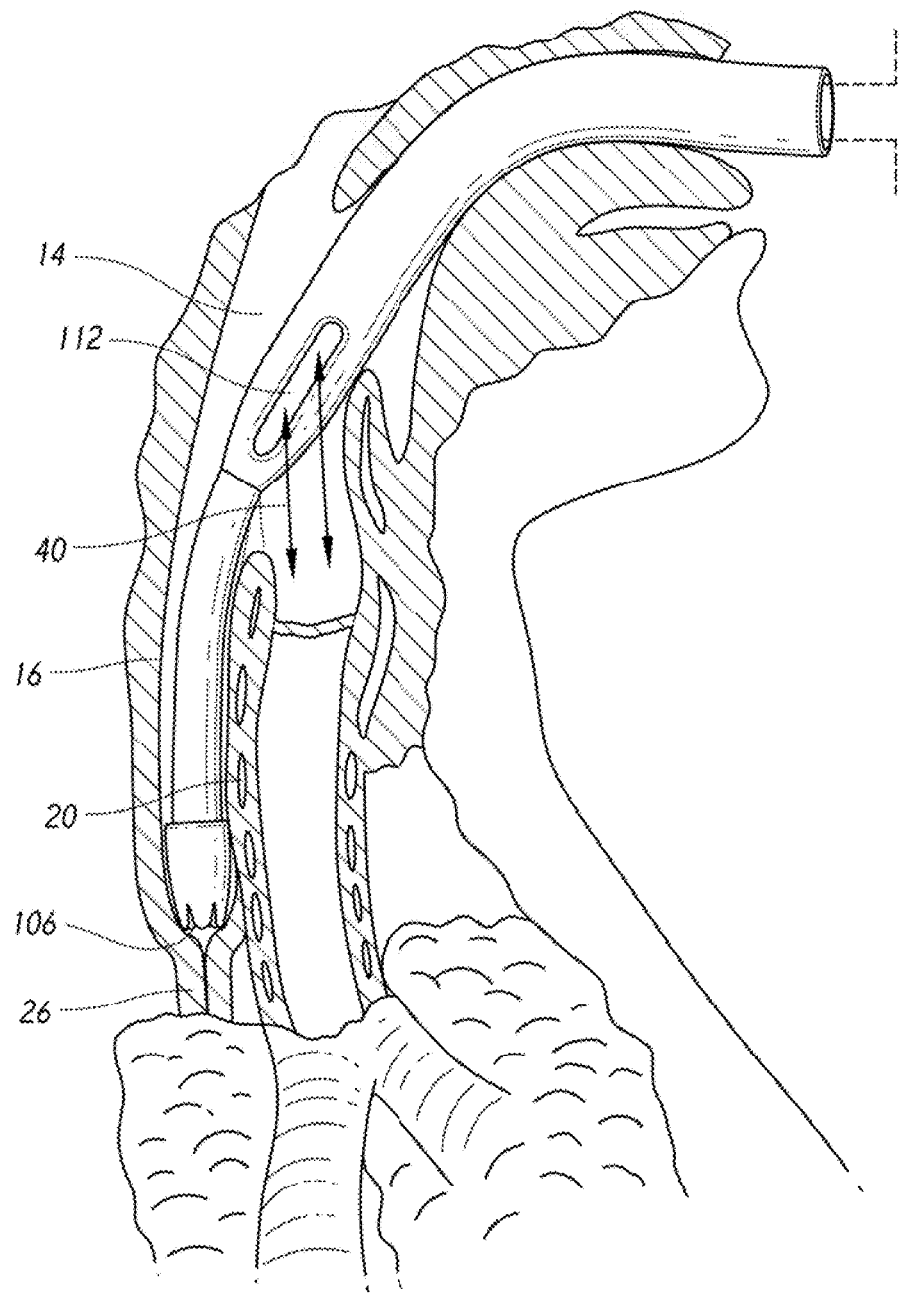

FIG. 5D depicts the state where the control unit 150 pull vacuum through the distal opening 106 for a predetermined period of time. The vacuum reduces pressure and draws air within the distal opening 106. The control unit 150 then assess a state of the device by monitoring the vacuum, airflow, or any other fluid parameter that would indicate whether the walls of the body passage, in this case the esophagus 16 collapsed. As shown, the walls partially or totally collapse resulting in formation of a vacuum seal at the distal opening 16. As noted above, muscles form the walls of the esophagus 16. There is no reinforcing structure in the esophagus as opposed to the cartilage rings in the trachea 18. The control unit can be configured to monitor the formation of a vacuum seal and if the seal remains for a predetermined period of time, the control unit 150 directs ventilation 40 in and out of the medial opening 112 as depicted in FIG. 5E. As shown and discussed above, the spacing between the distal opening 106 and medial opening 112 can be selected such that the medial opening remains in or near the pharynx 14. However, variations of the device permit the medial opening to enter the esophagus 16 so long as the opening 112 can continue to ventilate the patient.

Because the control unit 150 will not detect the formation of a vacuum seal at the distal opening 106 (or within the first lumen) the system registers the distal opening 106 as being properly positioned in the trachea 18 (rather than the esophagus 16) and, after a pre-determined period of time, the control unit 150 ceases to draw a vacuum and begins to ventilate the patient's lungs by alternating between delivery of the gas from the gas supply 160 and removing carbon dioxide. In this situation the device uses the second lumen as a ventilation lumen. One additional benefit of positioning the working end 102 of the device 100 within the esophagus 16 is that the vacuum seal produces an anchoring effect that maintains the device in position. This feature eliminates the need to secure the mask or other feature about the patient's head, neck or face. In addition, if a caregiver inadvertently pulls the device 100 while a seal is formed, the vacuum seal is simply broken and the device releases from the esophagus 16. This provides a safety improvement over conventional ventilation devices that rely on an expandable balloon, which if pulled, can cause trauma to the patient's airways, vocal cords, or other structures.

In certain variations, the device 100 shall cease ventilating after a period of time and produce suction through the distal opening. Such a step is considered a safety feature in the event that the working end is moved, repositioned, etc.

In another variation, any of the ventilation devices 100 described herein can be advanced into the mouth while providing a vacuum through the distal opening. This allows automatic sizing of the device as the esophagus will collapse against the distal opening once the device enters the esophagus.

Figure 6A:
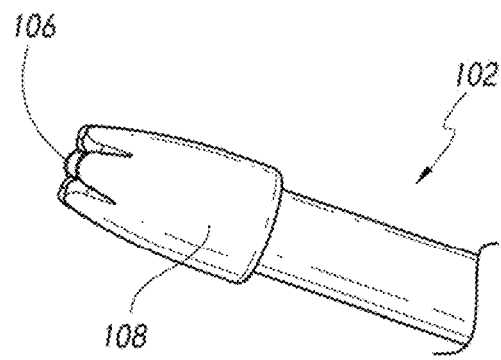
FIGS. 6A to 6C show additional variations of a working end of a ventilation device.
Figure 6B:
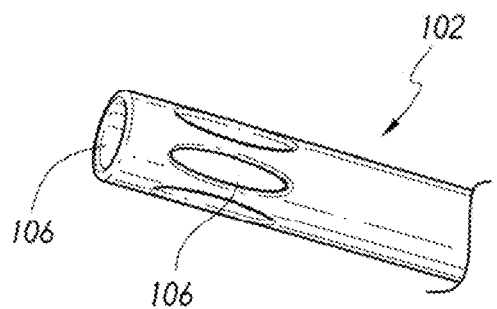
Figure 6C:
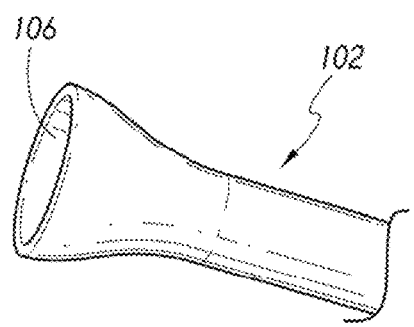

FIGS. 6A to 6C show variations of the working end 102 of a ventilation device as described herein. FIG. 6A illustrates a hub having an opening 106 that is surrounded by a contoured surface. The contoured surface can assist reducing the chance that the distal opening 106 becomes clogged due to food particles or other fluids. This feature also assists in reducing the occurrences that the control unit misreads an opening 106 that is obstructed (with food particles or other bodily fluids) for an opening that formed a seal with the walls of the esophagus. FIGS. 6B and 6C illustrate additional variations of a working end 102 of a ventilation device. In these variations, the working end 102 can be fabricated with or without a hub. FIG. 6B illustrates a straight tube having a plurality of openings 106. FIG. 6C illustrates a beveled end having an opening 106.

Figure 7:
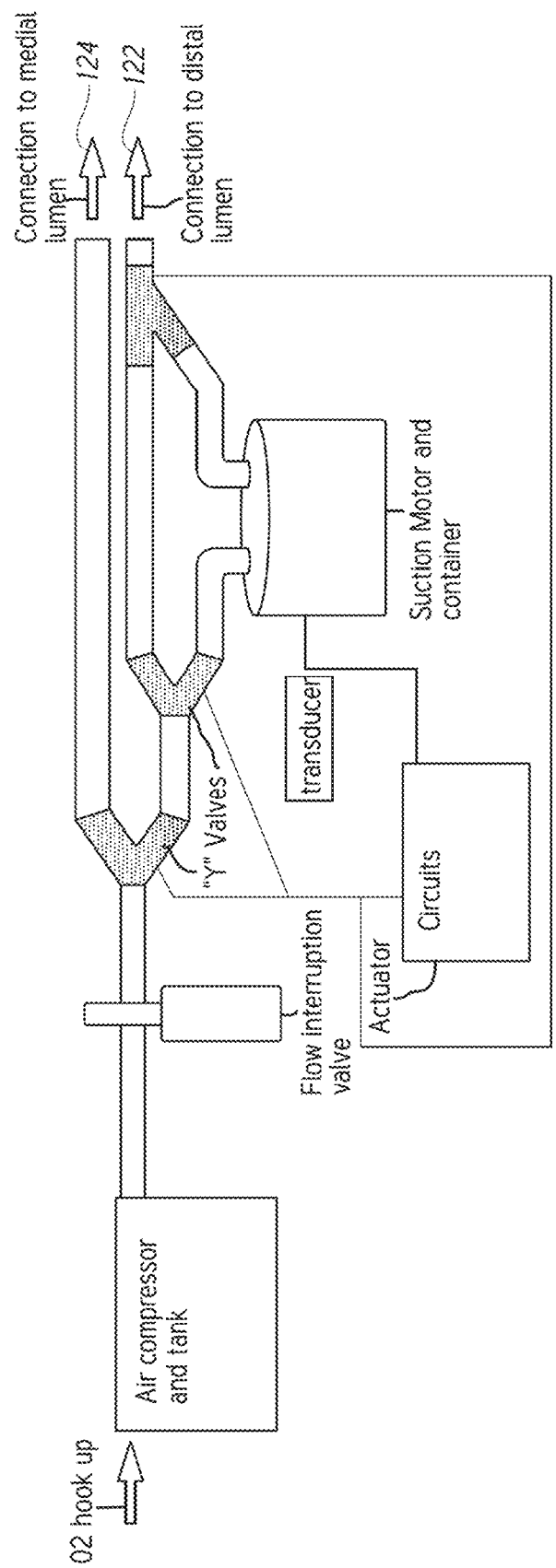
FIG. 7 illustrates a schematic of an electrically powered system.

As noted above, the device described herein can be pneumatically driven using compressed gas and valves or electrically controlled. FIG. 7 illustrates a schematic of an electrically powered device using a suction motor, air compressor and circuitry to switch between a first fluid path 122 (ultimately fluidly coupled to a distal opening) and a second fluid path 124 (ultimately fluidly coupled to a medial opening).

Figure 8A:
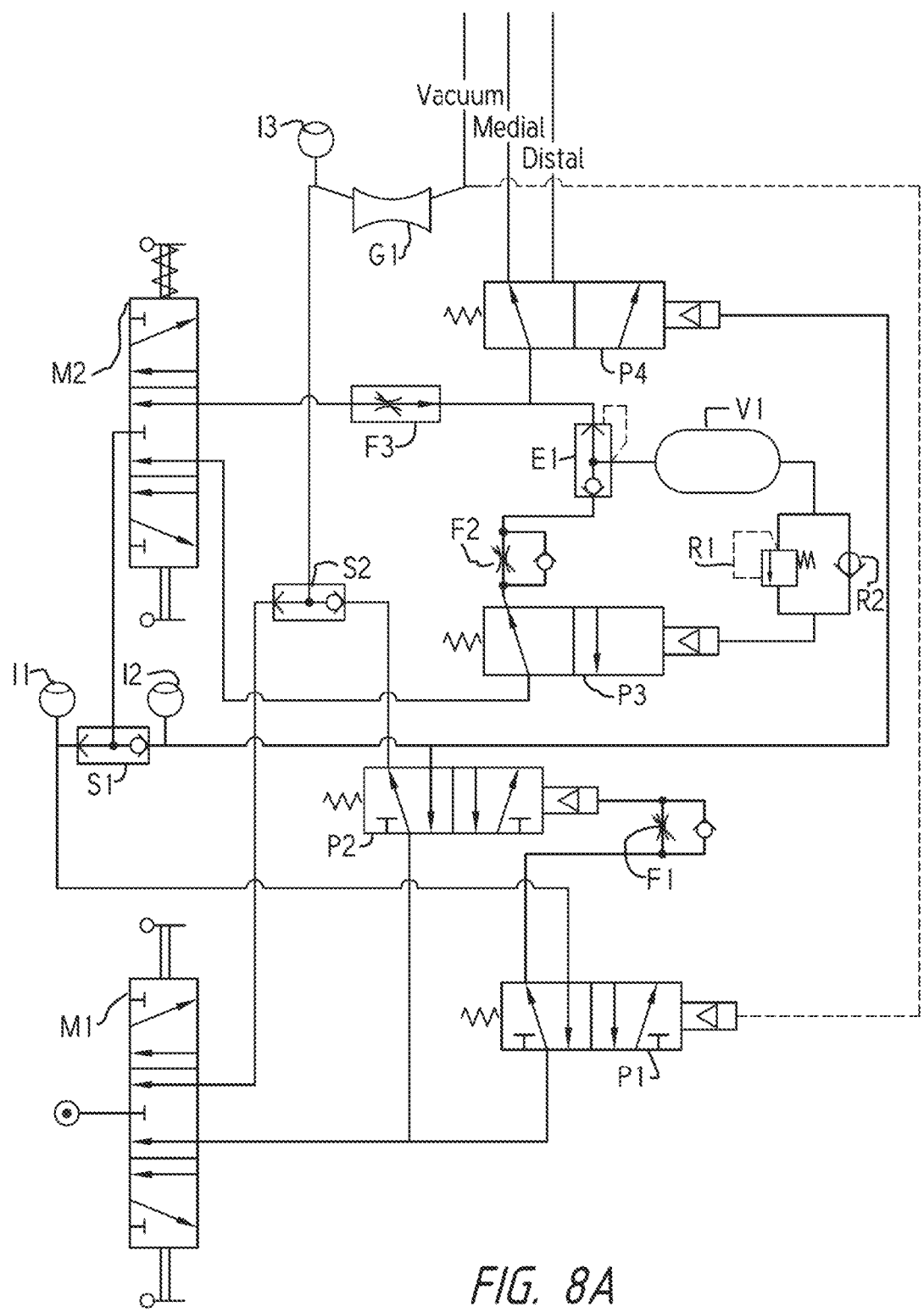
FIG. 8A shows an example of a component schematic for a pneumatically driven system as described herein.

FIG. 8A shows an example of a component schematic for a system as described herein that is pneumatically driven. FIG. 8B provides a list of the components found in FIG. 8A. The valves operate in multiple states based on the conditions discussed above. The following description illustrates an example of the different states of the components found in the component schematic of FIG. 8A.

Medial Supply Valve P1 (4/2);
 State 1 (nominal, spring return): Controls the 15 s timing of vacuum supply through Distal Supply Valve P2;
 State 2 (actuated): Provides supply for medial ventilation;
 Pilot Actuation: 10″ Hg vacuum
Distal Supply Valve P2 (4/2)
 State 1 (nominal, spring return): Provides supply for Vacuum Generator;
 State 2 (actuated): Provides Supply for Distal Ventilation;
 Pilot Actuation: 40 psi from flow-controlled output of Medial Supply Valve, State 1.
Pulse Valve P3 (3/2 Normally Open);
 State 1 (nominal, spring return): Fills Accumulator volume at flow-controlled rate until set pressure is achieved at inline Relief Valve;
 State 2: (actuated): Dumps accumulator volume to Ventilation Selector Valve through quick exhaust;
 Pilot Actuation: 5 psi from output of inline Relief Valve
Ventilation Selector Valve P4 (3/2 Fully Ported);
 State 1 (nominal, spring return): Routes output of Pulse Valve to Medial Ventilation Output;
 State 2: (actuated): Routes output of Pulse Valve to Distal Ventilation Output;
 Pilot Actuation: 40 psi from output of Distal Supply Valve, State 2
Operation Valve M1 (Manual Toggle, 3 position, All Detent);
 State 1 (toggle down, "ON"): Provides supply for Medial Supply Valve and Distal Supply Valve;
 State 2 (toggle centered, "OFF/RESET"): Blocks supply, vents system;
 State 3 (toggle up, "VACUUM"): Bypasses all valves, provides supply to Vacuum Generator.
Mode Valve M2 (Manual Toggle, 3 position, Detent/Detent/Momentary);
 State 1 (toggle down, detent, "VENTILATE"): Provides supply for Pulse Valve and Ventilation Selector Valve;
 State 2 (toggle centered, detent, "BYPASS"): Blocks supply to Pulse Valve and Ventilation Selector Valve.
 State 3 (toggle up, momentary spring return, "ON-DEMAND"): Blocks supply to Pulse Valve, provides continuous flow-controlled supply to Ventilation Selector Valve The system illustrated by the component schematic of FIG. 8A can have a variety of modes of operation. In one example, as shown by FIG. 8C, the system can include 8 separate modes of operations controlled by the position of various valves and the operation state of a medial supply valve.

Figure 8E:
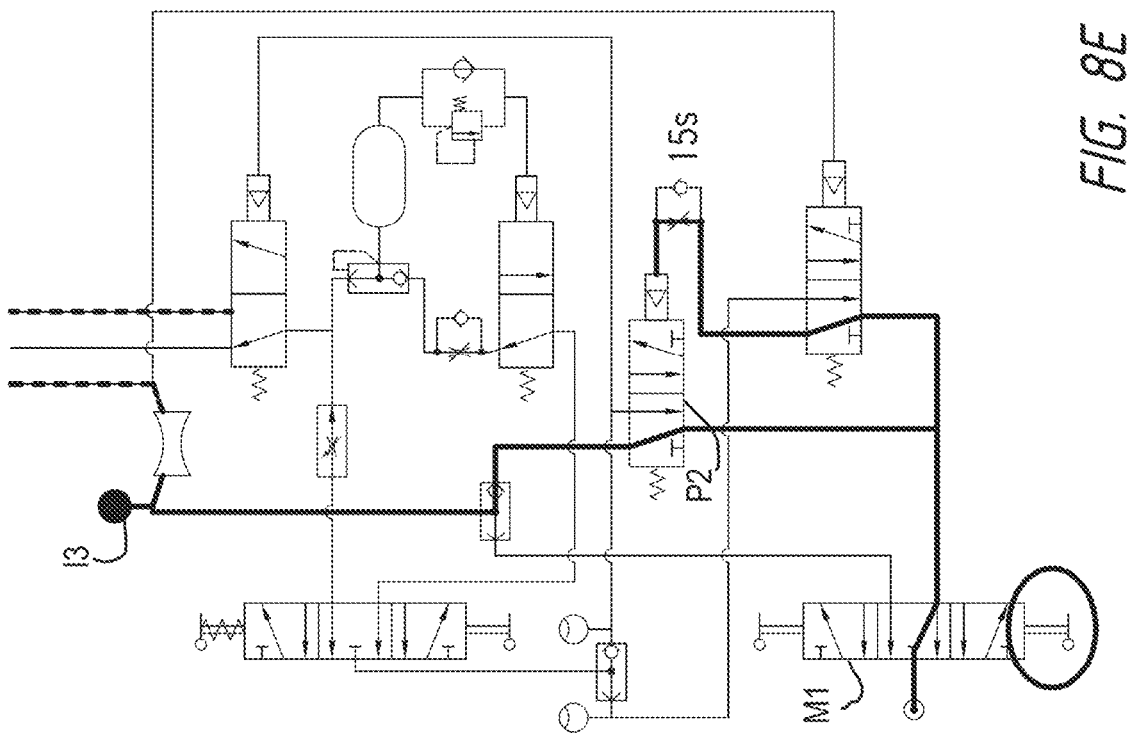
FIGS. 8D to 8M illustrates various flow paths for the various modes of operation.
Figure 8D:
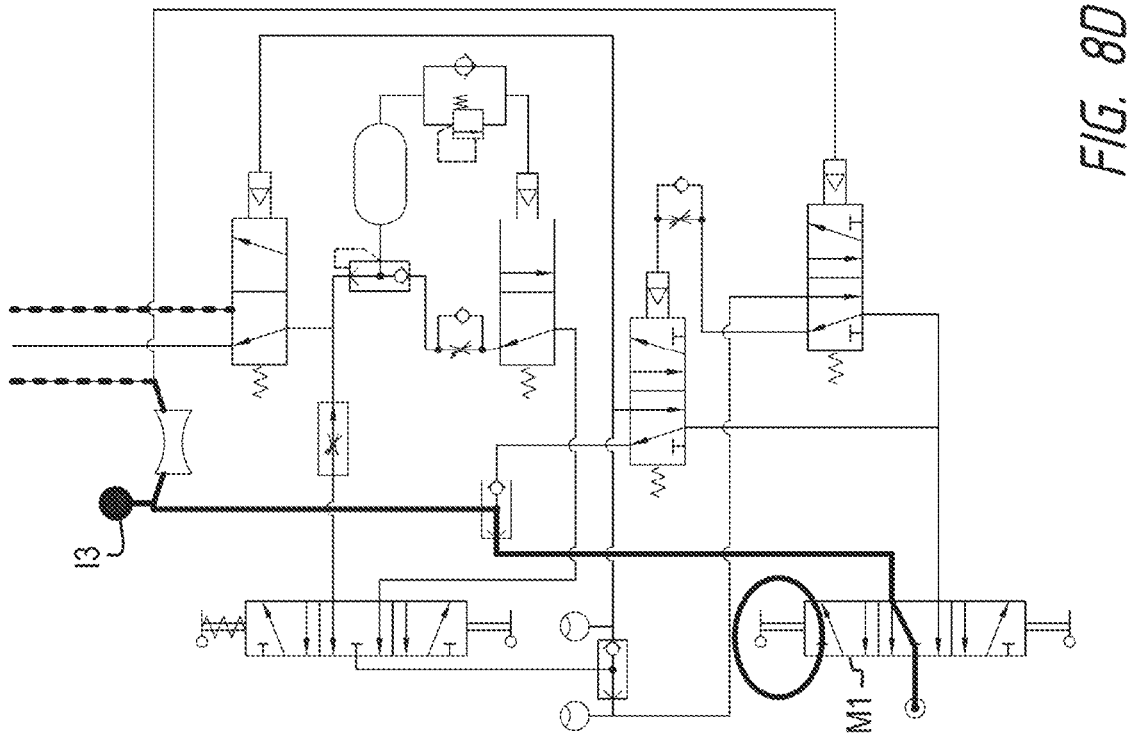
Figure 8G:
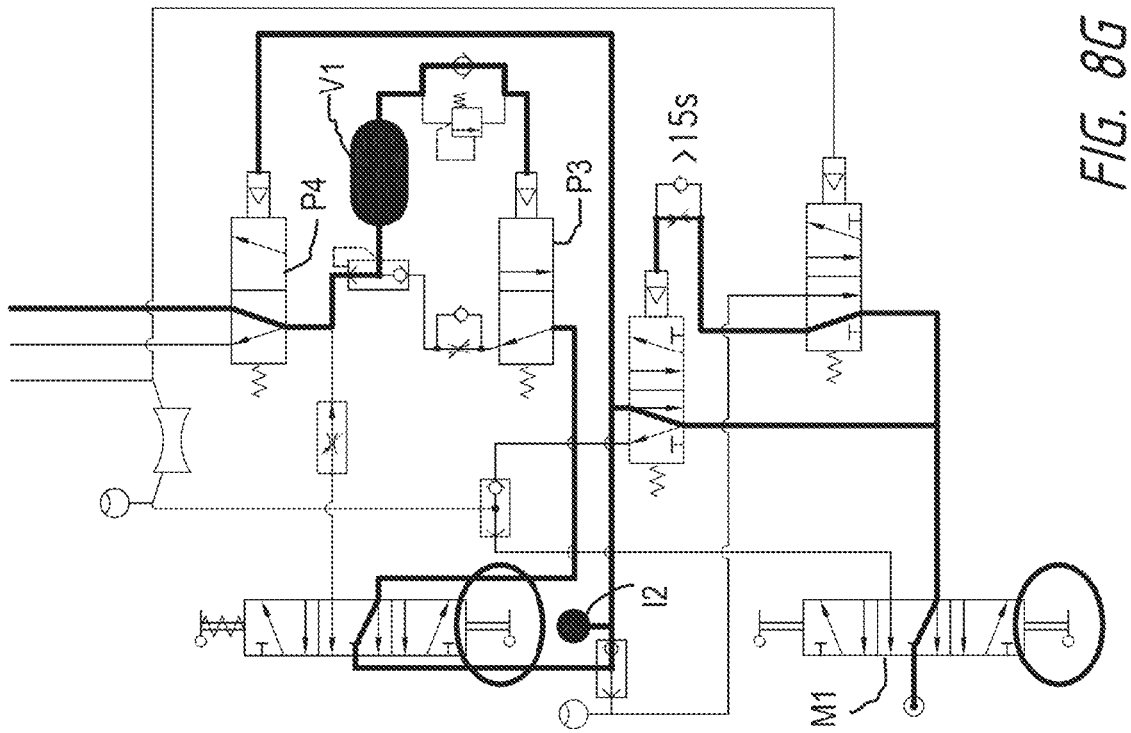
Figure 8F:
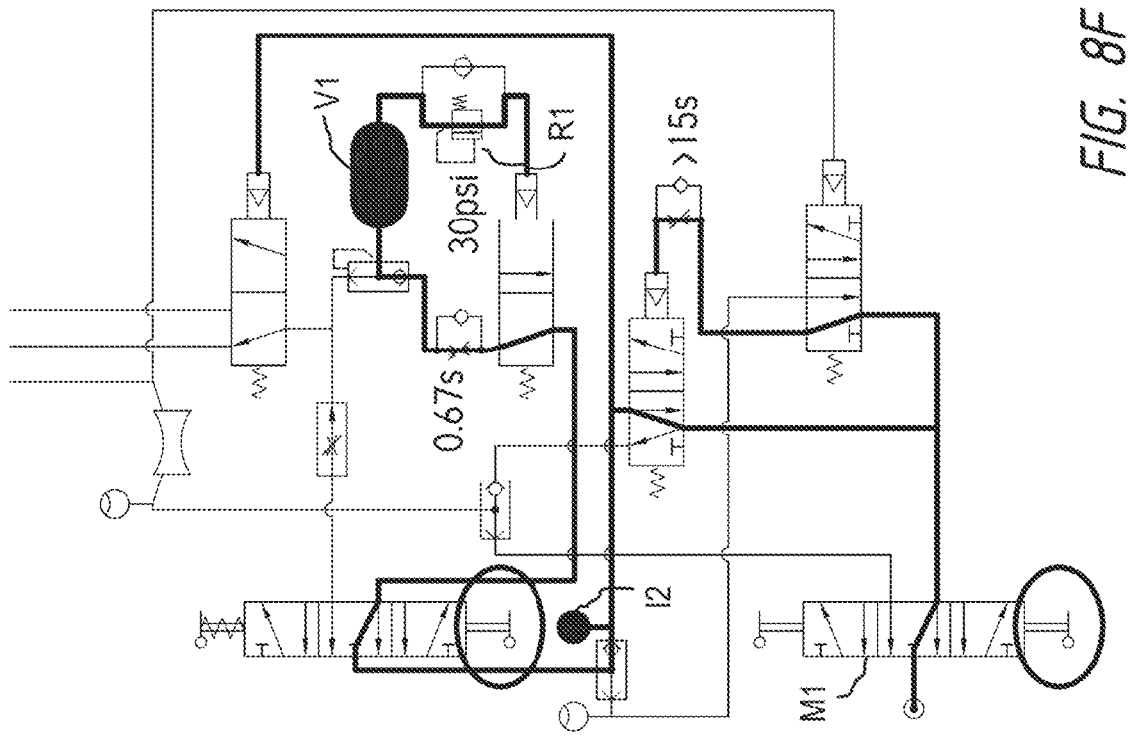
Figure 8I:
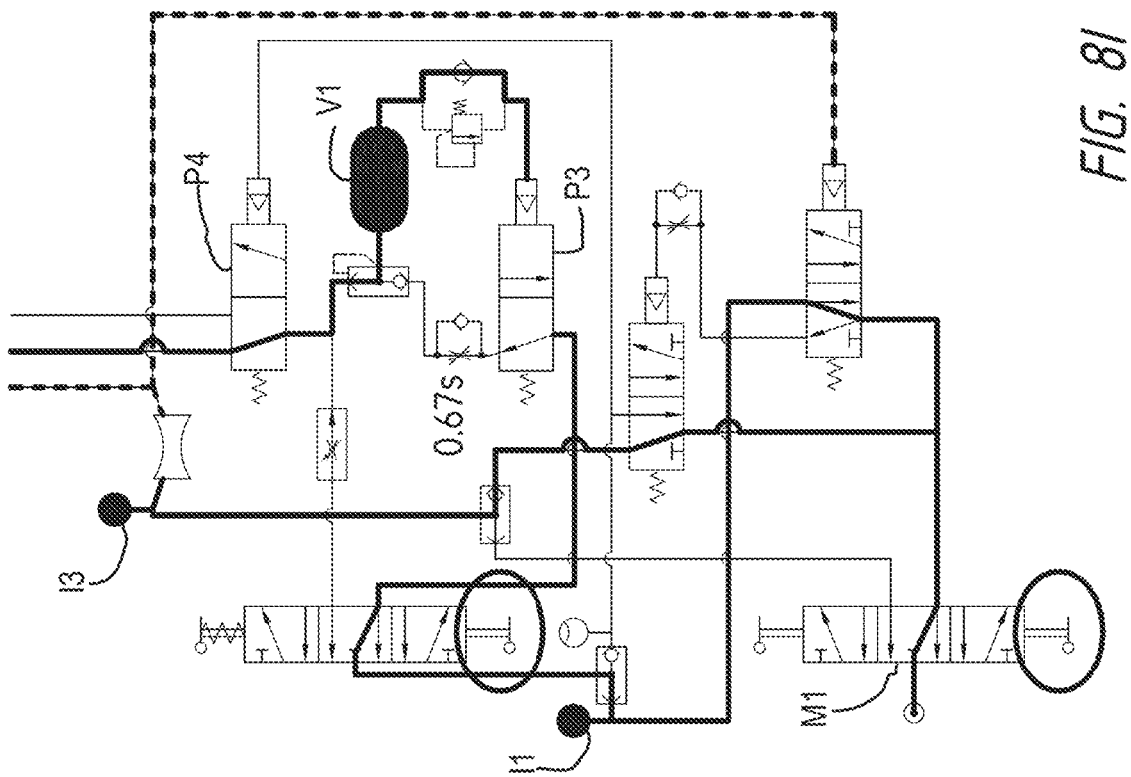
Figure 8H:
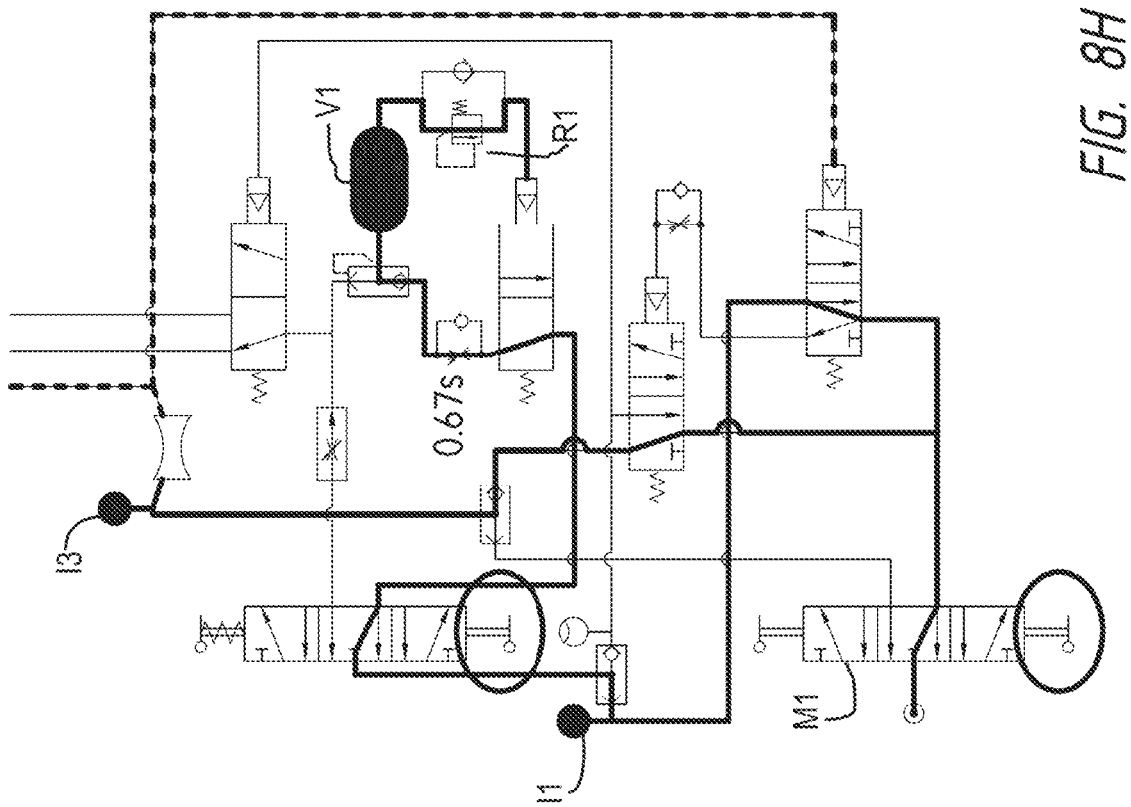
Figure 8K:
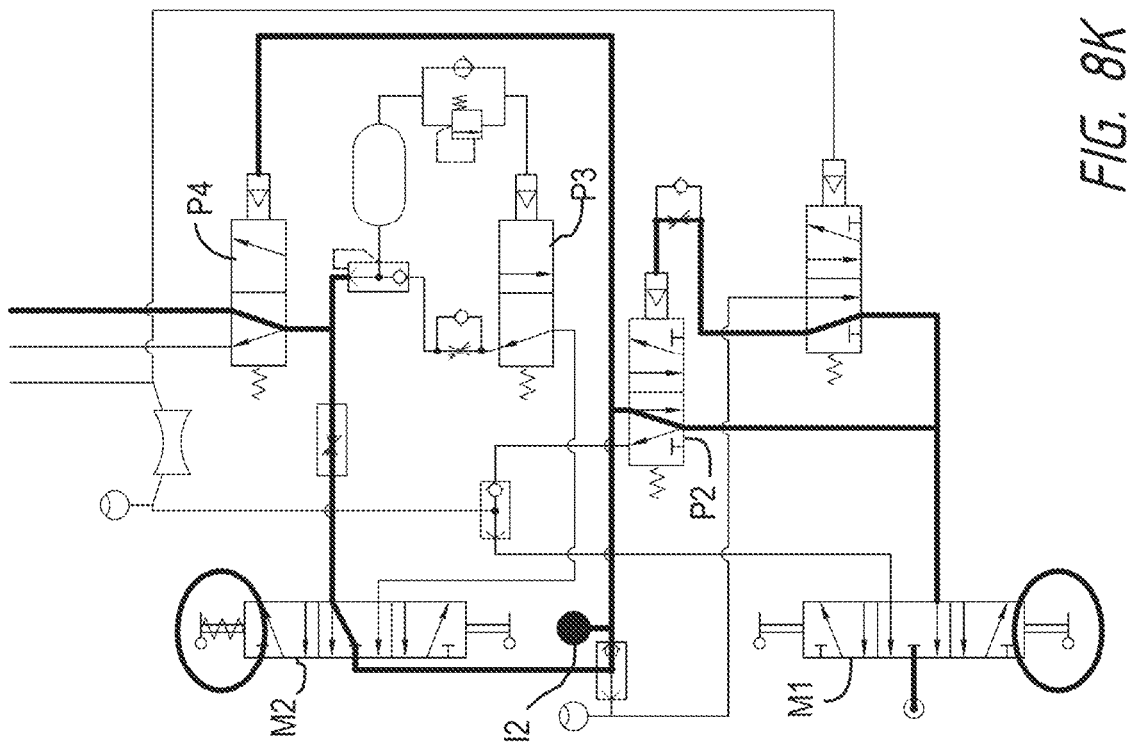
Figure 8J:
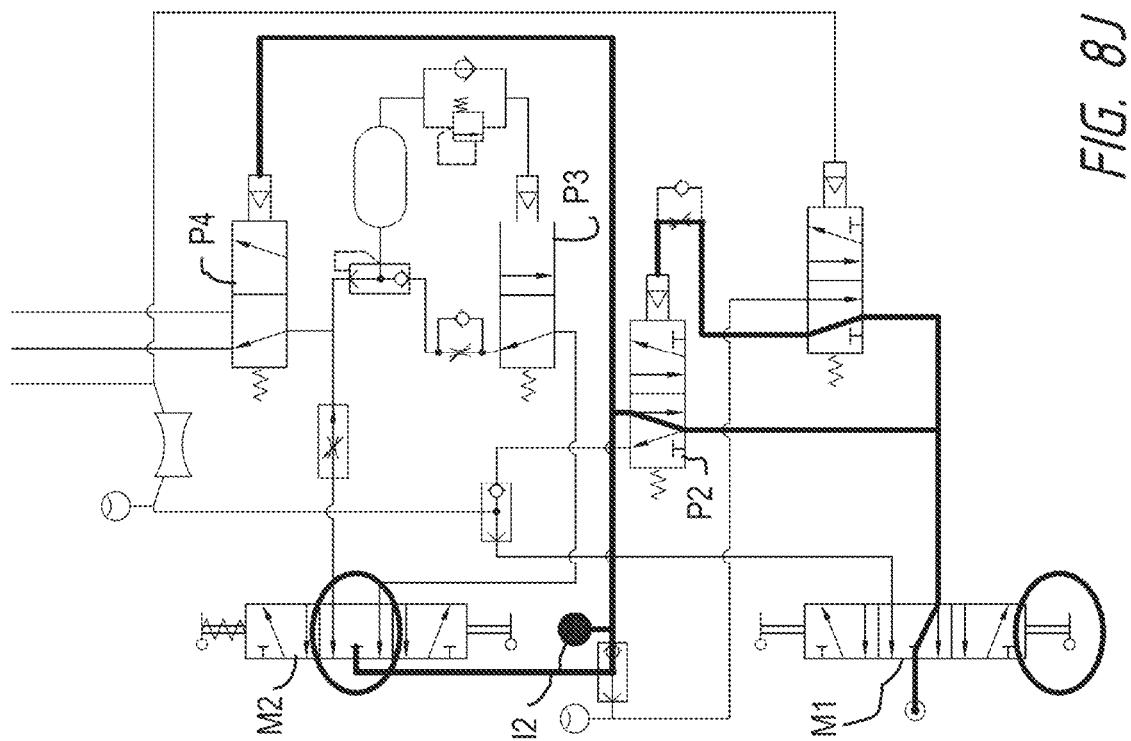
Figure 8M:
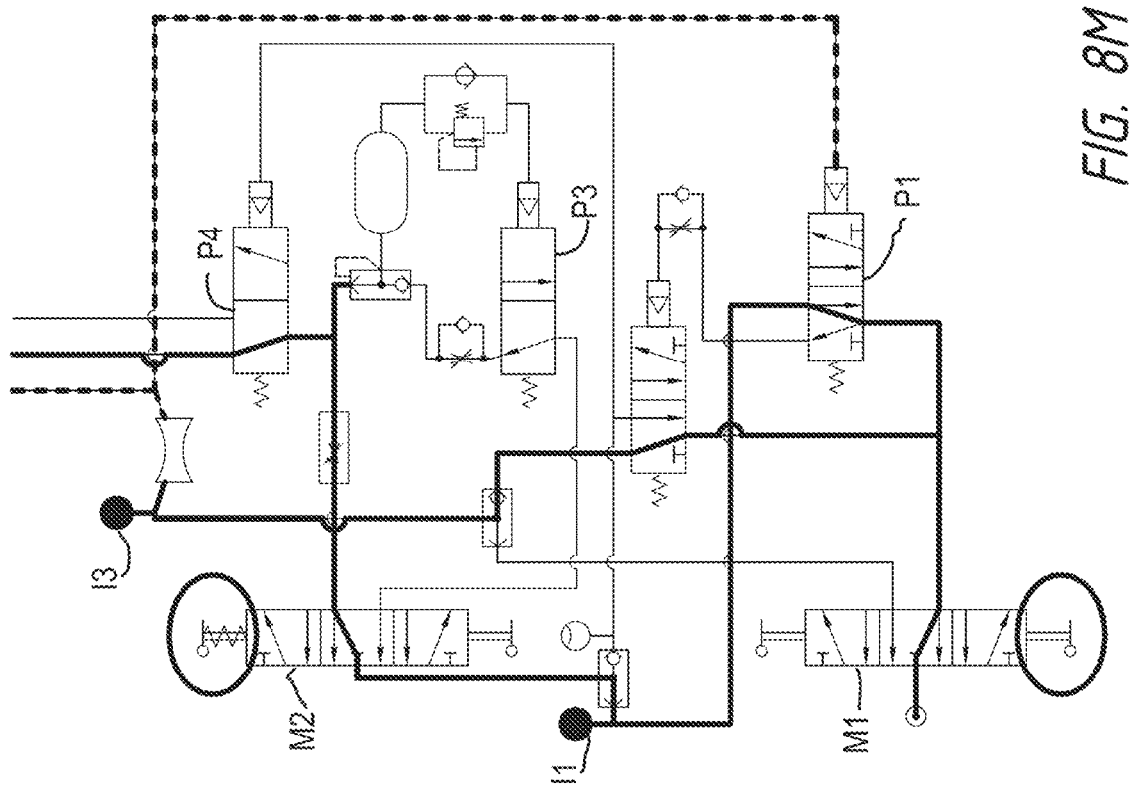
Figure 8L:
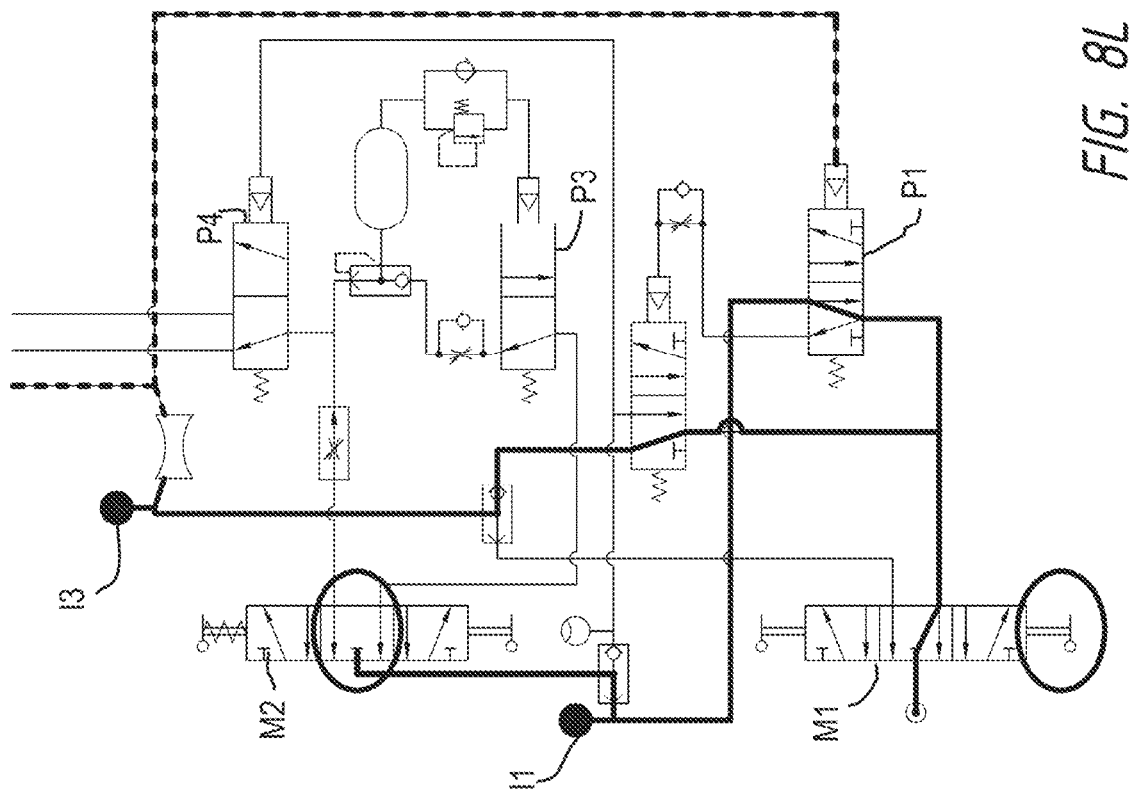

Mode 0, where the system is set to an Off position.
 M1 set to OFF;
 Main supply blocked; system vented;
FIG. 8D shows Mode 1, where there is a continuous vacuum applied through the system.
 M1 set to VACUUM
 Ventilation system bypassed; vacuum at Vacuum Output; Vacuum Indicator on
FIG. 8E shows Mode 2, where the system engages in placement detection;
 M1 set to ON;
 Vacuum at Vacuum Output until P2 pilot activated (15 s); Vacuum Indicator on;
In Mode 3, the system engages in ventilation through the distal opening.
 M1 set to ON; M2 set to VENTILATE;
 No vacuum detected; P2 pilot activated; P4 pilot activated.
FIG. 8F shows Mode 3A, where an accumulator fills at controlled rate (0.67 s) until inline Relief Valve activates (30 psi);
 Distal Ventilation Indicator on.
FIG. 8G shows Mode 3B: P3 pilot activates, closing P3 and exhausting Accumulator volume through Quick Exhaust to P4; Distal Ventilation Indicator on.
 Mode 4—Medial Ventilation
 M1 set to ON; M2 set to VENTILATE
 Vacuum detected; P1 pilot activated; vacuum at Vacuum Output.
FIG. 8H shows Mode 4A where accumulator fills at controlled rate (0.67 s) until inline Relief Valve activates (30 psi);
 Vacuum Indicator on;
 Medial Ventilation Indicator on.
FIG. 8I shows Mode 4B: P3 pilot activates, closing P3 and exhausting Accumulator volume through Quick Exhaust to P4;
 Vacuum Indicator on; Medial Ventilation Indicator on.
FIG. 8J shows Mode 5—Ventilation Bypass (Distal);
 M1 set to ON; M2 set to BYPASS;
 No vacuum detected; P2 pilot activated; P4 pilot activated; supply to P3 & P4 blocked; Distal Ventilation Indicator on.
FIG. 8K shows Mode 6—On-Demand Ventilation (Distal);
 M1 set to ON; M2 set to ON-DEMAND;
 No vacuum detected; P2 pilot activated; P4 pilot activated; supply to P3 blocked; continuous flow-regulated flow to P4; Distal Ventilation Indicator on
FIG. 8L shows Mode 7—Ventilation Bypass (Medial);
 M1 set to ON; M2 set to BYPASS;
 Vacuum detected; P1 pilot activated; vacuum at Vacuum Output;
 supply to P3 blocked;
 Vacuum Indicator on;
 Medial Ventilation Indicator on
FIG. 8M shows Mode 8—On-Demand Ventilation (Medial);
 M1 set to ON; M2 set to ON-DEMAND;
 Vacuum detected; P1 pilot activated; vacuum at Vacuum Output;
 supply to P3 blocked;
 continuous flow-regulated flow to P4; Vacuum Indicator on; Medial Ventilation Indicator on.

Figure 9A:
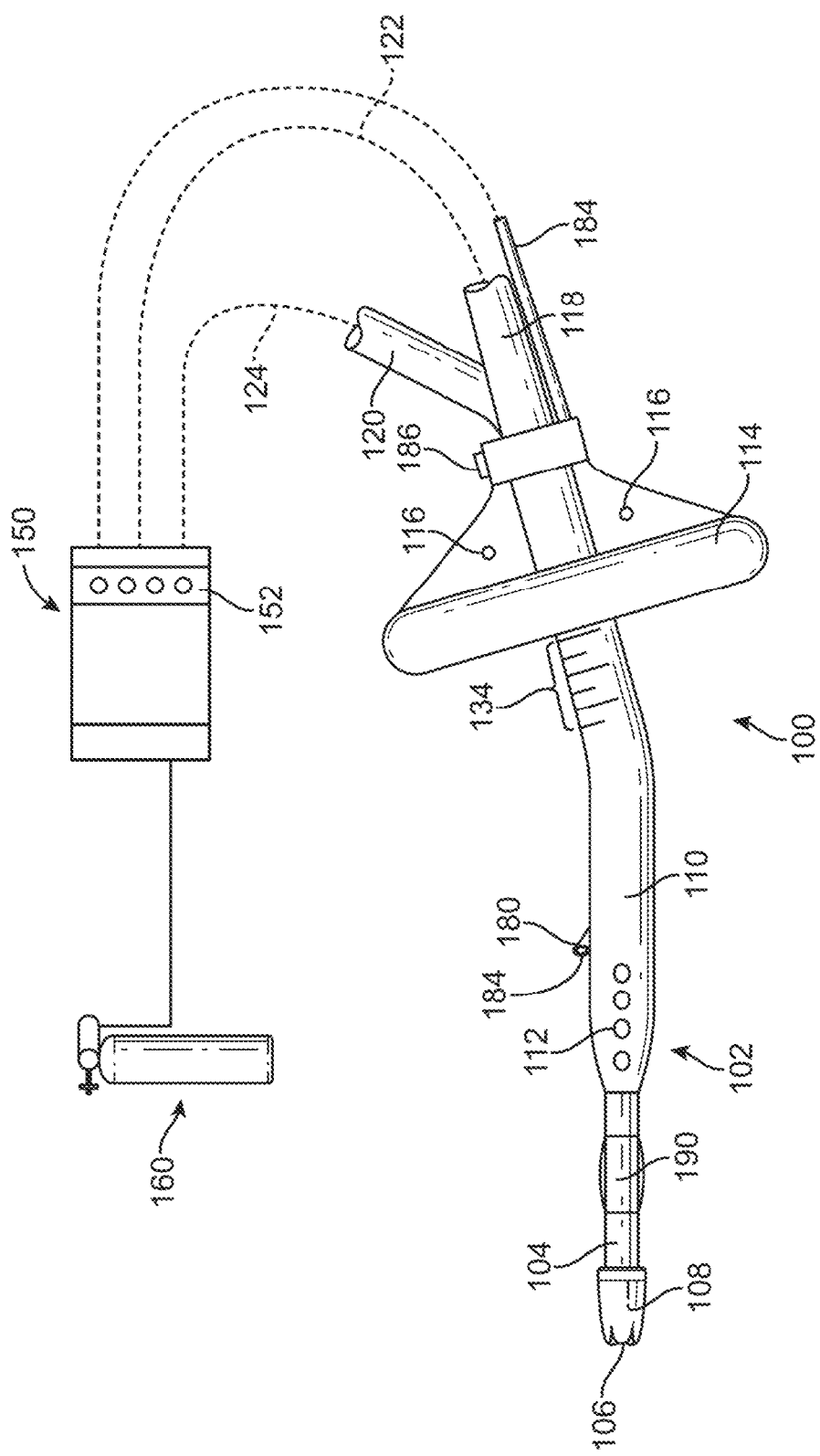
FIG. 9A illustrates another variation of a device useful for providing assisted ventilation with improved outcomes by monitoring a condition of the thoracic cavity.

FIG. 9A illustrates another variation of a device useful for providing assisted ventilation with improved outcomes. The features and aspect of the illustrated example can be combined with any of the variations of the devices described herein. Moreover, the features of the devices described herein that improve the effectiveness of assisted ventilation can be used with conventional assisted ventilation devices.

As illustrated, assisted ventilation device 100 includes a working end 102 that is inserted into a patient. The working end can include a distal tubing 104 that contains a first lumen (not shown), which extends through a distal opening 106 of the ventilation device 100 and is in fluid communication with a control unit (also called a ventilator) 150 and/or supply source 160 via one or more proximal tubes 118. The control unit 150 can also include an apparatus designed to provide suction as well as a collection canister (not shown). As noted above, the device 100 can optionally include an improved control unit 150 that directs suction or applies a vacuum through a first fluid path 122, which in turn causes a suction or negative pressure at the distal opening 106. The source 160 can comprise oxygen, air, or any other gas that is desired for ventilation of delivery into the lungs. The source 160 can be nested within physical construct of the controller 150. However, the source 160 can be optional so that the controller ventilates the patient only using ambient air. FIG. 9A also illustrates the device 100 as including features that allow the assisted ventilation device 100 to deliver ventilation in a manner that improves the efficiency of the assisted ventilation procedure.

For example, the improved device 100 can include one or more structures used to determine a change in the thoracic cavity. Such changes can include physical movement of the tissues within the thoracic cavity, the force applied to the working end 102 of the device 100, and/or the deflection of any part of the device 100. Alternatively, or in combination, a change in the thoracic cavity can comprise a change in the fluid environment of the thoracic cavity, including any body passageways that are in fluid communication with the thoracic cavity, e.g., the airway, the esophagus, etc.

FIG. 9A illustrates the device 100 as being able to measure fluid parameters in the thoracic cavity via a sensor 180 located along a portion of the working end 102 of the device. Although the sensor 180 is illustrated on the proximal tubing 110, the sensor 180 can be positioned along any portion of the device 100 that enables monitoring of the fluid parameters of the thoracic cavity and/or body passage in fluid communication with the thoracic cavity. For instance, the device 100 can include one or more sensors 180 positioned along the distal tubing 104 and/or hub 108. Moreover, variations of the device include one or more sensors positioned within the device 100.

The sensor 180 can comprise a pressure sensor, flow sensor, transducer, or similar structure. Alternatively, in additional variations, the sensor 180 can comprise a lumen or passageway having an open end positioned as described above, where the lumen or passageway extends through the device via a sensor tubing 182 that allows the actual fluid parameters to be read by the actual sensor located within the device 100, tubing 118, and/or control unit 150.

The variation illustrated in FIG. 9A also shows a sensor 180 that is not flush with the proximal tubing 110 of the device 100. As shown, the measurement surface (e.g., the actual sensor or the sensor lumen 184 can be positioned so that tissue adjacent to the device 100 does not obscure or affect the readings of the sensor. However, additional variations of the device 100 include sensors that are flush with the device body. In addition, pressure from the device 100 (e.g., the proximal tube 118 can be used to deliver air to the sensor 180 reduce obstructions from interfering with the measurement of any fluid parameter in the body lumen.

FIG. 9A also illustrates a force detecting component, such as a strain gauge, optic fiber, transducer, or similar force/movement detecting structure that can be located anywhere along the working end 102 of the device 100. The force detecting component 190 is shown as being on the distal tubing 104, however, one or more force detecting components 190 can be positioned along any portion of the device as long as the component 190 detects a force applied to the chest via a resulting force being applied to the device through movement of the tissue displaced by assisted chest compression.

The presence of both the sensor 180 and the force detecting component 190 on a single device is for purposes of illustration only. Certain variations of the device can include any combination of force detecting component, sensor, or both.

FIG. 9A also shows the device as including a manual ventilation trigger 186. In operation, the medical caregiver can use the manual ventilation trigger 186 to manually deliver a bolus of air through the device 100. Alternatively, or in combination, the manual ventilation trigger 186 can activate the sensor 180 or force detecting component 190 to deliver a bolus of air on demand. Such a feature can be useful if the care giver has obtained a pulse and intends on delivering assisted ventilation alone. Alternatively, the caregiver can use the manual ventilation trigger 186 to deliver a bolus of air through any part of the device in an attempt to clear bodily fluids that might otherwise obstruct the device. The manual ventilation trigger 186 can operate as the device performs the automated assisted ventilation where a bolus of air is delivered at certain period of time. Alternatively, or in combination, the manual ventilation trigger 186 can deliver a bolus of air when the ventilation device 100 (or controller 150) is placed in a manual-mode.

In certain variations of the device, when initiating the manual trigger 186, the device be programmed to maintain ventilation through the respective opening that was selected in the automatic mode. For example, if the device is placed in the esophagus, and then switched to manual operation, the control system can maintain suction to ensure that the esophagus closes the distal opening and forms a vacuum so that manual ventilation automatically proceeds through the proximal or medial opening 112. Likewise, if the device is positioned in the trachea, actuating the device in a manual mode will cause the bolus of air to be expelled from the distal opening of the device.

In one example, the trigger 186 comprises a hollow button, attached to the device and in line with the tubing that connects to the sensor 180. When the button is pressed it sends an air bolus to the sensor 180 that signals the control system 150 to start assisted ventilation. The volume of air provided by the manual trigger 186 can be preset. Alternatively, air can be delivered until the caregiver releases the trigger 186 to stop the ventilation. In addition, mounting the trigger 186 mounted on the mask 114 is beneficial because it allows the caregiver to ensure the mask 114 is sealed against the patient's face with one or two hands while operating the demand ventilations.

The manual trigger 186 can also operate to with one or more one-way valves (e.g., a flap that allows exhaust of air when the trigger 186 is not pressed). This ensures that there is no excess buildup of pressure in the airway and prevents barotrauma. This also allows spontaneous breathing. When the ventilator is switched to demand ventilation mode the lungs need to be isolated from atmosphere during the inhalation period only. This can be achieved by having the demand ventilation trigger 186 mounted on a flap that is above an opening on the mask. The flap is designed to be opened with when no pressure is being applied to the button, then once pressure is applied to the trigger the flap is sealed against the opening, closing the system and allowing air to inflate the lungs. When the button is released for exhalation the flap is comes off the mask opening allowing air to escape and lungs deflate.

FIG. 9B illustrates a variation of a portion of a device 100 showing a mask 14 having a trigger 186 that is coupled to an exhaust port 116. In this variation, the mask 114 also includes one or more pressure release valves 117 that will crack or permit flow beyond an established pressure. Such a fail-safe presents unsafe pressurization of the airway by the device. The pressure release valves 117 can be surrounded by protrusions or features 115 that prevent objects from blocking the valves 117. The device 100 is also shown with an adjustment control 183 that permits movement of the mask 114 along the tube 110. FIG. 8B also illustrates a tubing 185 that couples the trigger 186 to the sensor lumen 184. As shown, the sensor lumen 184 can be coupled with a t-fitting or other fluid coupling so that a portion of the lumen is in fluid communication with the trigger 186 as described below.

Figure 9C:
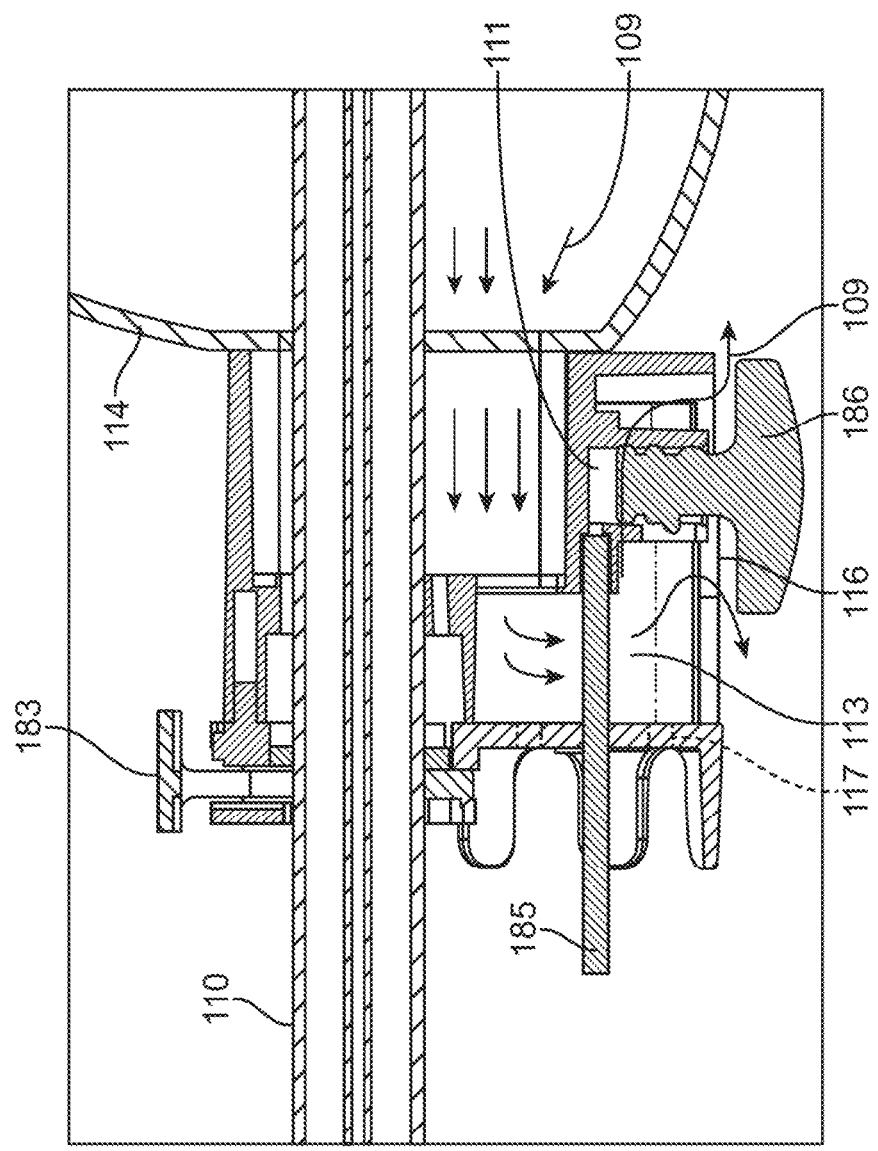

FIG. 9C illustrates a partial cross-sectional view of the mask 114 and tubing 110. As shown, when the mask is positioned against the respiratory opening of the patient (i.e., a mouth or nose), airflow from the expiratory cycle (represented by arrows 109) flow through a portion of the mask 114 and into a chamber 113 that is in fluid communication with the exhaust lumens 117. However, in this condition, the trigger 186 is not being pressed against the mask 114 such that the exhaust port 116 remains open allowing airflow 109 to exit the mask. Furthermore, the trigger 186 can be positioned in a shaft having a compressible air volume 111 that is in fluid communication with the tubing 185. Accordingly, although the mask 114 is pressed against the patient, the exhaust port 116 permits the system to be open (fluidly open).

Figure 9D:
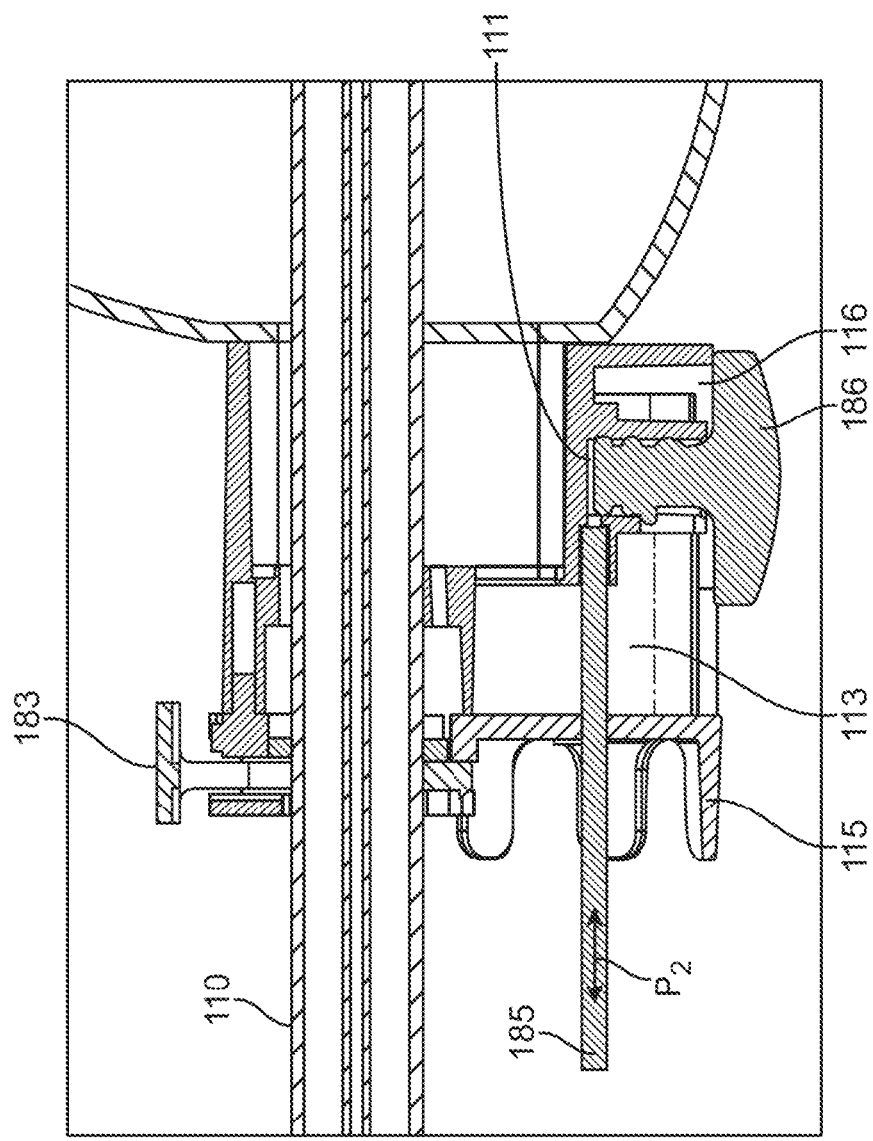
FIG. 9D illustrates a condition where a trigger in the system fluidly closes by closing the exhaust port.

FIG. 9D illustrates a condition where the trigger is pressed or actuated (the trigger can be on a spring return or have elasticity to function as a spring return). Once actuated, the trigger 186 fluidly closes the system by closing the exhaust port 116. The action of the trigger 186 can also be used initiate a manual bolus of air through the tubing 110. For example, the trigger 186 can have one or more electrical contacts or switches in region 111 that provides a signal to the control system to deliver a bolus of air. In an additional configuration, actuation of the trigger 186 compresses the volume of air in space 111 causing a pressure increase P2 in tube 185, which is coupled to the sensor lumen 184, this increase in pressure causes the sensor lumen to perform a manual ventilation by delivering a bolus of air through the tubing 110. Likewise, when the trigger 186 is released, the expansion in volume of region 111 creates a drop in pressure in tubing 185 as well as in the sensor lumen 184, where the drop in pressure is registered by the sensor to stop ventilation.

In addition to the sensor 180 and/or sensor lumen 184 the device 100 can include any number of additional lumens to provide information to monitoring equipment. For example, the device can include one or more lumens that are fluidly coupleable to a capnograph device. Alternatively, or in combination, the sensor lumen 184 can also allow fluid coupling to a monitoring device. In such a case, the lumens can be coupled to one or more openings (such as 180) located on the working end of the device.

Figure 9E:
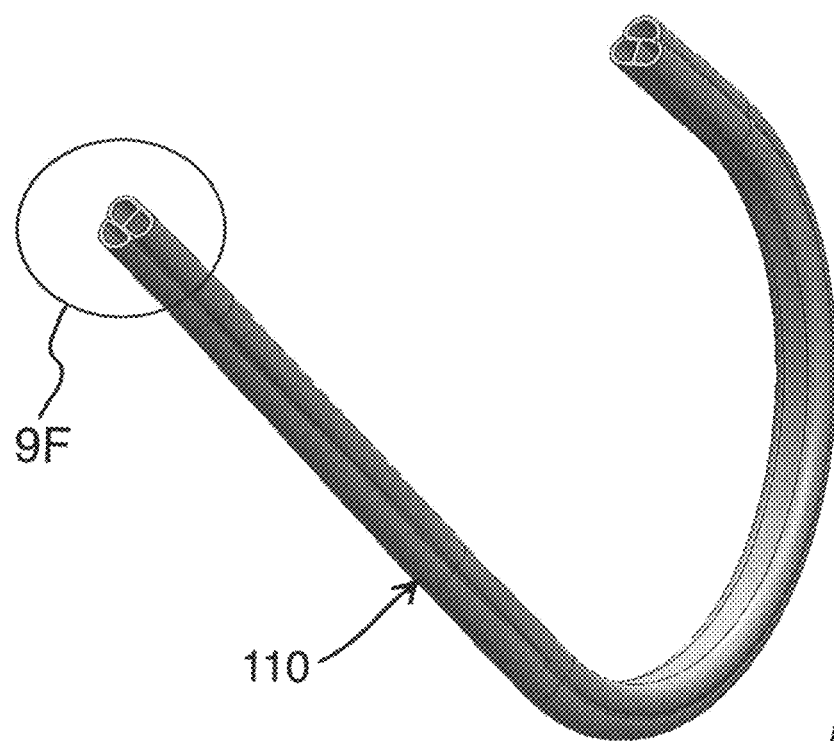
FIGS. 9E and 9F illustrate another example of a multi-lumen tubing for use in additional variations of the devices described herein.
Figure 9F:
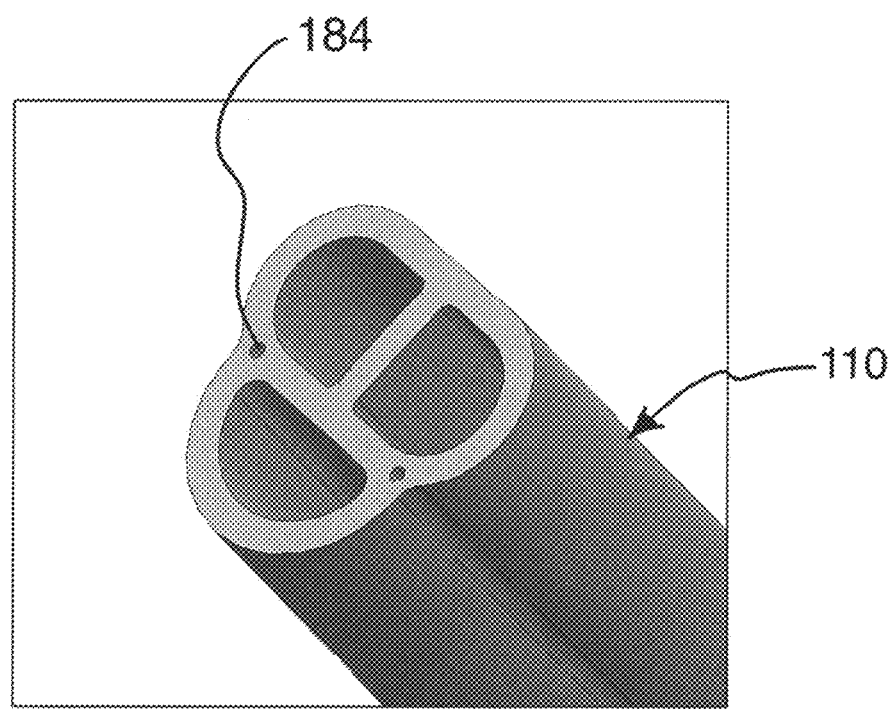

FIGS. 9E and 9F illustrate another example of a multi-lumen tubing 110 for use in additional variations of the devices described herein. As shown, in FIG. 9E the tubing can include multiple lumens as described above. FIG. 9F shows a magnified view of the end of the tubing 110 in FIG. 9E. In addition to the lumens used for ventilation, the multi-lumen construction can include one or more smaller lumens 184 that are fluidly coupled to a sensor or contain a sensor. As discussed herein, the sensor can include a pressure sensor. Variations of the device include one or more sensor lumens 184 that extend through the entirety of the tube and exit at or near the distal end. Alternatively, as discussed herein, the sensor lumen can open at a medial portion of the device.

Figure 10A:
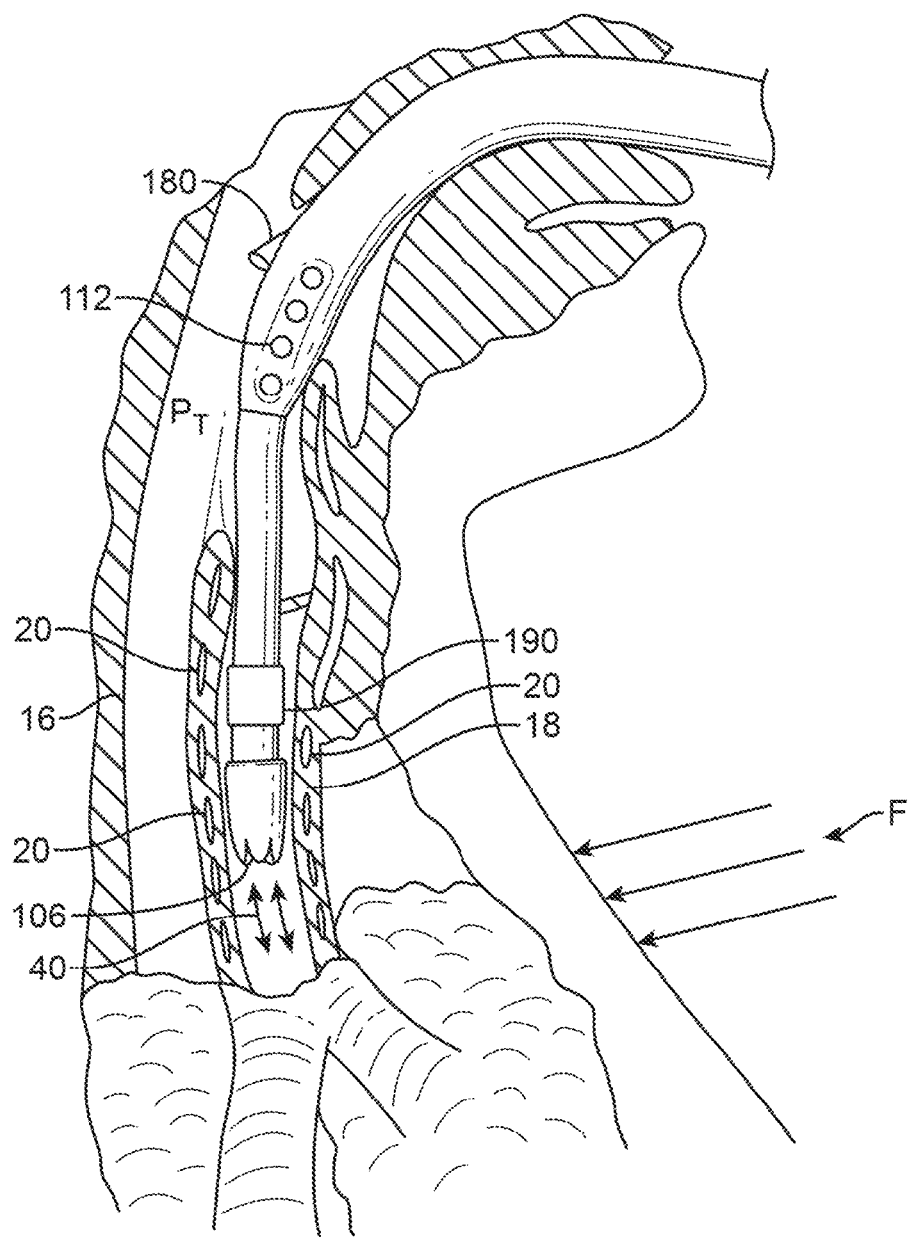
FIGS. 10A and 10B illustrate examples of the working end of the device when inserted into a body passageway of an individual and monitoring a condition of the thoracic cavity.
Figure 10B:
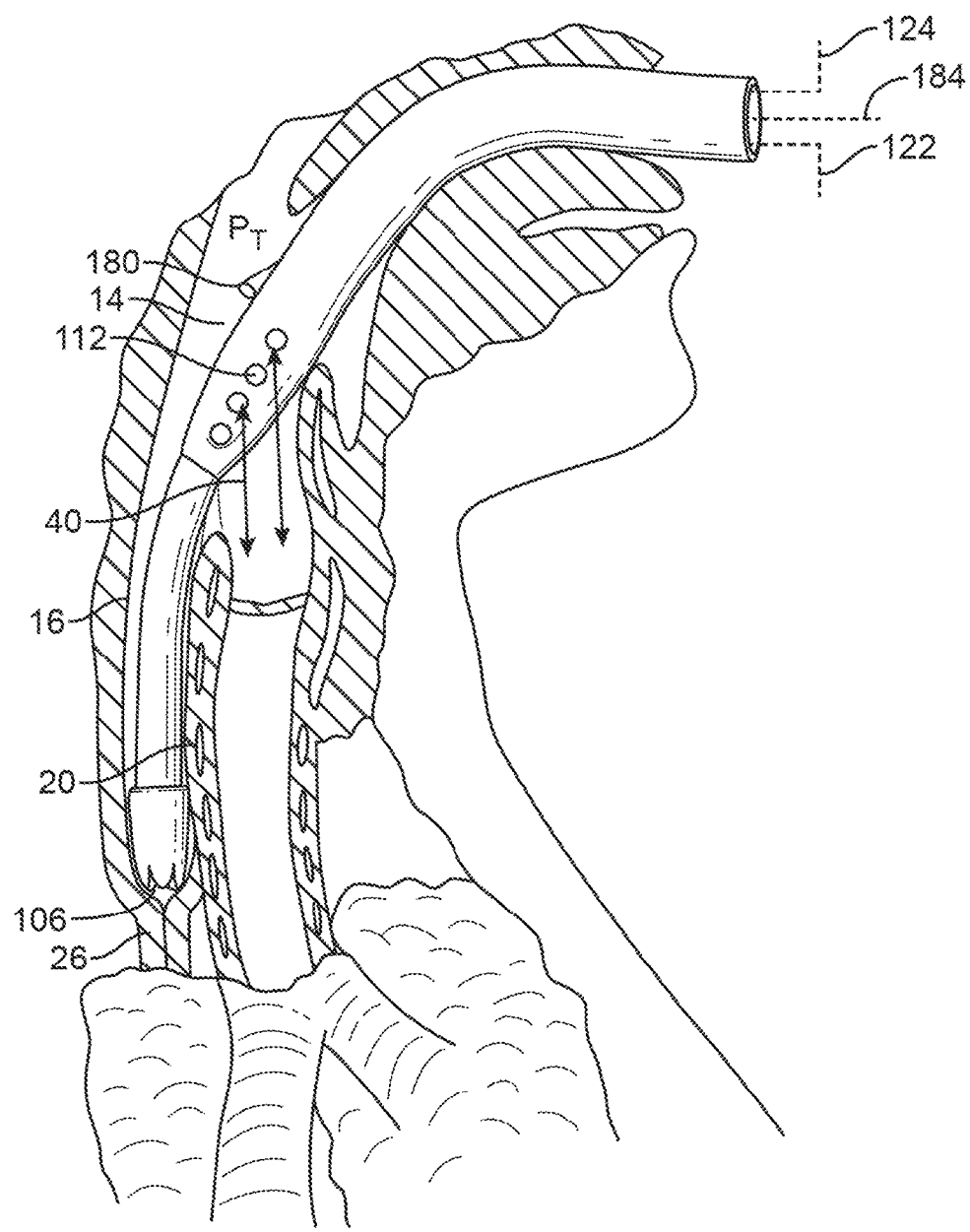

FIG. 10A illustrates an example of the working end 102 of the device 100 when inserted into a body passageway of an individual. In this example, the device is inserted into a trachea 18, where the device 100 detects that it is in an airway as described above. However, as shown in FIG. 10B, variations of the device 100 can also be positioned in the esophagus 16 using the process described above, which temporally seals the esophagus 16 to deliver air to the respiratory passage 18.

In either case, the device 100 is configured to begin assisted ventilation by delivering a bolus of air 40 at a pre-determined rate. The device 100 is configured to measure a condition of a thoracic cavity to determine a change in the thoracic cavity, either through pressure within the thoracic cavity as denoted by PT or a force F applied to the thoracic cavity via chest compressions. In the latter case, the force F applied to the chest causes movement of tissue (such as the trachea or other tissue) that can be determined by a force detecting component 190 as discussed above. The detection of a chance in the thoracic cavity by measuring a fluid characteristic such as a change in pressure PT is typically measured within a body passageway (such as the trachea 18 or esophagus 16). Such measurements can include measuring flow rate of air, volume, pressure, etc.

In one variation, the initial or pre-determine rate comprises 100 ventilations per minute (i.e., a bolus of air is delivered 100 times per minute). However, any rate of delivery is within the scope of this disclosure. Upon detecting a change in the condition of the thoracic cavity, typically due to chest compressions, the device 100 will adjust the timing and/or rate of air delivery to achieve an optimum result. For example, the system can deliver a bolus of air upon detecting the chest compression (either by the force measurement or via the fluid sensor measurement). In such a case, the bolus of air increases pressure in the thoracic cavity to serve as an internal chest compression which compresses the heart and lungs from within causing increased blood flow.

In variations of the device, the system monitors for a change in a condition of the thoracic cavity on a continuous basis, or on a delay. In either case, the system can be configured to not respond to a change in the pressure of the thoracic cavity driven by the delivery of the bolus of air. For example, the system can ignore readings during and immediately after the delivery of the bolus of air.

The process of adjusting the delivery of a bolus of air (either by timing and/or rate) in response to a particular phase of the chest compression is intended for use during CPR. However, the assisted ventilation can be accomplished whether using a mechanical compression system or a caregiver performing manual chest compressions.

The alteration of the timing and/or rate is intended to provide a bolus of air with each or a specific number of compression and at a specific phase of the compression of the patient's chest. As noted herein, the ventilations are timed in a way that both increased the efficiency of the chest compression by increasing intrathoracic pressure during the down stroke of the chest compression, which would increase the pressure on the heart thus increasing blood flow. During the up stroke of the compression of a portion of the ventilation could still be given to allow new air to enter the alveoli while allowing a portion of the up stroke of the compression to create a negative intrathoracic pressure drawing blood back into the heart and air into the alveoli. This technique also prevents a rescuer from having to pause compressions in order give ventilations, which decreases blood flow and decreases odds of patient's survival.

When using the devices described herein, regardless of whether the device is positioned in the trachea or esophagus, the airway is always opened to the outside environment which greatly reduces, if not eliminates, the chance of barotrauma.

The data generated by the devices described herein regarding the efficiency of the compression regarding depth, rate, recoil time can be analyzed and presented via feedback to the caregiver in order to maximize the efficiency of the compressions. All of this information and be used to increase the efficiency of the compressions and therefore increase blood flow of the patient and increasing the patient's chance of survival. If using a mechanical compression system, the cycle phase could be directly linked to the device 100.

Furthermore, the system can be configured to return to a pre-determine rate of providing the bolus of air, if at any time chest compression stop/pause. In such a case, the system can monitor the amount of time during which a change in the thoracic cavity is not detected. If no change is detected for a pre-set time, the control unit can reset the rate of assisted ventilation to the initial rate or an alternate rate that is not dependent upon chest compression. In addition, if the patient's pulse resumes, the system can continue to provide assisted ventilation at a pre-determined rate, volume, etc. Alternatively, the system can enter a manual mode where a caregiver can deliver assisted ventilation upon demand (e.g., using the manual trigger button). Furthermore, the system can be configured to check for a patient's pulse and use identification of the pulse to adjust the rate of assisted ventilation or cease assisted ventilation.

The manual trigger allows the caregiver to give a controlled ventilation on demand button may be beneficial once the patient has regained a pulse eliminating the need for external chest compression. As noted above, the device 100 can still continue isolation of the lungs by collapsing the esophagus with suction and/or direct air through the proper lumen into the lungs but changes the ventilation to an air bolus given on demand given by the caregiver. The manual trigger allows the caregiver to start the flow of air to the lungs. Release of the trigger stops the flow of air to the lungs to allow the patient to exhale. Alternatively, a single actuation of the trigger can give a preset amount of air that ventilates the patient.

The system described herein can also be used with conventional rescue devices.

For example, the ventilation system can be configured to work with an active chest compression device so that ventilations and chest compressions are timed to increase effectiveness of both the compression and ventilation. The coupling can be mechanical and/or electrical. The ventilation system can also include carbon dioxide sampling so that carbon dioxide levels are outputted via a signal or gas stream to a monitor or other notification means as described herein.

Figure 11A:
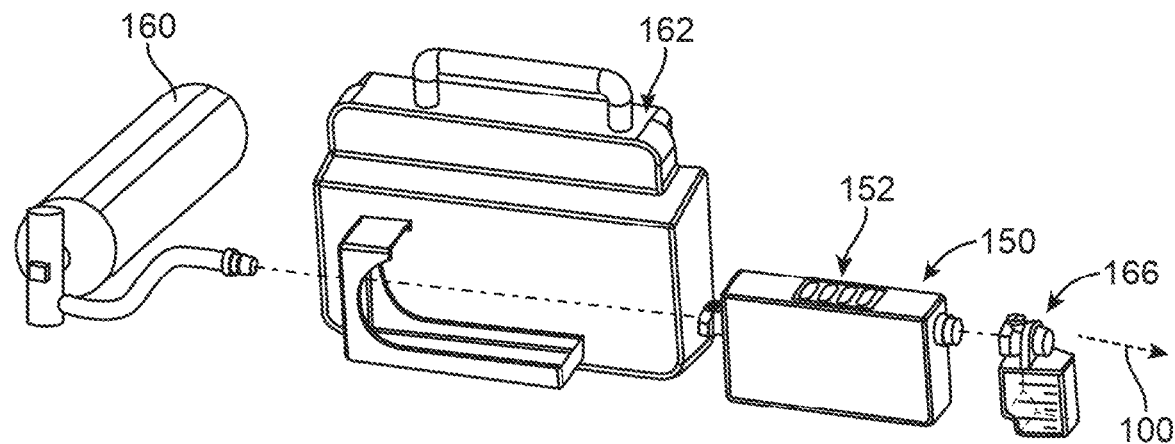
FIGS. 11A and 11B illustrate a variation of a system for artificially ventilating an individual using a source of oxygen, such as those described herein.
Figure 11B:
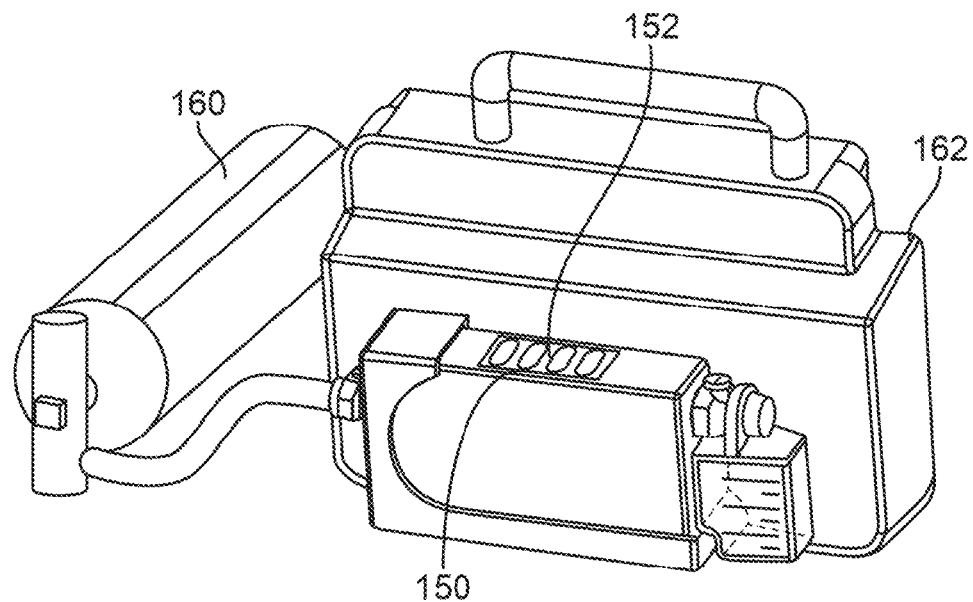
Figure 11C:
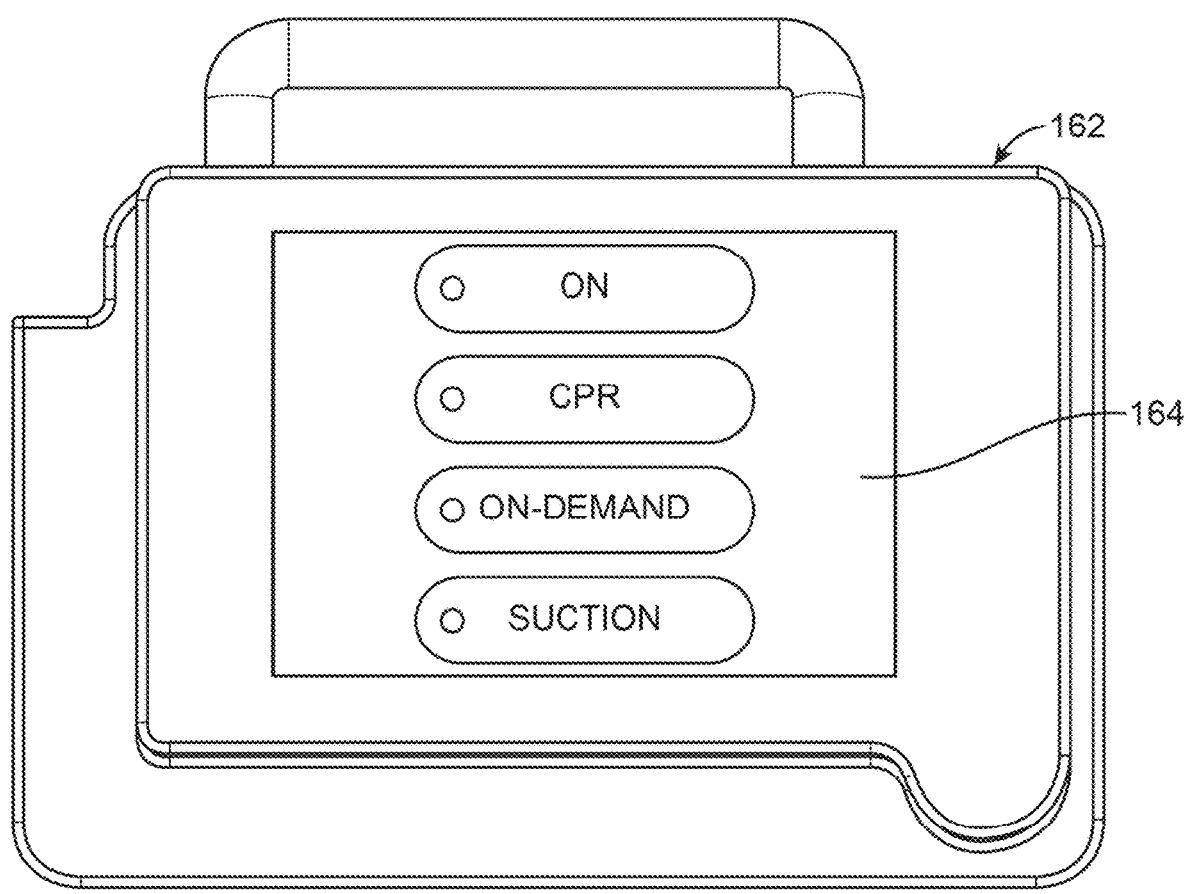
FIG. 11C shows an external device being used to control the ventilator described herein.

FIGS. 11A and 11B illustrate a variation of a system for artificially ventilating an individual using a source of oxygen, such as those described herein. In the illustrated example, the device 100 is not shown for purposes of clarity in illustration how the control system 150 can be used as a stand-alone unit having electrical control systems having firmware can be controlled through the system interface 152, or can be integrated or controlled with an external device (e.g., a cardiac monitor, monitor/defibrillator, or other critical care device). As shown, the control unit 150 can be mounted on the external device 162 and coupled to a source of oxygen 160. As shown in FIG. 11B, once coupled to the external device 162, the control unit 150 can be operated using the on-board controls 152 or can be controlled via the external device 162 via a wireless or wired connection. In such a case and as shown in FIG. 11C, one or more of the on-board controls 152 of the control unit 150 can be displayed on the control/display 164 of the external device 162. The variation shown in FIG. 11C illustrates controls for operating the device 100 in a CPR mode, on-demand mode, or suction mode. However, any number of items can be displayed on the control/display 164 and/or on the on-board controls 152.

For example, the device 100 can display information relating to the phase, rate, efficiency, depth, ratios of chest compression during CPR. Additionally, the device can display information for giving an operator real time feed-back on the efficiency of the assisted compressions via audible or visual feedback as well as information on whether to increase or decrease the speed of manual compressions, or whether to resume chest compressions if pulses are lost or the caregiver stops chest compression for too long.

The device 100 can also be configured with a rechargeable power supply that can be charged when coupled to an external device 162, or where the connection allows for charging the device 100 via a typical AC power source. In most cases, the control unit 150 will carry a power supply capable of powering the device for a sufficient period of operation and a sufficient stand-by period.

Figure 12:
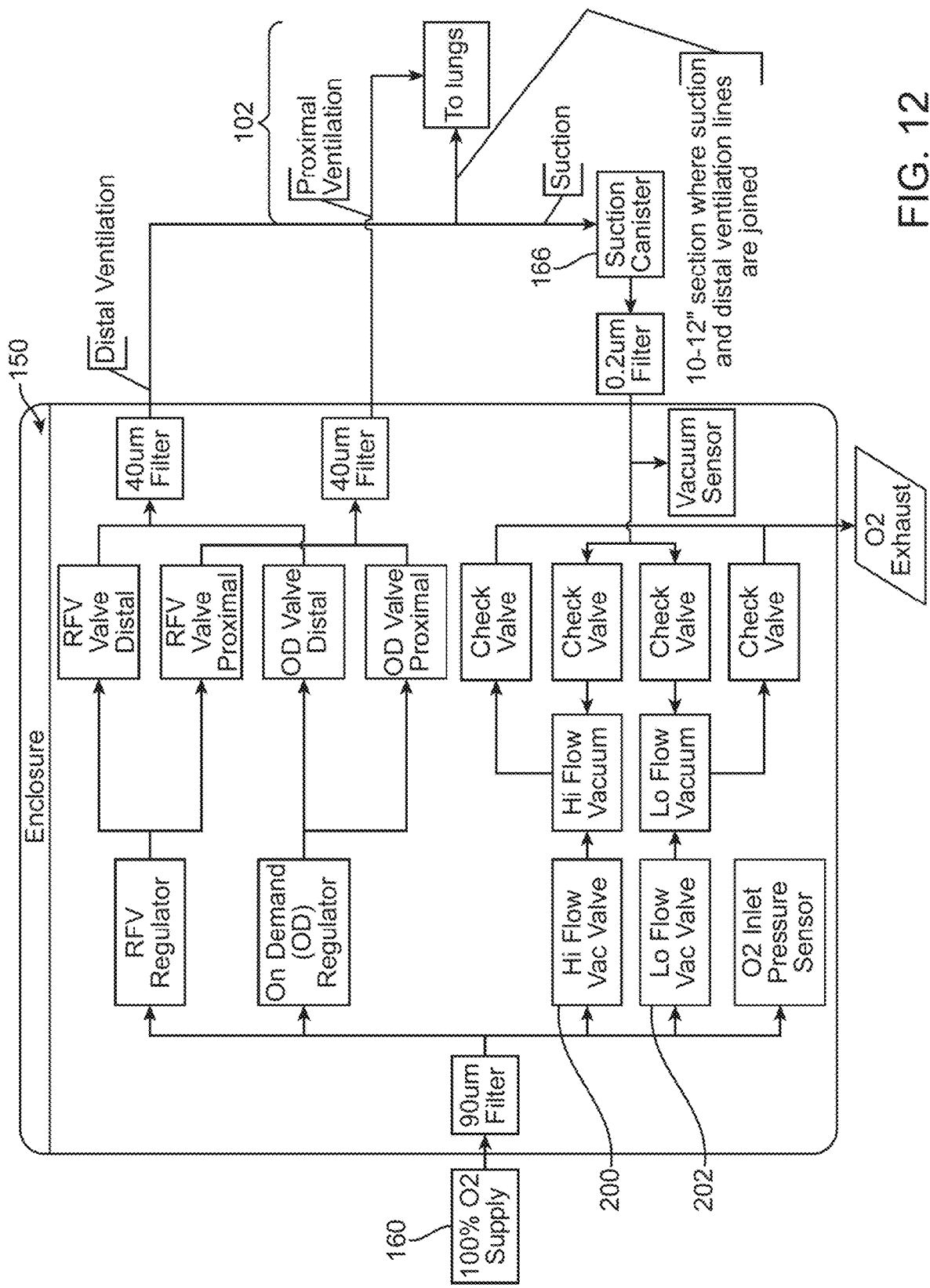
FIG. 12 provides a schematic of a control system relying on the gas supply to provide a source for both ventilation and suction.
Figure 13:
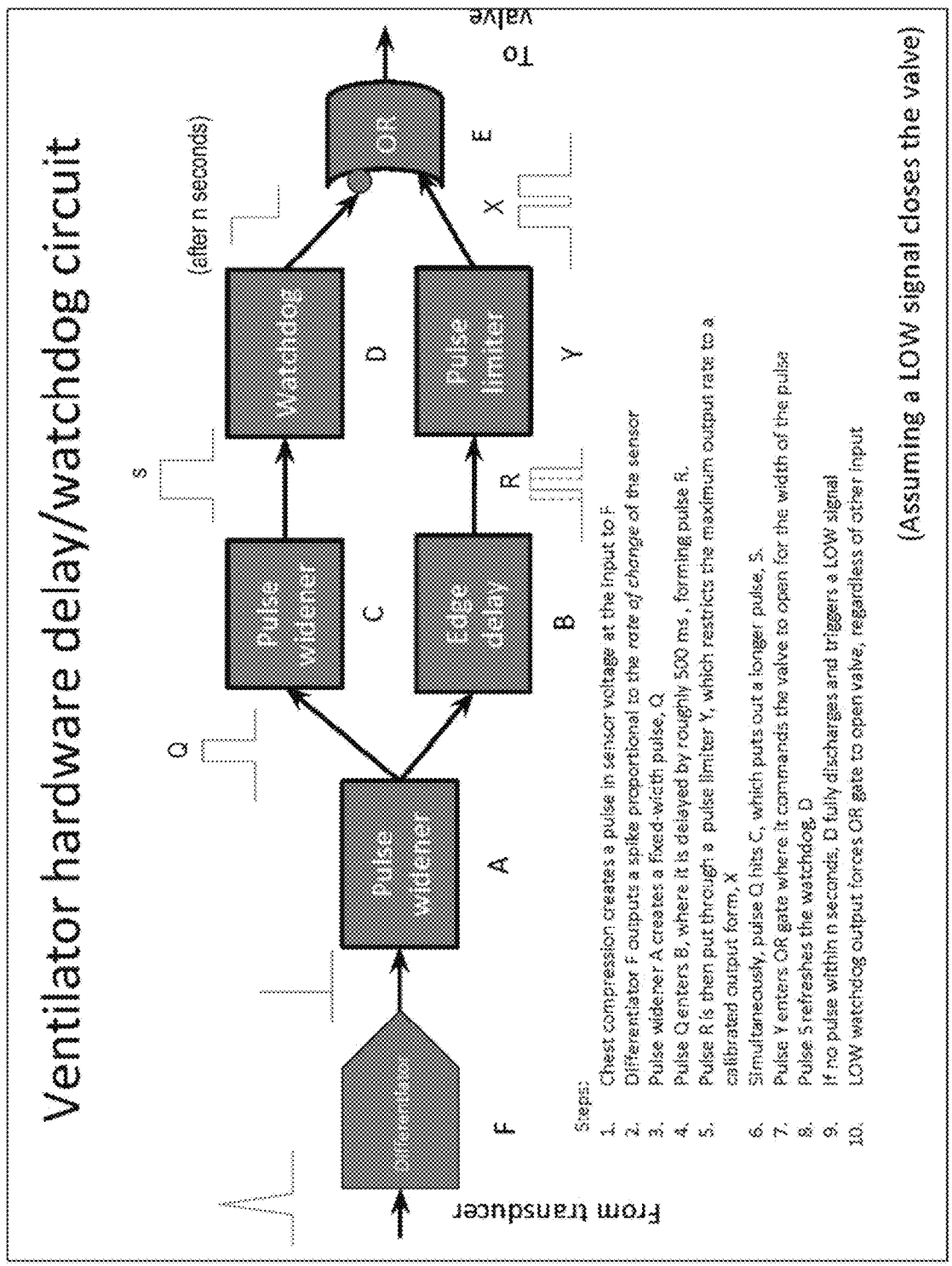
Figure 14:
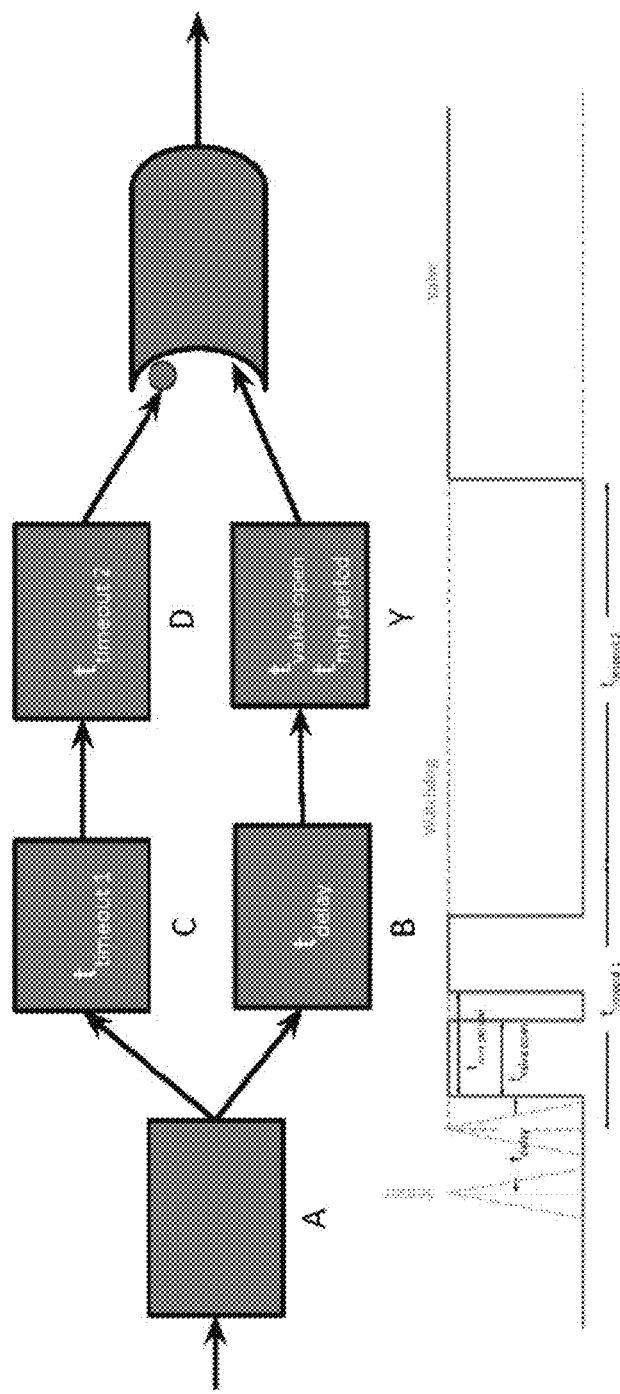
Figure 15:
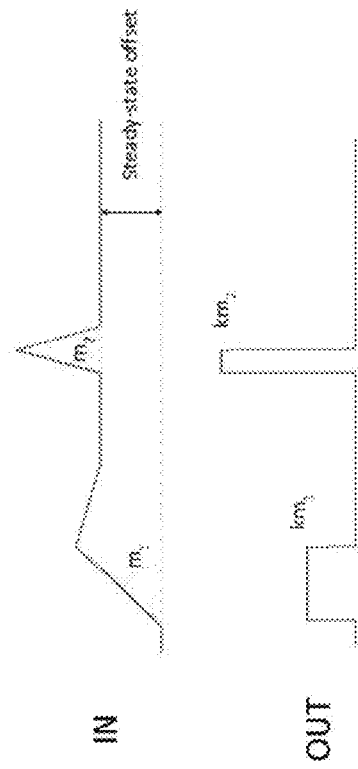
Figure 16:
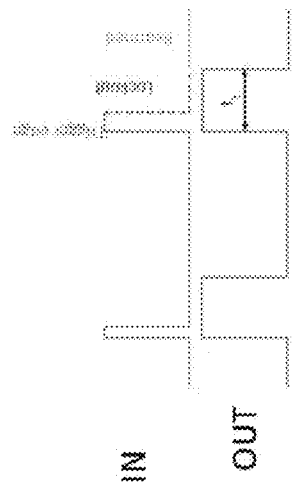
Figure 17:
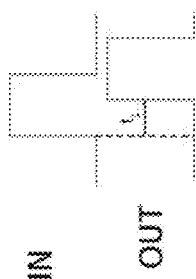
Figure 18:
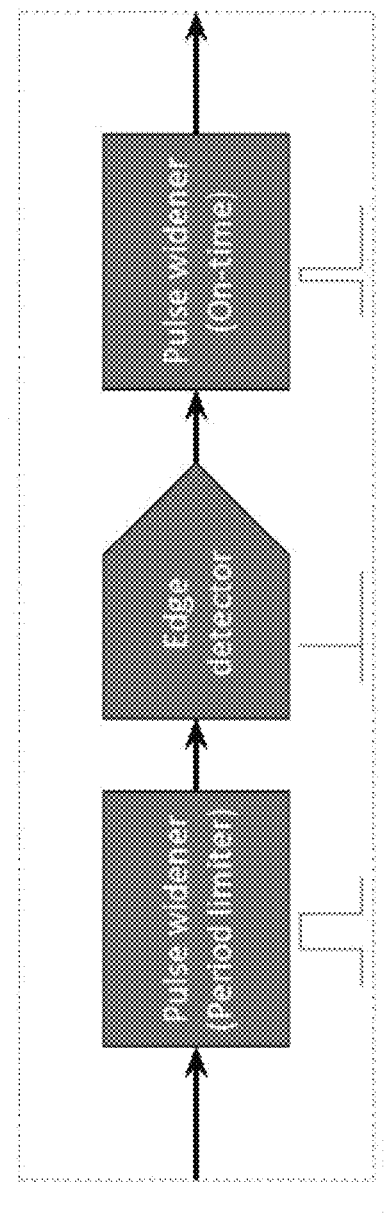
Figure 19:
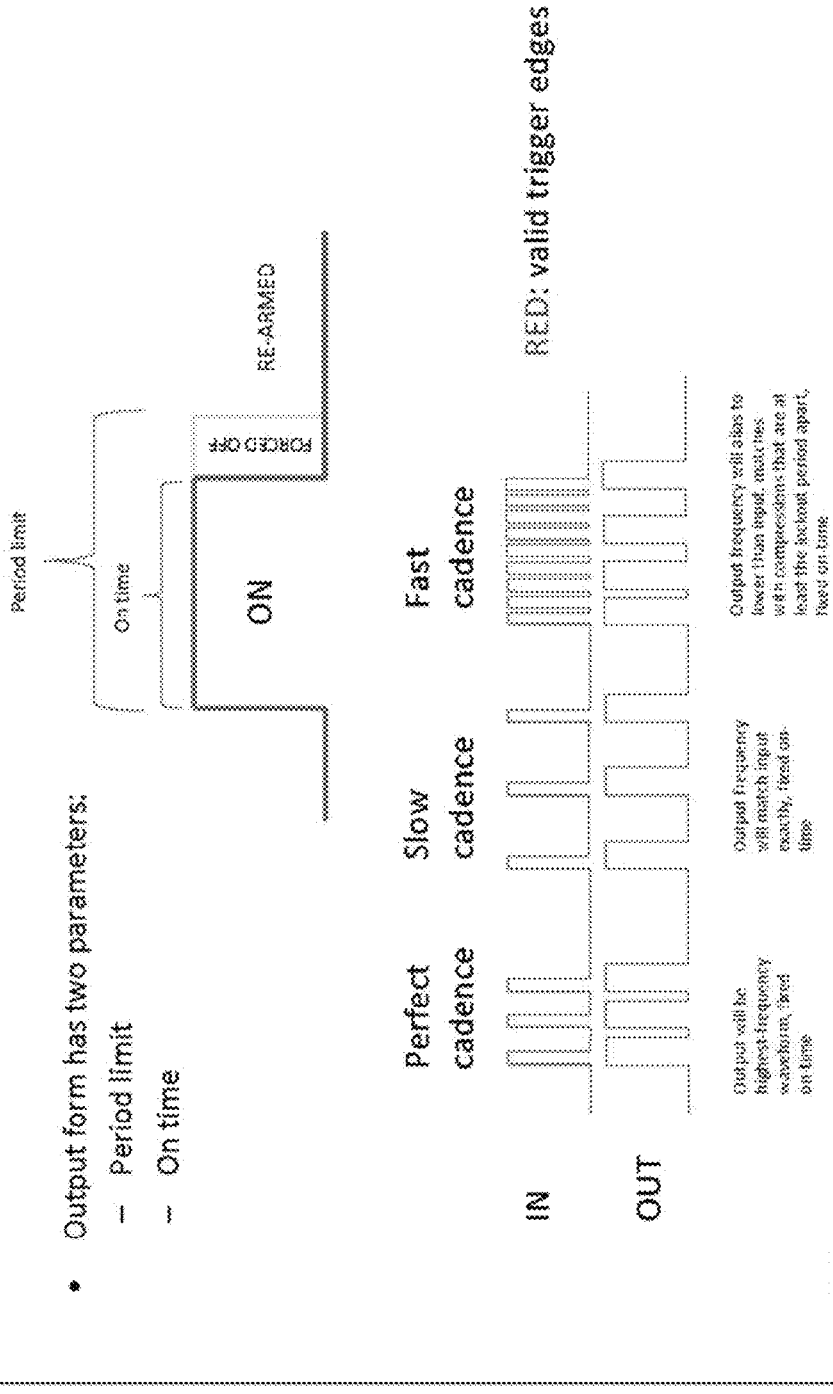
Figure 20:
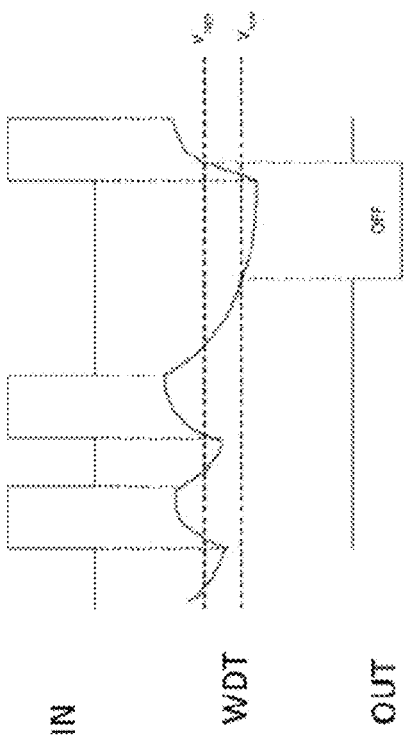
Figure 22:
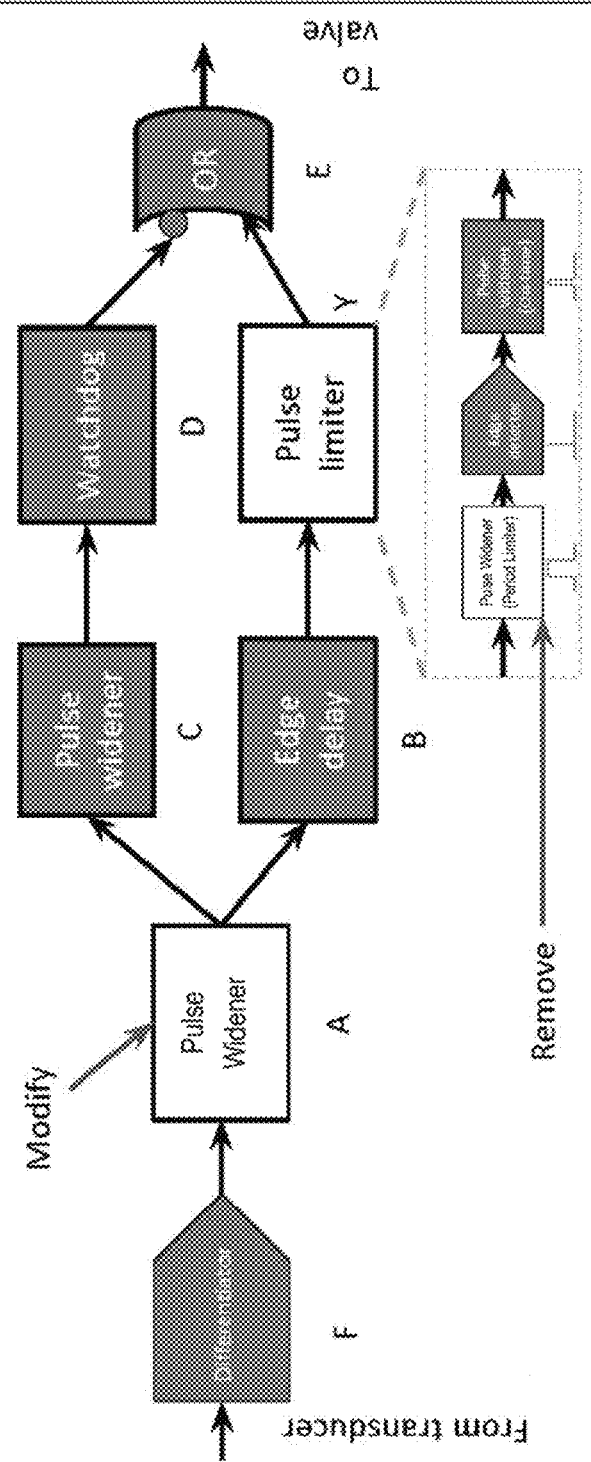

FIG. 12 illustrates an additional improvement to increasing the portability of the control unit 150. In this configuration, the control unit 150 relies upon the source of oxygen 160 to provide ventilation to the individual as well as to produce the vacuum described above. Accordingly, to extend the source of the oxygen, the device can employ one or more vacuum valves 200, 202 that produce a vacuum as a result of the pressurized flow of oxygen where one vacuum valve operates at a high flow to generate suction. Once a vacuum is established for a certain period of time, the system can switch to a low flow vacuum valve 202 that generates high vacuum with low flow. Such a configuration extends the life of the oxygen supply.

In another variation, the devices described herein can be used to determine ventilation parameters using tubing that accommodates different sizes. For example, having a variety of working ends of different sizes that were coordinated with a Broslow tape for pediatric applications. This way a caregiver could simply select the size airway the Broslow tape recommended and attach to the ventilator. The caregiver would not have to adjust the ventilation parameters because either the authentication process would signal to the ventilator the approximate size of the patient based on the airway selected. Alternatively, the airway itself would reduce the volume, pressure, suction pressure that the patient received. An example of this method would be a narrowing of the ventilation tubing that restricted flow, so the volume ventilated over a period of time was less. Another example would be an exhaust valve the dumped excess ventilation volume into the atmosphere, reducing both the volume and pressure for ventilating the patient.

The methods described herein allow for determining the phase, rate, efficiency, depth, ratios of chest compression during CPR by detecting the bending of a tube placed in the patient's mouth, esophagus via various methods. Including but not limited to, strain gauges on tube, fiber optics, air movement sensors. Another variation of the method include timing ventilations at a certain phase of the compression to maximize the efficiency of CPR while allowing adequate gas exchange. Another variation of the methods includes continuing ventilations after compressions are stopped or paused. The methods can also provide an operator with real time feedback on the efficiency of rescuers compressions via audible or visual feedback. The methods described herein can use the ventilator described herein or can use any ventilation device.

Some of the features of the systems described above include: a method for placing electrodes on the tube and pacing the heart via tube placed in the mouth, esophagus or trachea; a method for defibrillating the heart through electrodes placed on a tube in the mouth, trachea or esophagus of a patient; and a method for determining if the patient has a pulse or mechanical contraction of the heart through a tube in the patients mouth, trachea or esophagus.

FIGS. 19-28 illustrate an example of the circuitry for sensing the phase, rate, depth and effectiveness of a chest compression with a resistor placed on the tube of an airway placed in the patient's mouth, trachea or esophagus. The information can be relayed to the rescuer or used to signal a valve to time a ventilation. This is only one example of how to implement the invention described above by no way are we limiting other methods mentioned above.

In an additional variation, the present system can monitor a pressure in the thoracic cavity at a high rate for subtle changes in pressure. For instance, the system can continuously monitor pressure within the thoracic cavity by monitoring pressure along the working end or at the distal end of the device. The system can trigger a rapid response to any pressure change. For example, if the system does not detect any pressure changes (or if the detected pressure changes are below a pre-determined threshold), the system can ventilate the patient at a set rate to ensure the patient is being ventilated without simultaneous chest compressions.

The current system does not require the patient attempting to take breathes to ventilate the patient. Instead, the present system monitors pressure within the chest of the individual to adjust timing and parameters of the supplied ventilation. For instance, the present system can include a "CPR mode" that monitors pressure in the thoracic cavity of the individual. The system can monitor pressure within the thoracic cavity and use this measurement to determine whether the patient is undergoing chest compressions. If chest compressions are detected, the system can stop providing ventilation. Alternatively, if measurement of the thoracic pressure indicates that no-chest compressions are being administered, the system can provide ventilations at a set rate to ensure that the patient is being ventilated.

Also, these automatic non-triggered ventilations ensure that air is present in the thoracic cavity when chest compressions are eventually initiated or resumed so the system can more easily detect chest compressions. One benefit of this configuration is that the ventilation systems is not reliant on the patient attempting to take breathes to trigger ventilations. The present system is not dependent on a patient taking a breath but a medical provider compressing the chest. The present system can use both the positive pressure and negative pressure changes in the chest to adjust the timing and ventilation parameters.

Variations of the current system can detect very subtle pressure changes in the airway as well as in the ventilation device. As noted above, conventional ventilations systems use pressure changes to detect a patient's own respirations, which requires a large change in pressure within the lungs. In variations of the present system, the ability to detect small or subtle pressure changes allows the system to detect smaller pressure changes that are associated with chest compressions occurring an open thoracic cavity (i.e., the lungs are not isolated from the atmosphere via balloons or other isolation devices.) The present system can also use the same pressure sensor line to detect subtle pressure changes in the thoracic cavity that are associated with the contraction of the heart.

A variation of the present system includes a dedicated, small diameter (e.g., 1 mm or less) that travels independently from the active ventilation tubing to the working distal end of the intubation device. This separate lumen reconnects at the working end of the device. Such a configuration allows for sampling the pressure in the patient without any influence from any venture effect of the ventilator. This configuration also improves the accuracy of the pressure reading inside the patient. Therefore, the system is more accurate and responsive in detecting minor pressure changes associated with chest compressions and/or contractions of the heart.

Use of a separate pressure also provides other benefits over conventional devices. For example, conventional devices use a single lumen tube with internal diameters starting around 5 mm for adults and then increasing to 25 mm for the connection tubing which then travels 3-7 feet to connect to a ventilator that often houses the pressure sensors. Sampling a subtle (0.005-1.0 cmH20) pressure change and then propagating that signal to the sensor proves difficult. Many current ventilation tubing and connectors also increase in diameter as they travel from the patient to the ventilator. This increased diameter causes a diminishing the signal. As noted above, when a sensor shares the same lumen as the lumen used for ventilation, the pressure reading often becomes variable and unreliable because of the venturi effects of the moving ventilation air. This is especially true when utilizing a jet ventilation technique. Also, there is often a difference in pressure between the up-stream portion of the ventilator where the ventilation pressure is generated, and pressure measured downstream, at a distal end of the airway. Measurement of the pressure at the distal end of the device usually corresponds to the pressure in the patient.

As noted herein, the present devices can be used to assist a patient experiencing cardiac arrest. In such a case, it is important to determine if the patient has palpable blood flow through their arteries. Typically, this is performed by a care provider who attempts to feel a pulse in the patient's radial, femoral, carotid arteries that correlates to the electrical reading of their heart on the EKG machine. However, in the emergency setting, it is difficult to identify pressures through palpation. In some cases, the patient can have electrical signals propagating through cardiac tissue causing contraction of the heart, but the contractions are insufficient to create a significant change in blood pressure. This condition is called Pulseless Electrical Activity (PEA). It is important for the care provider to distinguish between PEA that produces muscle contraction of the heart or an electrical signal without heart muscle contraction. Identifying the condition is important in determining the treatment for the patient. Currently in order to differentiate these a provider must monitor the patient for an electrical cardiac signal and use precise imaging such as ultrasound to find the heart and then determine muscle movement that correlates to the electrical signal. The configuration of the devices described herein allow for measurement of pressure changes in the thoracic cavity, which arise from pressure changes associated with muscle contractions of the heart. The present devices can then use an EKG reading (whether through another EKG machine or included in the present devices) to determine if these pressure changes are associated with heart contractions. This information can then be relayed to the care provider to determine the treatment of the patient without the need for additional imaging equipment or medical evaluation. The detection of heart contractions by measuring pressure changes in the airway or esophagus can also be relayed via audio or visual prompts to allow a care provider to compare the prompts to any EKG signal.

Additional variations of the devices described herein can also provide electrical stimulation of heart tissue during emergency care. Electrical stimulation can be used to either reset the deadly rhythms ventricular fibrillation or pulseless ventricular tachycardia. Electrical stimulation can also be used to cause extra heart contractions if the heart is beating slowly or irregularly. Currently in emergency medicine most electrical stimulation of the heart occurs through the use of external pacing pads placed in various locations of the chest and back. These external pads must pass sufficient energy through the body to capture the heart. Often, because of impedance of the other tissue/organs, external pads require energy in excess of 360 joules. As an alternative, the present devices can include one or more defibrillation electrodes on the distal tubing of the device where the tubing will have contact with the esophagus. Positioning of an electrode in this manner places the electrode closer to the heart thus reducing impedance that is encountered by external electrodes. Therefore, applying electrical stimulation using the device allows for efficient electrical stimulation of heart tissue with less energy. Using suction to pull the esophagus into contact with the electrodes ensures there is proper contact with the pad and the tissue of the esophagus. A 2nd pad can be positioned along the same tube or on any portion of the chest.

Variations of the devices described herein are configured to adjust to a range of different sizes for adult airways. However, for pediatric applications, the ventilation devices can be provided in a variety of sizes as well as a change in the parameters for ventilation and suction depending on the individual pediatric patient. The present devices can include a verification chip on a disposable component of the device (e.g., the tubing or mask), where the verification chip is read by the control unit (e.g., see 150 of FIG. 3A), the control unit can confirm that the ventilation device is a single use device manufactured by an approved vendor. Using this same verification chip, the ventilation system can also to determine the particular size of the pediatric ventilation device and adjust the ventilation specific parameters accordingly.

Figure 23A:
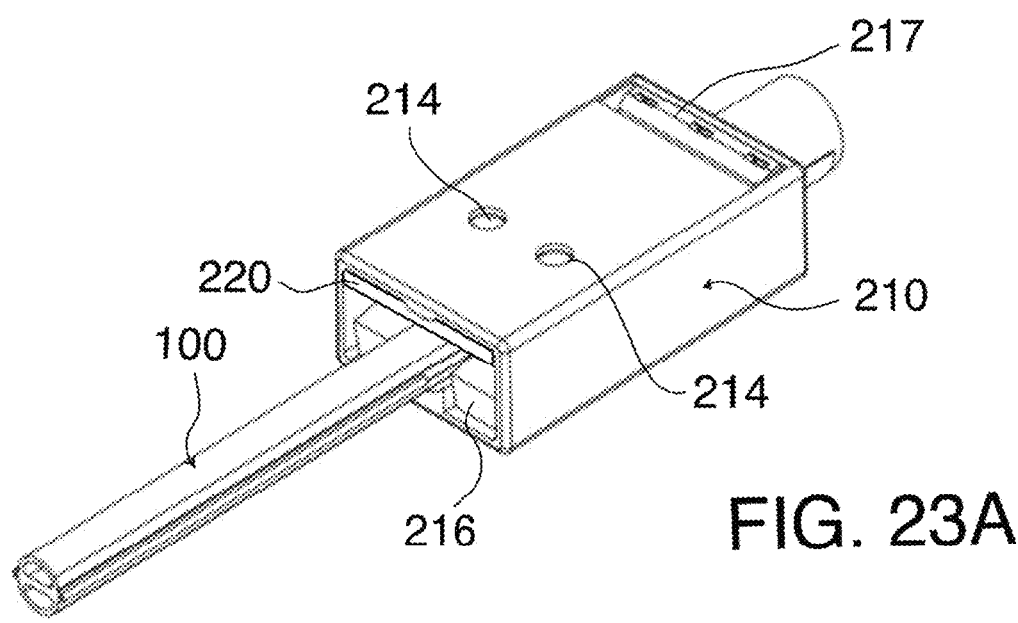
FIG. 23A to 23C illustrates a lubrication/sterilization housing that sterilizes and/or lubricates the device prior to use.
Figure 23B:
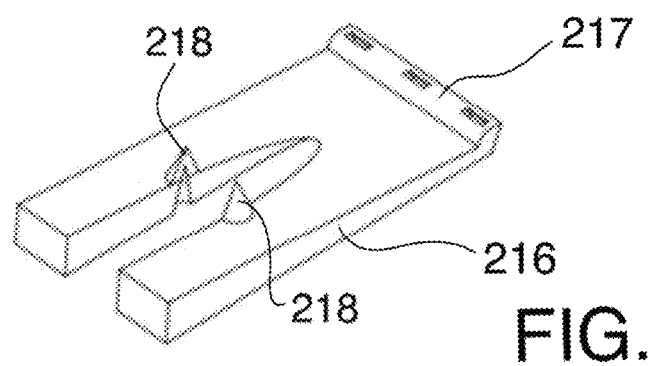
Figure 23C:
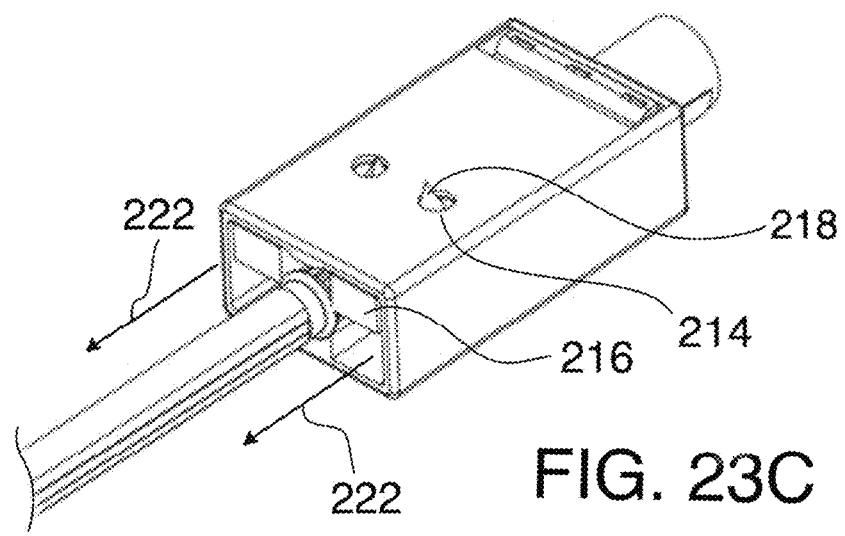

FIGS. 23A to 23C illustrate another variation of a device 100 having a lubrication housing 210 that is positioned about the device 100. The lubrication housing 210 includes a lubrication source 220, gel lubrication used for endotracheal tubes. The lubrication source 220 is positioned within the housing 210 and adjacent to a lever arm 216. The lever arm 216 is configured to be pivotally coupled within the housing 210. For example, the lever arm 216 can include a hinge section 217 that permits movement of the lever arm 216 within the housing 210. In the illustrated variation, the housing 210 includes one or more openings 214 that receive piercing members 21 that can be coupled to the lever arm 216 (shown in FIG. 23B). FIG. 23C illustrate an example of the lever arm 216 being driven against the lubrication supply (not shown) where the piercing members 218 puncture the supply and extend through openings 214 in the housing 210. The lever arm 216 can be configured to compress the supply 220 upon removal of the housing body 210 from the device 100 as shown by arrows 222. The lever arm 216 can be driven by any cam/follower configuration, or any configuration that prevents inadvertent compressing of the lubrication supply 220. Once the lubrication supply 220 is punctured, removal of the housing body 210 from the device causes the shaft of the device 210 to be coated with the lubrication gel along a partial or full length of the shaft. In additional configurations, the gel includes an anti-bacterial substance in place of or in addition to the lubrication substance.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

It must be noted that as used herein and in the appended claims, the singular forms "a", "an", and "the" include plural referents unless the context clearly dictates otherwise. Thus, for example, reference to "a string" may include a plurality of such strings and reference to "the tubular member" includes reference to one or more tubular members and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

I claim:

1. A method for ventilating in an individual and increasing an efficiency of a chest compression, the method comprising:
    inserting a device within a respiratory opening of the individual, the device having a working portion for positioning within a body passageway of the individual, the device having a pressure lumen exposed at the working portion;
    detecting a pressure change within the body passageway using the pressure lumen;
    delivering a bolus of air through the working portion to ventilate the individual;
    altering a timing of delivery of the bolus of air upon detecting the pressure change in the body passageway resulting from the chest compression to deliver a delayed bolus of air after the chest compression; and
    delivering the delayed bolus of air at a volume to re-expand a chest cavity of the individual and to assist in a recoil of the chest cavity to a greater volume, which increases an effectiveness of a subsequent chest compression and increases circulation of blood.

2. The method of claim 1, wherein the working portion includes a distal opening of the device fluidly coupled to a first lumen and a medial opening fluidly coupled to a second lumen, the method further comprising:
    pulling a suction force through the distal opening and maintaining the suction force for a period of time;
    ventilating the individual through the first lumen if tissue from the body passageway does not seal the distal opening; and
    ventilating the individual through the second lumen and maintaining the suction force through the distal opening if the tissue from the body passageway seals the distal opening.

3. The method of claim 2, further comprising initially ventilating through the second lumen during application of suction through the first lumen.

4. The method of claim 2, further comprising deploying an anchor to temporarily secure the device in the body passageway.

5. The method of claim 2, where the body passageway comprises a trachea and where the working portion of the device is positioned within the trachea.

6. The method of claim 2, where the body passageway comprises an esophagus of the individual and where the working portion of the device is positioned within the esophagus.

7. A method for ventilating in an individual and increasing an efficiency of a chest compression, the method comprising:
    inserting a device within a respiratory opening of the individual, the device having a working portion for positioning within a body passageway of the individual, the device having a pressure lumen exposed at the working portion;
    detecting a pressure change within the body passageway using the pressure lumen;
    delivering a bolus of air through the working portion to ventilate the individual;
    altering a timing of delivery of the bolus of air upon detecting the pressure change in the body passageway resulting from the chest compression to deliver a delayed bolus of air after the chest compression; and
    delivering the delayed bolus of air at a pressure to expand a chest cavity of the individual and to assist in a recoil of the chest cavity to a greater volume, which increases an effectiveness of a subsequent chest compression and increases circulation of blood.

* * * * *